(12) United States Patent
Irving et al.

(10) Patent No.: US 8,217,149 B2
(45) Date of Patent: Jul. 10, 2012

(54) ANTI-PD-L1 ANTIBODIES, COMPOSITIONS AND ARTICLES OF MANUFACTURE

(75) Inventors: Bryan Irving, San Francisco, CA (US); Henry Chiu, San Francisco, CA (US); Heather Maecker, Palo Alto, CA (US); Sanjeev Mariathasan, Millbrae, CA (US); Sophie M. Lehar, Montara, CA (US); Yan Wu, Foster City, CA (US); Jeanne Cheung, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 93 days.

(21) Appl. No.: 12/633,339

(22) Filed: Dec. 8, 2009

(65) Prior Publication Data
US 2010/0203056 A1    Aug. 12, 2010

Related U.S. Application Data

(60) Provisional application No. 61/121,092, filed on Dec. 9, 2008.

(51) Int. Cl.
*C07K 16/00* (2006.01)
(52) U.S. Cl. .................................... 530/387.1
(58) Field of Classification Search .................. None
See application file for complete search history.

(56) References Cited

U.S. PATENT DOCUMENTS

| | | | |
|---|---|---|---|
| 5,629,204 A | 5/1997 | Honjo et al. | |
| 5,698,520 A | 12/1997 | Honjo et al. | |
| 6,075,181 A | 6/2000 | Kucherlapati et al. | |
| 6,150,584 A | 11/2000 | Kucherlapati et al. | |
| 6,630,575 B2 | 10/2003 | Coyle et al. | |
| 6,632,927 B2 * | 10/2003 | Adair et al. | 530/387.3 |
| 6,803,192 B1 | 10/2004 | Chen | |
| 6,808,710 B1 | 10/2004 | Wood et al. | |
| 6,905,688 B2 | 6/2005 | Rosen et al. | |
| 6,936,704 B1 | 8/2005 | Freeman et al. | |
| 6,965,018 B2 | 11/2005 | Mikesell et al. | |
| 6,982,321 B2 | 1/2006 | Winter | |
| 7,029,674 B2 | 4/2006 | Carreno et al. | |
| 7,030,219 B2 | 4/2006 | Pardoll et al. | |
| 7,038,013 B2 | 5/2006 | Freeman et al. | |
| 7,041,474 B2 | 5/2006 | Kingsbury | |
| 7,087,409 B2 | 8/2006 | Barbas, I et al. | |
| 7,101,550 B2 | 9/2006 | Wood et al. | |
| 7,105,328 B2 | 9/2006 | Wood et al. | |
| 7,385,036 B2 | 6/2008 | Kingsbury | |
| 7,408,041 B2 | 8/2008 | Bowdish et al. | |
| 7,414,171 B2 | 8/2008 | Honjo et al. | |
| 7,560,540 B2 | 7/2009 | Pardoll et al. | |
| 7,563,869 B2 | 7/2009 | Honjo et al. | |
| 7,595,048 B2 | 9/2009 | Honjo et al. | |
| 7,794,710 B2 | 9/2010 | Chen et al. | |
| 7,799,899 B2 * | 9/2010 | Ackerly et al. | 530/387.1 |
| 2002/0107363 A1 | 8/2002 | Fox et al. | |
| 2002/0164600 A1 | 11/2002 | Freeman et al. | |
| 2003/0003953 A1 | 1/2003 | Houplain | |
| 2003/0039653 A1 | 2/2003 | Chen et al. | |
| 2003/0118592 A1 | 6/2003 | Ledbetter et al. | |
| 2003/0161827 A1 | 8/2003 | Celnicker et al. | |
| 2003/0180309 A1 | 9/2003 | Baum et al. | |
| 2003/0216546 A1 | 11/2003 | Tykocinski et al. | |
| 2003/0232323 A1 | 12/2003 | Freeman et al. | |
| 2004/0033497 A1 | 2/2004 | Alarcon-Riquelme et al. | |
| 2004/0110290 A1 | 6/2004 | June et al. | |
| 2004/0180047 A1 | 9/2004 | Chen et al. | |
| 2004/0191235 A1 | 9/2004 | Groux et al. | |
| 2004/0213795 A1 | 10/2004 | Collins et al. | |
| 2004/0248205 A1 | 12/2004 | Stern et al. | |
| 2005/0191296 A1 | 9/2005 | Kaempfer et al. | |
| 2005/0208496 A1 | 9/2005 | Ohtani et al. | |
| 2006/0003452 A1 | 1/2006 | Humeau et al. | |
| 2006/0034810 A1 | 2/2006 | Riley et al. | |
| 2006/0083744 A1 | 4/2006 | Chen et al. | |
| 2006/0110755 A1 | 5/2006 | Duke et al. | |
| 2006/0153841 A1 | 7/2006 | Freeman et al. | |
| 2006/0165665 A1 | 7/2006 | Min et al. | |
| 2006/0269526 A1 | 11/2006 | Galipeau et al. | |
| 2006/0276422 A1 | 12/2006 | Usman et al. | |
| 2007/0036783 A1 | 2/2007 | Humeau et al. | |
| 2007/0054360 A1 | 3/2007 | Gao et al. | |
| 2007/0100098 A1 | 5/2007 | Ooura et al. | |
| 2007/0110746 A1 | 5/2007 | Chung | |
| 2007/0122378 A1 | 5/2007 | Freeman et al. | |
| 2007/0172504 A1 | 7/2007 | Shirwan et al. | |
| 2007/0212733 A1 * | 9/2007 | Martin | 435/7.21 |

(Continued)

FOREIGN PATENT DOCUMENTS
EP    1445264 A1    8/2004
(Continued)

OTHER PUBLICATIONS

Rudikoff et al. 1982, Proc. Natl. Acad. Sci. USA, , 79: 1979-1983.*
Panka et al., 1988, Proc. Natl. Acad. Sci. USA, 85: 3080-3084.*
Huang Z., Pharmacology and Therapeutics, 2000, 86: 201-215.*
Agata et al., "Expression of the PD-1 antigen on the surface of stimulated mouse T and B lymphocytes" *International Immunology* 8(5):765-772 (Feb. 6, 1996).
Azuma et al., "B7-H1 is a ubiquitous antiapoptotic receptor on cancer cells" *Immunobiology* 111(7):3635-3643 (Apr. 2008).
Boussiotis et al, "The Role of B7-1/B7-2:CD28/CLTA-4 Pathways in the Prevention of Anergy, Induction of Productive Immunity and Down-Regulation of the Immune Response" *Immunological Reviews*153:5-26 (1996).

(Continued)

*Primary Examiner* — Ilia Ouspenski
(74) *Attorney, Agent, or Firm* — Craig G. Svoboda

(57) ABSTRACT

The present application relates to anti-PD-L1 antibodies, nucleic acid encoding the same, therapeutic compositions thereof, and their use enhance T-cell function to upregulate cell-mediated immune responses and for the treatment of T cell dysfunctional disorders, including infection (e.g., acute and chronic) and tumor immunity.

61 Claims, 17 Drawing Sheets

U.S. PATENT DOCUMENTS

| | | | |
|---|---|---|---|
| 2007/0243548 | A1 | 10/2007 | Georges et al. |
| 2008/0025979 | A1 | 1/2008 | Honjo et al. |
| 2009/0215053 | A1 | 8/2009 | Galon et al. |

FOREIGN PATENT DOCUMENTS

| | | |
|---|---|---|
| EP | 1537878 A1 | 6/2005 |
| WO | 01/14557 A1 | 3/2001 |
| WO | 01/34629 A1 | 5/2001 |
| WO | 01/39722 A2 | 6/2001 |
| WO | 02/068647 A2 | 9/2002 |
| WO | 02/072631 A2 | 9/2002 |
| WO | 02/077208 A1 | 10/2002 |
| WO | 02/079499 A1 | 10/2002 |
| WO | 02/092792 | 11/2002 |
| WO | 03/042402 A2 | 5/2003 |
| WO | 2006/042237 A2 | 4/2006 |
| WO | 2006/121168 A1 | 11/2006 |
| WO | 2006/133396 A2 | 12/2006 |
| WO | 2007/005874 A2 | 1/2007 |
| WO | 2007/082144 A2 | 7/2007 |
| WO | 2007/082154 A2 | 7/2007 |
| WO | 2007/124361 A2 | 11/2007 |
| WO | 2008/011344 A2 | 1/2008 |
| WO | 2008/034076 A2 | 3/2008 |
| WO | 2008/057632 A1 | 5/2008 |
| WO | 2008/067283 A2 | 6/2008 |
| WO | 2008/071447 A2 | 6/2008 |
| WO | 2008/083174 A2 | 7/2008 |
| WO | 2008/085562 A2 | 7/2008 |
| WO | 2008/091643 A2 | 7/2008 |
| WO | 2008/092153 A2 | 7/2008 |
| WO | 2009/108341 A1 | 9/2009 |
| WO | 2009/111315 A2 | 9/2009 |
| WO | 2009/114335 A2 | 9/2009 |

OTHER PUBLICATIONS

Boussiotis et al., "Blockade of the CD28 co-stimulatory pathway: a means to induce tolerance" *Immunology* 6:797-807 (1994).

Carreno et al., "The B7 Family of Ligands and Its Receptors: New Pathways for Costimulation and Inhibition of Immune Responses" *Annu. Rev. Immunol.* 20:29-53 (2002).

Chen, "Overcoming T Cell Ignorance by Providing Costimulation" *Gene Therapy of Cancer—Advances in Experimental Medicine and Biology* 451:159-165 (1998).

Curiel et al., "Blockade of B7-H1 improves myeloid dendritic cell-mediated antitumor immunity" *Nature Medicine* 9(5):562-567 (May 2003).

Dong et al., "Costimulating aberrant T cell responses by B7-H1 autoantibodies in rheumatoid arthritis" *The Journal of Clinical Investigation* 111(3):363-370 (Feb. 2003).

Ferrone et al., "How much longer will tumor cells fool the immune system?" *Immunology Today* pp. 3 (2000).

Freeman et al., "Protect the killer: CTLs need defenses against the tumor" *Nature Medicine* 8(8):787-789 (Aug. 2002).

Greenwald et al., "Negative co-receptors on lymphocytes" *Current Opinion in Immunology* 14:391-396 (2002).

Guinan et al., "Pivotal Role of the B7:CD28 Pathway in Transplantation Tolerance and Tumor Immunity" *Blood* 84(10):3261-3282 (Nov. 15, 1994).

Hellstrom et al., "Can Co-stimulated Tumor Immunity be Therapeutically Efficacious?" *Immunological Reviews* 145:123-145 (1995).

Hurwitz et al., "CTLA-4 blockade synergizes with tumor-derived granulocyte-macrophage colony-stimulating factor for treatment of an experimental mammary carcinoma" *Proc. Natl. Acad. Aci. USA* 95:10067-10071 (Aug. 1998).

Hurwitz et al., "Costimulatory wars: the tumor menace" *Current Opinion in Immunology* 12:589-596 (2000).

Iwai et al., "Involvement of PD-L1 on tumor cells in the escape from host immune system and tumor immunotherapy by PD-L1 blockade" *Proc. Natl. Acad. Sci. USA* 99(19):12293-12297 (Sep. 17, 2002).

Johnston et al., "B7-CD28 Costimulation Unveils the Hierarchy of Tumor Epitopes Recognized by Major Histocompatibility Complex Class I-restricted CD8 Cytolytic T Lymphocytes" *Journal of Experimental Medicine* 183:791-800 (Mar. 1996).

Kwon et al., "Manipulation of T cell costimulatory and inhibitory signals for immunotherapy of prostate cancer" *Proc. Natl. Acad. Sci. USA* 94:8099-8103 (Jul. 1997).

Leach at al., "Enhancement of Antitumor Immunity by CTLA-4 Blockade" *Science* 271:1734-1736 (Mar. 22, 1996).

Nishimura et al., "PD-1: an inhibitory immunoreceptor involved in peripheral tolerance" *Immunology Trends* pp. 4 (2001).

Okazaki et al., "New regulatory co-receptors: inducible co-stimulator and PD-1" *Current Opinion in Immunology* 14:779-782 (2002).

Oosterwegel et al., "The Role of CTLA-4 in Regulating Th2 Differentiation" *The Journal of Immunology* 163:2634-2639 (1999).

Petroff et al., "B7 Family Molecules: Novel Immunomodulators at the Maternal-Fetal Interface" *Placenta* 23(16):S95-S101 (2002).

Santra et al., "B7 co-stimulatory requirements differ for induction of immune responses by DNA, protein and recombinant pox virus vaccination" *European Journal of Immunology* 30:2650-2659 (2000).

Schweitzer at al., "The complexity of the B7-CD28/CTLA-4 costimulatory parthway" *Therapeutic Strategies for Modulating the Inflammatory Diseases* pp. 33-43 (1998).

Tamada et al., "Specific antitumor activity of tumor-infiltrating lymphocytes expanded first in a culture with both anti-CD3 monoclonal antibody and activated B cells and then in a culture with interleukin-2" *Cancer Immunol Immunother* 41:339-347 (1995).

Tamada et al., "T lymphocyte costimulatory molecules in host defense and immunologic diseases" *Annals of Allergy, Asthma & Immunology* 85:164-176 (2000).

Tamura et al., "B7-H1 costimulation preferentially enhances CD28-independent T-helper cell function" *Blood* 97(6):1809-1816 (Mar. 15, 2001).

Yang et al., "Costimulation in Immune Responses Against Tumors" *Molecular Approaches to Tumor Immunotherapy*, Chapter 9, pp. 191-211 (1998).

Agematsu et al., "Role of CD27 in T cell immune response. Analysis by recombinant soluble CD27" *J Immunol.* 153(4):1421-9 (Aug. 1994).

Aicher et al., "Characterization of human inducible costimulator ligand expression and function" *J Immunol.* 164(9):4689-96 (May 2000).

Aruffo et al., "Molecular Cloning of a CD28 cDNA by a High-Efficiency COS Cell Expression System" *Proc. Natl. Acad. Sci. USA* 84:8573-8577 (1987).

Azuma et al., "B70 antigen is a second ligand for CTLA-4 and CD28" *Nature* 366:76-9 (Nov. 1993).

Bansal-Pakala et al., "Defective T cell priming associated with aging can be rescued by signaling through 4-1BB (CD137)" *J Immunol.* 169(9):5005-9 (Nov. 2002).

Bansal-Pakala et al., "Signaling through OX40 (CD134) breaks peripheral T-cell tolerance" *Nat Med.* 7(8):907-12 (Aug. 2001).

Barber et al., "Restoring function in exhausted CD8 T cells during chronic viral infection" *Nature* 439:682-7 (Feb. 2006).

Beier et al, , "Induction, binding specificity and function of human ICOS" *Eur J Immunol.* 30(12):3707-17 (Dec. 2000).

Bertram et al., "Temporal segregation of 4-1BB versus CD28-mediated costimulation: 4-1BB ligand influences T cell numbers late in the primary response and regulates the size of the T cell memory response following influenza infection" *J Immunol.* 16;8(8):3777-85 (2002).

Beswick et al., "Expression of the programmed death ligand 1, B7-H1, on gastric epithelial cells after Helicobacter pylori exposure promotes development of CD4+ CD25+ FoxP3+ regulatory T cells" *Infect Immun.* 75(9):4334-41 (Sep. 2007).

Blank and Gajewski, "Interaction of PD-L1 on tumor cells with PD-1 on tumor-specific T cells as a mechanism of immune evasion: implications for tumor immunotherapy" *Cancer Immunol Immunother.* 54(4):307-14 (Apr. 2005).

Boerner et al., "Production of Antigen-Specific Human Monoclonal Antibodies From In Vitro-Primed Human Splenocytes" *J Immunol.* 147(1):86-95 (Jul. 1991).

Boettler et al., "Expression of the interleukin-7 receptor alpha chain (CD127) on virus-specific CD8+ T cells identifies functionally and phenotypically defined memory T cells during acute resolving hepatitis B virus infection" *J Virol.* 80(7):3532-40 (Apr. 2006).

Boise et al., "CD28 costimulation can promote T cell survival by enhancing the expression of Bcl-XL" *Immunity* 3(1):87-98 (Jul. 1995).

Boni et al., "Characterization of hepatitis B virus (HBV)-specific T-cell dysfunction in chronic HBV infection" *J Virol.* 81(8):4215-25 (Apr. 2007).

Boon et al., "From defined human tumor antigens to effective immunization?" *Immunology Today* 16(7):334-6 (Jul. 1995).

Bowen et al., "Structure and expression of murine CD30 and its role in cytokine production" *J Immunol.* 156(2):442-9 (Jan. 1996).

Bretscher et al., "A theory of self-nonself discrimination" *Science* 169:1042-9 (Sep. 1970).

Bretscher et al., "A two-step, two-signal model for the primary activation of precursor helper T cells" *Proc Natl Acad Sci U S A.* 96(1):185-90 (Jan. 1999).

Brocker et al., "CD4 T cell traffic control: in vivo evidence that ligation of OX40 on CD4 T cells by OX40-ligand expressed on dendritic cells leads to the accumulation of CD4 T cells in B follicles" *Eur J Immunol.* 29(5):1610-6 (May 1999).

Brown et al., "Blockade of programmed death-1 ligands on dendritic cells enhances T cell activation and cytokine production" *J Immunol.* 170(3):1257-66 (Feb. 2003).

Brunner et al., "CTLA-4-Mediated inhibition of early events of T cell proliferation" *J Immunol.* 162(10):5813-20 (May 1999).

Buhlmann et al., "A role for the B7-1/B7-2:CD28/CTLA-4 pathway during negative selection" *J Immunol.* 170(11):5421-8 (Jun. 2003).

Butte et al., "Programmed death-1 ligand 1 interacts specifically with the B7-1 costimulatory molecule to inhibit T cell responses" *Immunity* 27(1):111-22 (Jul. 2007).

Carter et al., "PD-1:PD-L inhibitory pathway affects both CD4(+) and CD8(+) T cells and is overcome by IL-2" *Eur J Immunol.* 32(3):634-43 (Mar. 2002).

Chambers et al., "CTLA-4-mediated inhibition in regulation of T cell responses: mechanisms and manipulation in tumor immunotherapy" *Annu Rev Immunol.* 19:565-94 (2001).

Chambers, "The expanding world of co-stimulation: the two-signal model revisited" *Trends Immunol.* 22(4):217-23 (Apr. 2001).

Chapoval et al., "B7-H3: a costimulatory molecule for T cell activation and IFN-gamma production" *Nat. Immunol.* 2(3):269-74 (Mar. 2001).

Chemnitz at al., "RNA fingerprints provide direct evidence for the inhibitory role of TGFbeta and PD-1 on CD4+ T cells in Hodgkin lymphoma" *Blood* 110(9):3226-33 (Nov. 2007).

Chen et al., "B7-H1 up-regulation on myeloid dendritic cells significantly suppresses T cell immune function in patients with chronic hepatitis B" *J Immunol.* 178(10):6634-41 (May 2007).

Chen et al., "0x40-ligand has a critical costimulatory role in dendritic cell:T cell interactions" *Immunity* 11(6):689-98 (Dec. 1999).

Choi et al., "Genomic organization and expression analysis of B7-H4, an immune inhibitory molecule of the B7 family" *J Immunol.* 171(9):4650-4654 (Nov. 1, 2003).

Cole et al., "The EBV-Hybridoma Technique and Its Application to Human Lung Cancer" *Monoclonal Antibodies and Cancer Therapy*, New York:Alan R. Liss, Inc. pp. 77-96 (1985).

Cooper et al., "4-1BB (CD137) controls the clonal expansion and survival of CD8 T cells in vivo but does not contribute to the development of cytotoxicity" *Eur J Immunol.* 32(2):521-9 (Feb. 2002).

Coussens et al., "Inflammation and Cancer" *Nature* 420:860-867 (Dec. 2002).

Coyle et al., "The CD28-related molecule ICOS is required for effective T cell-dependent immune responses" *Immunity* 13(1):95-105 (Jul. 2000).

Croft et al., "Co-stimulatory members of the TNFR family: keys to effective T-cell immunity?" *Nat Rev. Immunol.* 3(8):609-20 (Aug. 2003).

D'Souza et al., "Programmed death 1 expression on HIV-specific CD4+ T cells is driven by viral replication and associated with T cell dysfunction" *J Immunol.* 179(3):1979-87 (Aug. 2007).

Day et al., "PD-1 expression on HIV-specific T cells is associated with T-cell exhaustion and disease progression" *Nature* 443:350-4 (Sep. 2006).

De Smedt et al., "Ox40 costimulation enhances the development of T cell responses induced by dendritic cells in vivo" *J Immunol.* 168(2):661-70 (2002).

Debenedette et al., "Analysis of 4-1BB ligand (4-1BBL)-deficient mice and of mice lacking both 4-1BBL and CD28 reveals a role for 4-1BBL in skin allograft rejection and in the cytotoxic T cell response to influenza virus" *J Immunol.* 163(9):4833-41. (Nov. 1999).

Del Prete et al., "CD30-mediated signaling promotes the development of human T helper type 2-like T cells" *J Exp Med.* 182(6):1655-61 (Dec. 1995).

Ding and Shevach, "Activated B cells express CD28/B7-independent costimulatory activity" *J Immunol.* 157(4):1389-96 (Aug. 1996).

Ding et al., "B7H1-Ig fusion protein activates the CD4+ IFN-gamma receptor+ type 1 T regulatory subset through IFN-gamma-secreting Th1 cells" *J Immunol.* 177(6):3606-14 (Sep. 2006).

Dong et al., "B7-H1, a third member of the B7 family, co-stimulates T-cell proliferation and interleukin-10 secretion" *Nat Med.* 5(12):1365-9 (Dec. 1999).

Dong et al., "Cutting edge: critical role of inducible costimulator in germinal center reactions" *J. Immunol.* 166(6):3659-62 (Mar. 2001).

Dong et al., "ICOS co-stimulatory receptor is essential for T-cell activation and function" *Nature* 409:97-101 (Jan. 2001).

Dong et al., "Tumor-associated B7-H1 promotes T-cell apoptosis: a potential mechanism of immune evasion"*Nat Med.* 8(8):793-800 (Aug. 2002).

Dorfman et al., "Programmed death-1 (PD-1) is a marker of germinal center-associated T cells and angioimmunoblastic T-cell lymphoma" *Am J Surg Pathol.* 30(7):802-10 (Jul. 2006).

Dudley et al., "Cancer regression and autoimmunity in patients after clonal repopulation with antitumor lymphocytes" *Science* 298:850-4 (Oct. 2002).

Duhen et al., "LIGHT costimulates CD40 triggering and induces immunoglobulin secretion; a novel key partner in T cell-dependent B cell terminal differentiation" *Eur J Immunol.* 34(12):3534-41 (Dec. 2004).

Eppihimer et al., "Expression and regulation of the PD-L1 immunoinhibitory molecule on microvascular endothelial cells" *Microcirculation* 9(2):133-45 (Apr. 2002).

Ferrari et al., "Genetic aspects of osteoporosis" *Curr Opin Rheumatol.* 11(4):294-300 (Jul. 1999).

Freedman et al., "B7, a B-cell-restricted antigen that identifies preactivated B cells" *J Immunol.* 139(10):3260-7 (Nov. 1987).

Freeman et al., "Cloning of B7-2: a CTLA-4 counter-receptor that costimulates human T cell proliferation" *Science* 262:909-11 (Nov. 1993).

Freeman et al., "Engagement of the PD-1 immunoinhibitory receptor by a novel B7 family member leads to negative regulation of lymphocyte activation" *J Exp Med.* 192(7):1027-34 (Oct. 2000).

Freeman et al., "Murine B7-2, an alternative CTLA4 counter-receptor that costimulates T cell proliferation and interleukin 2 production" *J Exp Med.* 178(6):2185-92 (Dec. 1993).

Freeman et al., "Structure, expression, and T cell costimulatory activity of the murine homologue of the human B lymphocyte activation antigen B7" *Exp Med.* 174(3):625-31 (Sep. 1991).

Gajewski et al., "Immunization of HLA-A2+ melanoma patients with MAGE-3 or MelanA peptide-pulsed autologous peripheral blood mononuclear cells plus recombinant human interleukin 12" *Clin Cancer Res.* 7(3 Suppl):895s-901s (Mar. 2001).

Ganss et al., "Tumor microenvironment can restrict the effectiveness of activated antitumor lymphocytes" *Cancer Research* 58(20):4673-81 (Oct. 1998).

Gavrieli et al., "Characterization of phosphotyrosine binding motifs in the cytoplasmic domain of B and T lymphocyte attenuator required for association with protein tyrosine phosphatases SHP-1 and SHP-2" *Biophys Res Commun.* 312(4):1236-43 (Dec. 2003).

Geng et al., "B7-H1 expression is upregulated in peripheral blood CD14+ monocytes of patients with chronic hepatitis B virus infection, which correlates with higher serum IL-10 levels" *J Viral Hepat.* 13(11):725-33 (Nov. 2006).

Gonzalez et al., "A coreceptor interaction between the CD28 and TNF receptor family members B and T lymphocyte attenuator and herpesvirus entry mediator" *Proc. Natl. Acad. Sci. USA* 102:1116-1121 (2005).

Gramaglia et al., "The OX40 costimulatory receptor determines the development of CD4 memory by regulating primary clonal expansion" *J Immunol.* 165(6):3043-50 (Sep. 2000).

Greenwald and Freeman, "The B7 family revisited" *Annu Rev Immunol.* 23:515-48 (2005).

Greenwald et al., "CTLA-4 regulates induction of anergy in vivo" *Immunity* 14(2):145-55 (Feb. 2001).

Grimbacher et al., "Homozygous loss of ICOS is associated with adult-onset common variable immunodeficiency" *Nat Immunol.* 4(3):261-8 (Mar. 2003).

Gross et al., "Identification and distribution of the costimulatory receptor CD28 in the mouse" *J Immunol.* 149(2):380-8 (Jul. 1992).

Gross at al., "The murine homologue of the T lymphocyte antigen CD28. Molecular cloning and cell surface expression" *J Immunol.* 144(8):3201-10 (Apr. 1990).

Guinn et al., "4-1BBL cooperates with B7-1 and B7-2 in converting a B cell lymphoma cell line into a long-lasting antitumor vaccine" *J Immunol.* 162(8):5003-10 (Apr. 1999).

Ha et al., "Enhancing therapeutic vaccination by blocking PD-1-mediated inhibitory signals during chronic infection" *J Exp Med.* 205(3):543-55 (Mar. 2008).

Halstead et al., "In vivo stimulation of CD137 broadens primary antiviral CD8+ T cell responses" *Nat. Immunol.* 3(6):536-41 (Jun. 2002).

Hamanishi et al., "Programmed cell death 1 ligand 1 and tumor-infiltrating CD8+ T lymphocytes are prognostic factors of human ovarian cancer" *Proc Natl Acad Sci U S A.* 104(9):3360-5 (Feb. 2007).

Hamers-Casterman et al., "Naturally occurring antibodies devoid of light chains" *Nature* 363:446-448 (Jun. 3, 1993).

Harris, "Production of humanized monoclonal antibodies for in vivo imaging and therapy" *Biochemical Society Transactions* 23(4):1035-1038 (Nov. 1995).

Harrop et al., "Antibodies to TR2 (herpesvirus entry mediator), a new member of the TNF receptor superfamily, block T cell proliferation, expression of activation markers, and production of cytokines" *J Immunol.* 161(14):1786-94 (Aug. 1998).

Hathcock et al., "Comparative analysis of B7-1 and B7-2 costimulatory ligands: expression and function" *J Exp Med.* 180(2):631-40 (Aug. 1994).

Heckman et al., "Fast-tracked CTL: rapid induction of potent anti-tumor killer T cells in situ" *Eur J Immunol.* 37(7):1827-35 (Jul. 2007).

Hendriks et al., "CD27 is required for generation and long-term maintenance of T cell immunity" *Nat Immunol.* 1(5):433-40 (Nov. 2000).

Hintzen et al., "Engagement of CD27 with its ligand CD70 provides a second signal for T cell activation" *J Immunol.* 154(6):2612-23 (Mar. 1995).

Hirano et al., "Blockade of B7-H1 and PD-1 by monoclonal antibodies potentiates cancer therapeutic immunity" *Cancer Research* 65(3):1089-96 (Feb. 2005).

Hoogenboom and Winter, "By-passing immunisation. Human antibodies from synthetic repertoires of germline VH gene segments rearranged in vitro" *J Mol Biol.* 227(2):381-8 (Sep. 1992).

Hurle and Gross, "Protein Engineering Techniques for Antibody Humanization" *Curr Opin Biotechnol.* 5:428-433 (1994).

Hutloff et al., "ICOS is an inducible T-cell co-stimulator structurally and functionally related to CD28" *Nature* 397:263-6 (Jan. 1999).

Inman et al., "PD-L1 (B7-H1) expression by urothelial carcinoma of the bladder and BCG-induced granulomata: associations with localized stage progression" *Cancer* 109(8):1499-505 (Apr. 2007).

Iwai et al., "PD-1 inhibits antiviral immunity at the effector phase in the liver" *J Exp Med.* 198(1):39-50 (Jul. 2003).

Jenkins et al., "Antigen presentation by chemically modified splenocytes induces antigen-specific T cell unresponsiveness in vitro and in vivo." *J Exp Med.* 165(2):302-19 (Feb. 1987).

Johnson and Wu, "The Kabat Database and a Bioinformatics Example" *Methods in Molecular Biology*, Lo ed., Totowa, NJ:Human Press vol. 248:11-25 (2003).

Jones et al., "Replacing the Complementarity-Determining Regions in a Human Antibody with Those From a Mouse" *Nature* 321(6069):522-525 (May 29, 1986).

Jun et al., "B7-H1 (CD274) inhibits the development of herpetic stromal keratitis (HSK)" *FEBS Letters* 579(27):6259-64 (Nov. 2005).

Karandikar et al., "Targeting the B7/CD28:CTLA-4 costimulatory system in CNS autoimmune disease" *J Neuroimmunol.* 89:10-8 (Aug. 1998).

Keir et al., "PD-1 and its ligands in tolerance and immunity" *Annu Rev Immunol.* 26:677-704 (2008).

Konishi et al., "B7-H1 expression on non-small cell lung cancer cells and its relationship with tumor-infiltrating lymphocytes and their PD-1 expression" *Clin Cancer Res.* 10(15):5094-100 (Aug. 2004).

Kopf et al., "Inducible costimulator protein (ICOS) controls T helper cell subset polarization after virus and parasite infection" *J Exp Med.* 192(1):53-61 (Jul. 2000).

Kopf et al., "OX40-deficient mice are defective in Th cell proliferation but are competent in generating B cell and CTL Responses after virus infection" *Immunity* 11(6):699-708 (Dec. 1999).

Krummel et al., "CD28 and CTLA-4 have opposing effects on the response of T cells to stimulation" *J Exp. Med.* 182(2):459-65 (Aug. 1995).

Kuipers et al., "Contribution of the PD-1 ligands/PD-1 signaling pathway to dendritic cell-mediated CD4+ T cell activation" *Eur J Immunol.* 36(9):2472-82 (Sep. 2006).

Kuper et al., "Infections as a major preventable cause of human cancer" *J Intern Med.* 248(3):171-83 (Sep. 2000).

Kwon et al., "A Newly Identified Member of the Tumor Necrosis Factor Receptor Superfamily with a Wide Tissue Distribution and Involvement in Lymphocyte Activation" *Journal of Biological Chemistry* 272(22):14272-14276 (May 30, 1997).

Lafferty et al., "A new analysis of allogeneic interactions" *Aust J Exp Biol Med Sci.* 53(1):27-42 (Feb. 1975).

Lanzavecchia et al., "From TCR engagement to T celll activation: a kinetic view of T cell behavior" *Cell* 96(1):1-4 (Jan. 1999).

Latchman et al., "PD-L1-deficient mice show that PD-L1 on T cells, antigen-presenting cells, and host tissues negatively regulates T cells" *Proc Natl Acad Sci U S A.* 101(29):10691-6 (Jul. 2004).

Latchman et al., "PD-L2 is a second ligand for PD-1 and inhibits T cell activation" *Nat Immunol.* 2(3):261-8 (Mar. 2001).

Lee et al., "Interferon regulatory factor-1 is prerequisite to the constitutive expression and IFN-gamma-induced upregulation of B7-H1 (CD274)" *FEBS Letters* 580(3):755-62 (Feb. 2006).

Lenschow et al., "CD28/B7 System of T Cell Costimulation" *Annu. Rev. Immunol.* 14:233-258 (1996).

Li et al., "Human antibodies for immunotherapy development generated via a human B cell hybridoma technology" *Proc Natl Acad Sci U S A.* 103(10):3557-62 (Mar. 2006).

Liang et al., "Regulation of PD-1, PD-L1, and PD-L2 expression during normal and autoimmune responses" *Eur J Immunol.* 33(10):2706-16 (Oct. 2003).

Ling et al., "Duplication of primate and rodent B7-H3 immunoglobulin V- and C-like domains: divergent history of functional redundancy and exon loss" *Genomics* 82(3):365-77 (2003).

Linsley et al., "Coexpression and functional cooperation of CTLA-4 and CD28 on activated T lymphocytes" *J Exp Med.* 176(6):1595-604 (Dec. 1992).

Linsley et al., "Human B7-1 (CD80) and B7-2 (CD86) bind with similar avidities but distinct kinetics to CD28 and CTLA-4 receptors" *Immunity* 1(9):793-801 (Dec. 1994).

Linsley et al., "Intracellular trafficking of CTLA-4 and focal localization towards sites of TCR engagement" *Immunity* 4(6):535-43 (Jun. 1996).

Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway" *Blood* 110(1):296-304 (Jul. 2007).

Loke et al., "PD-L1 and PD-L2 are differentially regulated by Th1 and Th2 cells" *Proc Natl Acad Sci U S A.* 100(9):5336-41 (Apr. 2003).

Lucas et al., "Naive CD28-deficient T cells can initiate but not sustain an in vitro antigen-specific immune response" *J Immunol.* 154(11):5757-68 (Jun. 1995).

Mackensen et al., "Induction and large-scale expansion of CD8+ tumor specific cytotoxic T lymphocytes from peripheral blood lymphocytes by in vitro stimulation with CD80-transfected autologous melanoma cells" *Eur Cytokine Netw*. 10(3):329-36 (Sep. 1999).

Mages et al., "Molecular cloning and characterization of murine ICOS and identification of B7h as ICOS ligand" *Eur J Immunol*. 30(4):1040-7 (Apr. 2000).

Marincola et al., "Escape of human solid tumors from T-cell recognition: molecular mechanisms and functional significance" *Adv Immunol*. 74:181-273 (2000).

Marks et al., "By-Passing Immunization: Human Antibodies From V-gene Libraries Displayed on Phage" *J Mol. Biol*. 222(3):581-597 (Dec. 5, 1991).

Maxwell et al., "Danger and OX40 receptor signaling synergize to enhance memory T cell survival by inhibiting peripheral deletion" *J Immunol*. 164(1):107-12 (Jan. 2000).

McAdam et al., "ICOS is critical for CD40-mediated antibody class switching" *Nature* 409:102-5 (Jan. 2001).

McAdam et al., "Mouse inducible costimulatory molecule (ICOS) expression is enhanced by CD28 costimulation and regulates differentiation of CD4+ T cells" *J Immunol*. 165(9):5035-40 (Nov. 2000).

McAdam et al., "The role of B7 co-stimulation in activation and differentiation of CD4+ and CD8+ T cells" *Immunol Rev*. 165:231-47 (Oct. 1998).

Meidenbauer et al., "Survival and tumor localization of adoptively transferred Melan-A-specific T cells in melanoma patients" *J Immunol*. 170(4):2161-9 (Feb. 2003).

Melero et al., "Amplification of tumor immunity by gene transfer of the co-stimulatory 4-1BB ligand: synergy with the CD28 co-stimulatory pathway" *Eur J Immunol*. 28(3):1116-21 (Mar. 1998).

Melero et al., "Monoclonal Antibodies Against the 4-1BB T-cell Activation Molecule Eradicate Established Tumors" *Nature Medicine* 3(6):682-685 (Jun. 1997).

Mueller et al., "Viral targeting of fibroblastic reticular cells contributes to immunosuppression and persistence during chronic infection" *Proc Natl Acad Sci U S A*. 104(39):15430-5 (Sep. 2007).

Murata et al., "Constitutive OX40/OX40 ligand interaction induces autoimmune-like diseases" *J Immunol*. 169(8):4628-36 (Oct. 2002).

Murata et al., "Impairment of antigen-presenting cell function in mice lacking expression of OX40 ligand" *J Exp Med*. 191(2):365-74 (Jan. 2000).

Murphy et al., "Balancing co-stimulation and inhibition with BTLA and HVEM" *Nature Reviews/Immunology* 6:671-681 (2006).

Nakamura et al., "Reciprocal regulation of CD30 expression on CD4+ T cells by IL-4 and IFN-$\gamma$" *J Immunol*. 158(5):2090-8 (Mar. 1997).

Nakanishi et al., "Overexpression of B7-H1 (PD-L1) significantly associates with tumor grade and postoperative prognosis in human urothelial cancers" *Cancer Immunol Immunother*. 56(8):1173-82 (Aug. 2007).

Nguyen et al., "Cross-linking the B7 family molecule B7-DC directly activates immune functions of dendritic cells" *J Exp Med*. 196(10):1393-8 (Nov. 2002).

Nielsen et al., "Alternative splice variants of the human PD-1 gene" *Cellular Immunology* 235(2):109-16 (Jun. 2005).

Nishimura et al., "Autoimmune dilated cardiomyopathy in PD-1 receptor-deficient mice" *Science* 291:319-22 (Jan. 2001).

Nishimura et al., "Development of lupus-like autoimmune diseases by disruption of the PD-1 gene encoding an ITIM motif-carrying immunoreceptor" *Immunity* 11(2):141-51 (Aug. 1999).

Nishimura et al., "Developmentally regulated expression of the PD-1 protein on the surface of double-negative (CD4-CD8-) thymocytes" *Int Immunol*. 8(5):773-80 (May 1996).

Nomi et al., "Clinical significance and therapeutic potential of the programmed death-1 ligand/programmed death-1 pathway in human pancreatic cancer" *Clin Cancer Res*. 13(7):2151-7 (Apr. 2007).

Oshima et al, , "Characterization of murine CD70 by molecular cloning and mAb" *Int Immunol*. 10(4):517-26 (Apr. 1998).

Parsa et al., "Loss of tumor suppressor PTEN function increases B7-H1 expression and immunoresistance in glioma" *Nat Med*. 13(1):84-88 (Jan. 2007).

Peach et al., "Complementarity determining region 1 (CDR1)- and CDR3-analogous regions in CTLA-4 and CD28 determine the binding to B7-1" *J Exp Med*. 180(6):2049-58 (Dec. 1994).

Peterson et al., "Immunnization With Melan-A Peptide-Pulsed Peripheral Blood Mononuclear Cells Plus Recombinant Human Interleukin-12 Induces Clinical Activity and T-Cell Responses in Advanced Melanoma" *Journal of Clinical Oncology* 21(12):2342-2348 (2003).

Petrovas et al., "PD-1 is a regulator of virus-specific CD8+ T cell survival in HIV infection" *J Exp Med*. 203(10):2281-92 (Oct. 2006).

Prasad et al., "B7S1, a novel B7 family member that negatively regulates T cell activation" *Immunity* 18(6):863-873 (Jun. 2003).

Presta, "Antibody Engineering" *Current Opinion in Structural Biology* 2:593-596 (1992).

Radhakrishnan et al., "Blockade of allergic airway inflammation following systemic treatment with a B7-dendritic cell (PD-L2) cross-linking human antibody" *J Immunol*. 173(2) :1360-5 (Jul. 2004).

Radhakrishnan et al., "Dendritic cells activated by cross-linking B7-DC (PD-L2) block inflammatory airway disease" *J Allergy Clin Immunol*. (Retracted) 116(3):668-74 (Sep. 2005).

Radhakrishnan et al., "Immunotherapeutic potential of B7-DC (PD-L2) cross-linking antibody in conferring antitumor immunity" *Cancer Research* 64(14):4965-72 (Jul. 2004).

Radhakrishnan et al., "Naturally occurring human IgM antibody that binds B7-DC and potentiates T cell stimulation by dendritic cells" *J Immunol*. 170(4):1830-8 (Feb. 2003).

Riechmann et al., "Reshaping Human Antibodies for Therapy" *Nature* 332:323-327 (Mar. 24, 1988).

Rogers et al., "OX40 promotes Bcl-xL and Bcl-2 expression and is essential for long-term survival of CD4 T cells" *Immunity* 15(3):445-55 (Sep. 2001).

Rosenwald et al., "Molecular diagnosis of primary mediastinal B cell lymphoma identifies a clinically favorable subgroup of diffuse large B cell lymphoma related to Hodgkin lymphoma" *J Exp Med*. 198(6):851-62 (Sep. 2003).

Rottman et al., "The costimulatory molecule ICOS plays an important role in the immunopathogenesis of EAE" *Nat Immunol*. 2(7):605-11 (Jul. 2001).

Salomon et al., "Complexities of CD28/B7: CTLA-4 costimulatory pathways in autoimmunity and transplantation" *Annu Rev Immunol*. 19:225-52 (2001).

Sansom, "CD28, CTLA-4 and their ligands: who does what and to whom?" *Immunology* 101(2):169-77 (Oct. 2000).

Scheu et al., "Targeted disruption of LIGHT causes defects in costimulatory T cell activation and reveals cooperation with lymphotoxin beta in mesenteric lymph node genesis" *J Exp Med*. 195(12):1613-24 (Jun. 2002).

Schreiner et al., "Interferon-beta enhances monocyte and dendritic cell expression of B7-H1 (PD-L1), a strong inhibitor of autologous T-cell activation: relevance for the immune modulatory effect in multiple sclerosis" *J Neuroimmunol*. 155(1-2):172-82 (Oct. 2004).

Schultze et al., "B7-mediated costimulation and the immune response" *Blood Rev*. 10(2):111-27 (Jun. 1996).

Sedy et al., "B and T lymphocyte attenuator regulates T cell activation through interaction with herpesvirus entry mediator" *Nature Immunology* 6:90-98 (2005).

Segal et al., "An interleukin (IL)-10/IL-12 immunoregulatory circuit controls susceptibility to autoimmune disease" *J Exp Med*. 187(4):537-46 (Feb. 1998).

Seo et al., "Co-inhibitory role of T-cell-associated B7-H1 and B7-DC in the T-cell immune response" *Immunol Lett*. 102(2):222-8 (Feb. 2006).

Shahinian et al., "Differential T cell costimulatory requirements in CD28-deficient mice" *Science* 261:609-12 (Jul. 1993).

Sharpe and Freeman, "The B7-CD28 superfamily" *Nat Rev Immunol*. 2(2):116-26 (Feb. 2002).

Sheriff and Constantine, "Redefining the minimal antigen-binding fragment" *Nature Struct. Biol*. 3(9):733-736 (Sep. 1996).

Shimauchi et al., "Augmented expression of programmed death-1 in both neoplastic and non-neoplastic CD4+ T-cells in adult T-cell leukemia/lymphoma" *Int J Cancer* 121(12):2585-90 (2007).

Shin et al., "Cooperative B7-1/2 (CD80/CD86) and B7-DC costimulation of CD4+ T cells independent of the PD-1 receptor" *J Exp Med*. 198(1) :31-8 (Jul. 2003).

Sica et al., "B7-H4, a molecule of the B7 family, negatively regulates T cell immunity" *Immunity* 18(6):849-861 (Jun. 2003).

Sigal et al., "The role of B7-1 and B7-2 costimulation for the generation of CTL responses in vivo" *J. Immunol.* 161(6):2740-5 (Sep. 1998).

Singh et al.,, "Stroma is critical for preventing or permitting immunological destruction of antigenic cancer cells" *J Exp Med.* 175(1):139-46 (Jan. 1992).

Sloan-Lancaster et al., "Induction of T-cell anergy by altered T-cell-receptor ligand on live antigen-presenting cells" *Nature* 363:156-9 (May 1993).

Smith et al., "Schistosoma mansoni worms induce anergy of T cells via selective up-regulation of programmed death ligand 1 on macrophages" *J Immunol.* 173(2):1240-8 (Jul. 2004).

Sperling et al., "CD28/B7 interactions deliver a unique signal to naive T cells that regulates cell survival but not early proliferation" *J Immunol.* 157(9):3909-17 (Nov. 1996).

Sporici et al., "ICOS ligand costimulation is required for T-cell encephalitogenicity" *Clin Immunol.* 100(3):277-88 (Sep. 2001).

Steinberg et al., "A crucial role for HVEM and BTLA in preventing intestinal inflammation" *J Exp Med.* 205(6):1463-76 (Jun. 2008).

Steinberger et al., "Molecular characterization of human 4Ig-B7-H3, a member of the B7 family with four Ig-like domains" *J Immunol.* 172(4):2352-9 (Feb. 2004).

Strome et al., "B7-H1 blockade augments adoptive T-cell immunotherapy for squamous cell carcinoma" *Cancer Research* 63(19):6501-5 (Oct. 2003).

Stuart and Racke, "Targeting T cell costimulation in autoimmune disease" *Expert Opin. Ther. Targets* 6(3):275-89 (Jun. 2002).

Sun et al., "Characterization of mouse and human B7-H3 genes" *J Immunol.* 168(12):6294-7 (Jun. 2002).

Tafuri et al., "ICOS is essential for effective T-helper-cell responses" *Nature* 409:105-9 (Feb. 2001).

Takahashi et al., "Cutting edge: 4-1BB is a bona fide CD8 T cell survival signal" *J Immunol.* 162(9):5037-40 (May 1999).

Takahashi et al., "Differential clonal expansion of CD4 and CD8 T cells in response to 4-1BB ligation: contribution of 4-1BB during inflammatory responses" *Immunol Lett.* 76(3):183-91 (Apr. 2001).

Tamada et al., "LIGHT, a TNF-like molecule, costimulates T cell proliferation and is required for dendritic cell-mediated allogeneic T cell response" *J Immunol.* 164(8):4105-10 (Apr. 2000).

Tamada et al., "Modulation of T-cell-mediated immunity in tumor and graft-versus-host disease models through the LIGHT co-stimulatory pathway" *Nat Med.* 6(3):283-9 (Mar. 2000).

Tan et al., "4-1BB costimulation is required for protective anti-viral immunity after peptide vaccination" *J Immunol.* 164(5):2320-5 (Mar. 2000).

Tan et al., "4-1BB ligand, a member of the TNF family, is important for the generation of antiviral CD8 T cell responses" *J Immunol.* 163(9):4859-68 (Nov. 1999).

Terrazas et al., "Role of the programmed Death-1 pathway in the suppressive activity of alternatively activated macrophages in experimental cysticercosis" *Int J Parasitol.* 35(13):1349-58 (Nov. 2005).

Tesciuba et al., "Inducible costimulator regulates Th2-mediated inflammation, but not Th2 differentiation, in a model of allergic airway disease" *J Immunol.* 167(4):1996-2003 (Aug. 2001).

Tezuka et al., "Identification and characterization of rat AILIM/ICOS, a novel T-cell costimulatory molecule, related to the CD28/CTLA4 family" *Biochem Biophys Res Commun.* 276(1):335-45 (Sep. 2000).

Thompson et al., "CD28 activation pathway regulates the production of multiple T-cell-derived lymphokines/cytokines" *Proc Natl Acad Sci U S A.* 86(4):1333-7 (Feb. 1989).

Thompson et al., "Costimulatory B7-H1 in renal cell carcinoma patients: Indicator of tumor aggressiveness and potential therapeutic target" *Proc Natl Acad Sci U S A.* 101(49):17174-9 (Dec. 2004).

Trabattoni et al., "137-H1 is up-regulated in HIV infection and is a novel surrogate marker of disease progression" *Blood* 101(7):2514-20 (Apr. 2003).

Trautmann et al., "Upregulation of PD-1 expression on HIV-specific CD8+ T cells leads to reversible immune dysfunction" *Nat Med.* 12(10):1198-202 (Oct. 2006).

Tseng et al., "B7-DC, a new dendritic cell molecule with potent costimulatory properties for T cells" *J Exp Med.* 193(7):839-46 (Apr. 2001).

Ueda et al., "Association of the T-cell regulatory gene CTLA4 with susceptibility to autoimmune disease" *Nature* 423:505-11 (May 2003).

Urbani et al., "PD-1 expression in acute hepatitis C virus (HCV) infection is associated with HCV-specific CD8 exhaustion" *J Virol.* 80(22):11398-403 (Nov. 2006).

van Dijk and van de Winkel, "Human antibodies as next generation therapeutics" *Curr Opin Chem Biol.* 5(4):368-74 (Aug. 2001).

Vaswani and Hamilton, "Humanized antibodies as potential therapeutic drugs" *Ann Allergy Asthma & Immunol.* 1:105-115 (1998).

Velu et al., "Elevated expression levels of inhibitory receptor programmed death 1 on simian immunodeficiency virus-specific CD8 T cells during chronic infection but not after vaccination" *J Virol.* 81(11):5819-28 (2007).

Viola et al., "T cell activation determined by T cell receptor number and tunable thresholds" *Science* 273(5271):104-6 (Jul. 1996).

Walunas et al., "CTLA-4 Can Function as a Negative Regulator of T Cell Activation" *Immunity* 1(5):405-413 (Aug. 1994).

Walunas et al., "CTLA-4 ligation blocks CD28-dependent T cell activation" *J Exp Med.* 183(6):2541-50 (Jun. 1996).

Wan et al., "Aberrant regulation of synovial T cell activation by soluble costimulatory molecules in rheumatoid arthritis" *J Immunol.* 177(12):8844-50 (Dec. 2006).

Watanabe et al., "BTLA is a lymphocyte inhibitory receptor with similarities to CTLA-4 and PD-1" *Nat. Immunol.* 4(7):670-9 (Jun. 2003).

Weatherill et al., "OX40 ligation enhances cell cycle turnover of Ag-activated CD4 T cells in vivo" *Cellular Immunology* 209(1):63-75 (Apr. 2001).

Wherry et al., "Memory CD8 T-cell differentiation during viral infection" *J Virol.* 78(11):5535-45 (Jun. 2004).

Wu et al., "Immunohistochemical localization of programmed death-1 ligand-1 (PD-L1) in gastric carcinoma and its clinical significance" *Acta Histochem.* 108(1):19-24 (2006).

Xu and Davis, "Diversity in the CDR3 region of $V_H$ is sufficient for most antibody specificities" *Immunity* 13:37-45 (Jul. 2000).

Yamazaki et al., "Expression of programmed death 1 ligands by murine T cells and APC" *Immunol.* 169(10):5538-45 (Nov. 2002).

Ye et al., ."Modulation of LIGHT-HVEM costimulation prolongs cardiac allograft survival" *J Exp Med.* 195(6):795-800 (Mar. 2002).

Yokochi et al., "B lymphoblast antigen (BB-1) expressed on Epstein-Barr virus-activated B cell blasts, B lymphoblastoid cell lines, and Burkitt's lymphomas" *J Immunol.* 128(2):823-7 (Feb. 1982).

Yoshinaga et al., "T-cell co-stimulation through B7RP-1 and ICOS" *Nature* 402:827-32 (Dec. 1999).

Zang et al., "B7x: a widely expressed B7 family member that inhibits T cell activation" *Proc Natl Acad Sci U S A.* 100(18):10388-10392 (Sep. 2, 2003).

Zhang et al., "PD-1 up-regulation is correlated with HIV-specific memory CD8+ T-cell exhaustion in typical progressors but not in long-term nonprogressors" *Blood* 109(11):4671-8 (Jun. 2007).

Zhong et al., "PD-L2 expression extends beyond dendritic cells/macrophages to B1 cells enriched for V(H)11/V(H)12 and phosphatidylcholine binding" *Eur J Immunol.* 37(9):2405-10 (Sep. 2007).

Zou and Chen, "Inhibitory B7-family molecules in the tumour microenvironment" *Nat Rev Immunol.* 8(6):467-77 (Jun. 2008).

Zou et al., "Immunosuppressive networks in the tumour environment and their therapeutic relevance" *Nat Rev Cancer.* 5(4):263-74 (Apr. 2005).

Ochoa, Augusto C., "Mechanisms of Tumor Escape From the Immune Response" *Tumor Immunology and Immunotherapy Series*, Chapter 8 and 9, II:153-197 (2003).

Davies et al., "Affinity improvement of single antibody VH domains: residues in all three hypervariable regions affect antigen binding" *Immunotechnology* 2(3):169-179 (Sep. 1996).

Dong et al., "B7-H1 pathway and its role in the evasion of tumor immunity" *J. Mol. Med.* 81(5):281-287 (May 2003).

Shields, et al., "High resolution mapping of the binding site on human IgG1 for Fc gamma RI, Fc gamma RII, Fc gamma RIII, and FcRn and design of IgG1 variants with improved binding to the Fc gamma R" *Journal of Biological Chemistry* 276(9):6591-6604 (Mar. 2, 2001).

Wark et al., "Latest technologies for the enhancement of antibody affinity" *Advanced Drug Delivery Reviews* 58(5-6):657-670 (Aug. 2006).

\* cited by examiner

Heavy Chains

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 35B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | Chothia - CDR H1 | | | | Kabat - CDR H1 | | | | | | | | | | | | | | |
| | | | | | | | | | | | | | | | | | | | | | | | | | | | | | | | Contact - CDR H1 | | | | | | | | | | | | | | |
| Hu III Consensus | E | V | Q | L | V | E | S | G | G | G | L | V | Q | P | G | G | S | L | R | L | S | C | A | A | S | G | F | T | F | S | S | Y | A | M | S | - | - | W | V | R | Q | A | P | G | K |
| YW243.55.S70 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.H1 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.H12 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.H37 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.H70 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.H89 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.S1 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.5 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.8 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.30 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.34 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.S37 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.49 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.51 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.62 | E | V | Q | L | V | E | S | G | G | G | L | V | Q | P | G | G | S | L | R | L | S | C | A | A | S | G | F | T | F | S | D | S | W | I | H | - | - | W | V | R | Q | A | P | G | K |
| 243.55.84 | E | V | Q | L | V | E | S | G | G | G | L | V | Q | P | G | G | S | L | R | L | S | C | A | A | S | G | F | T | F | S | G | S | W | I | H | - | - | W | V | R | Q | A | P | G | K |
| | * | | | | | | | | | | | | | | | | | | | * | | | | * | | | | | | | | | | | | | | | * | | | * | | | |

FIG. 11A-2

Heavy Chains

| Kabat# | 44 | 45 | 46 | 47 | 48 | 49 | 50 | 51 | 52 | 52A | 52B | 52C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Hu III Consensus | G | L | E | W | V | S | V | I | S | G | - | - | - | D | G | G | S | T | Y | Y | A | D | S | V | K | G | R | F | T | I | S | R | D | N | S | K | N | T | A | Y | L | Q | M | N | S | L |
| YW243.55.S70 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.H1 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.H12 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.H37 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.H70 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.H89 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.S1 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.5 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.8 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.30 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.34 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.S37 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.49 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.51 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.62 | G | L | E | W | V | A | W | I | S | P | - | - | - | Y | G | G | S | T | Y | Y | A | D | S | V | K | G | R | F | T | I | S | A | D | T | S | K | N | T | A | Y | L | Q | M | N | S | L |
| 243.55.84 | G | L | E | W | V | A | W | I | L | P | - | - | - | Y | G | G | S | S | Y | Y | A | D | S | V | K | G | R | F | T | I | S | A | D | T | S | K | N | T | A | Y | L | Q | M | N | S | L |

Contact - CDR H2: positions 47–52
Chothia - CDR H2: positions 50–58
Kabat - CDR H2: positions 50–65

Heavy Chains

| Kabat# | 83 84 85 86 87 88 89 90 91 92 93 | 94 | 95 96 97 98 99 100 A B C D E F G H I J K | 101 102 103 | 104 105 106 | 107 108 109 110 111 112 113 |
|---|---|---|---|---|---|---|
| | | | Kabat - CDR H3 | | | |
| | | | Chothia - CDR H3 | | | |
| | | | Contact - CDR H3 | | | |
| Hu III Consensus | R A E D T A V Y Y C | A R | G - - - - - - - - - - - F D Y | W G Q | G T | L V T V S A |
| YW243.55.S70 | R A E D T A V Y Y C | A R | R H W P G G - - - - - - F D Y | W G Q | G T | L V T V S A |
| 243.55.H1 | R A E D T A V Y Y C | A R | R H W P G G - - - - - - F D Y | W G Q | G T | L V T V S A |
| 243.55.H12 | R A E D T A V Y Y C | A R | R H W P G G - - - - - - F D Y | W G Q | G T | L V T V S A |
| 243.55.H37 | R A E D T A V Y Y C | A R | R H W P G G - - - - - - F D Y | W G Q | G T | L V T V S A |
| 243.55.H70 | R A E D T A V Y Y C | A R | R H W P G G - - - - - - F D Y | W G Q | G T | L V T V S A |
| 243.55.H89 | R A E D T A V Y Y C | A R | R H W P G G - - - - - - F D Y | W G Q | G T | L V T V S A |
| 243.55.S1 | R A E D T A V Y Y C | A R | R H W P G G - - - - - - F D Y | W G Q | G T | L V T V S A |
| 243.55.5 | R A E D T A V Y Y C | A R | R H W P G G - - - - - - F D Y | W G Q | G T | L V T V S A |
| 243.55.8 | R A E D T A V Y Y C | A R | R H W P G G - - - - - - F D Y | W G Q | G T | L V T V S A |
| 243.55.30 | R A E D T A V Y Y C | A R | R H W P G G - - - - - - F D Y | W G Q | G T | L V T V S A |
| 243.55.34 | R A E D T A V Y Y C | A R | R H W P G G - - - - - - F D Y | W G Q | G T | L V T V S A |
| 243.55.S37 | R A E D T A V Y Y C | A R | R H W P G G - - - - - - F D Y | W G Q | G T | L V T V S A |
| 243.55.49 | R A E D T A V Y Y C | A R | R H W P G G - - - - - - F D Y | W G Q | G T | L V T V S A |
| 243.55.51 | R A E D T A V Y Y C | A R | R H W P G G - - - - - - F D Y | W G Q | G T | L V T V S A |
| 243.55.62 | R A E D T A V Y Y C | A R | R H W P G G - - - - - - F D Y | W G Q | G T | L V T V S A |
| 243.55.84 | R A E D T A V Y Y C | A R | R H W P G G - - - - - - F D Y | W G Q | G T | L V T V S A |
| | * * * | * | * | * | | |

FIG. 11A-3

| | |
|---|---|
| Hu III Consensus | SEQ ID NO:22 |
| YW243.55.S70 | SEQ ID NO:20 |
| 243.55.H1 | SEQ ID NO:23 |
| 243.55.H12 | SEQ ID NO:23 |
| 243.55.H37 | SEQ ID NO:23 |
| 243.55.H70 | SEQ ID NO:23 |
| 243.55.H89 | SEQ ID NO:23 |
| 243.55.S1 | SEQ ID NO:23 |
| 243.55.5 | SEQ ID NO:23 |
| 243.55.8 | SEQ ID NO:23 |
| 243.55.30 | SEQ ID NO:23 |
| 243.55.34 | SEQ ID NO:23 |
| 243.55.S37 | SEQ ID NO:23 |
| 243.55.49 | SEQ ID NO:23 |
| 243.55.51 | SEQ ID NO:23 |
| 243.55.62 | SEQ ID NO:23 |
| 243.55.84 | SEQ ID NO:24 |

Light Chains

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| HuKI | D | I | Q | M | T | Q | S | P | S | S | L | S | A | S | V | G | D | R | V | T | I | T | C | R | A | S | Q | S | I | S | N | Y | L | A | W | Y | Q |
| 243.55.S70 | D | I | Q | M | T | Q | S | P | S | S | L | S | A | S | V | G | D | R | V | T | I | T | C | R | A | S | Q | D | V | S | T | A | V | A | W | Y | Q |
| 243.55.H1 | D | I | Q | M | T | Q | S | P | S | S | L | S | A | S | V | G | D | R | V | T | I | T | C | R | A | S | Q | D | V | S | T | A | V | A | W | Y | Q |
| 243.55.H12 | D | I | Q | M | T | Q | S | P | S | S | L | S | A | S | V | G | D | R | V | T | I | T | C | R | A | S | Q | D | V | G | T | A | V | A | W | Y | Q |
| 243.55.H37 | D | I | Q | M | T | Q | S | P | S | S | L | S | A | S | V | G | D | R | V | T | I | T | C | R | A | S | Q | D | V | G | T | A | V | A | W | Y | Q |
| 243.55.H70 | D | I | Q | M | T | Q | S | P | S | S | L | S | A | S | V | G | D | R | V | T | I | T | C | R | A | S | Q | V | I | N | T | F | L | A | W | Y | Q |
| 243.55.H89 | D | I | Q | M | T | Q | S | P | S | S | L | S | A | S | V | G | D | R | V | T | I | T | C | R | A | S | Q | D | V | S | T | A | V | A | W | Y | Q |
| 243.55.S1 | D | I | Q | M | T | Q | S | P | S | S | L | S | A | S | V | G | D | R | V | T | I | T | C | R | A | S | Q | D | V | S | T | A | V | A | W | Y | Q |
| 243.55.5 | D | I | Q | M | T | Q | S | P | S | S | L | S | A | S | V | G | D | R | V | T | I | T | C | R | A | S | Q | D | V | S | T | A | V | A | W | Y | Q |
| 243.55.8 | D | I | Q | M | T | Q | S | P | S | S | L | S | A | S | V | G | D | R | V | T | I | T | C | R | A | S | Q | D | V | S | T | A | V | A | W | Y | Q |
| 243.55.30 | D | I | Q | M | T | Q | S | P | S | S | L | S | A | S | V | G | D | R | V | T | I | T | C | R | A | S | Q | D | V | G | T | A | V | A | W | Y | Q |
| 243.55.34 | D | I | Q | M | T | Q | S | P | S | S | L | S | A | S | V | G | D | R | V | T | I | T | C | R | A | S | Q | D | V | S | T | A | V | A | W | Y | Q |
| 243.55.S37 | D | I | Q | M | T | Q | S | P | S | S | L | S | A | S | V | G | D | R | V | T | I | T | C | R | A | S | Q | D | V | S | T | A | V | A | W | Y | Q |
| 243.55.49 | D | I | Q | M | T | Q | S | P | S | S | L | S | A | S | V | G | D | R | V | T | I | T | C | R | A | S | Q | D | V | S | T | A | V | A | W | Y | Q |
| 243.55.51 | D | I | Q | M | T | Q | S | P | S | S | L | S | A | S | V | G | D | R | V | T | I | T | C | R | A | S | Q | D | V | S | T | A | V | A | W | Y | Q |
| 243.55.62 | D | I | Q | M | T | Q | S | P | S | S | L | S | A | S | V | G | D | R | V | T | I | T | C | R | A | S | Q | D | V | S | T | A | V | A | W | Y | Q |
| 243.55.84 | * | * | * | * | * | * | * | * | * | * | * | * | * | * | * | * | * | * | * | * | * | * | * | * | * | * | * | * | * | * | * | * | * | * | * | * | * |

Kabat - CDR L1: positions 24–34
Chothia - CDR L1: positions 24–34
Contact - CDR L1: positions 30–36

*FIG. 11B-1*

Light Chains

| Kabat# | 38 39 40 41 42 43 44 45 46 47 48 49 50 51 52 53 54 55 56 57 58 59 60 61 62 63 64 65 66 67 68 69 70 71 72 73 74 75 76 77 78 79 80 |
|---|---|
| HuKI | Q K P G K A P K L L I Y A A S S L E S G V P S R F S G S G S G T D F T L T I S S L Q P |
| 243.55.S70 | Q K P G K A P K L L I Y S A S F L Y S G V P S R F S G S G S G T D F T L T I S S L Q P |
| 243.55.H1 | Q K P G K A P K L L I Y S A S F L Y S G V P S R F S G S G S G T D F T L T I S S L Q P |
| 243.55.H12 | Q K P G K A P K L L I Y S A S F L Y S G V P S R F S G S G S G T D F T L T I S S L Q P |
| 243.55.H37 | Q K P G K A P K L L I Y S A S F L Y S G V P S R F S G S G S G T D F T L T I S S L Q P |
| 243.55.H70 | Q K P G K A P K L L I Y S A S F L Y S G V P S R F S G S G S G T D F T L T I S S L Q P |
| 243.55.H89 | Q K P G K A P K L L I Y S A S F L A S G V P S R F S G S G S G T D F T L T I S S L Q P |
| 243.55.S1 | Q K P G K A P K L L I Y S A S F L Y S G V P S R F S G S G S G T D F T L T I S S L Q P |
| 243.55.5 | Q K P G K A P K L L I Y S A S F L Y S G V P S R F S G S G S G T D F T L T I S S L Q P |
| 243.55.8 | Q K P G K A P K L L I Y S A S F L Y S G V P S R F S G S G S G T D F T L T I S S L Q P |
| 243.55.30 | Q K P G K A P K L L I Y S A S F L Y S G V P S R F S G S G S G T D F T L T I S S L Q P |
| 243.55.34 | Q K P G K A P K L L I Y S A S F L Y S G V P S R F S G S G S G T D F T L T I S S L Q P |
| 243.55.S37 | Q K P G K A P K L L I Y S A S F L Y S G V P S R F S G S G S G T D F T L T I S S L Q P |
| 243.55.49 | Q K P G K A P K L L I Y S A S F L Y S G V P S R F S G S G S G T D F T L T I S S L Q P |
| 243.55.51 | Q K P G K A P K L L I Y S A S F L Y S G V P S R F S G S G S G T D F T L T I S S L Q P |
| 243.55.62 | Q K P G K A P K L L I Y S A S F L Y S G V P S R F S G S G S G T D F T L T I S S L Q P |
| 243.55.84 | * * * * * * * * * L I Y S A S F L Y S * * * * * * * * * * * * * * * * * * * * * * |

Kabat - CDR L2
Chothia - CDR L2
Contact - CDR L2

ANTI-PD-L1 ANTIBODIES, COMPOSITIONS AND ARTICLES OF MANUFACTURE

RELATED APPLICATIONS

This application claims the benefit of priority under 35 USC 119(e) of U.S. Provisional Application No. 61/121,092, filed 9 Dec. 2008, the disclosure of which is incorporated herein by reference in its entirety.

FIELD OF THE INVENTION

This invention relates generally to immune function and to enhancing T-cell function, including the upregulation of cell-mediated immune responses and to the treatment of T cell dysfunctional disorders.

BACKGROUND OF THE INVENTION

Co-stimulation or the provision of two distinct signals to T-cells is a widely accepted model of lymphocyte activation of resting T lymphocytes by antigen-presenting cells (APCs). Lafferty et al., *Aust. J. Exp. Biol. Med. Sci.* 53: 27-42 (1975). This model further provides for the discrimination of self from non-self and immune tolerance. Bretscher et al., *Science* 169: 1042-1049 (1970); Bretscher, P. A., *P.N.A.S. USA* 96: 185-190 (1999); Jenkins et al., *J. Exp. Med.* 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., *Ann. Rev. Immunol.* 14:233 (1996). In the absence of co-stimulation, T-cells can become refractory to antigen stimulation, do not mount an effective immune response, and further may result in exhaustion or tolerance to foreign antigens.

The simple two-signal model can be an oversimplification because the strength of the TCR signal actually has a quantitative influence on T-cell activation and differentiation. Viola et al., *Science* 273: 104-106 (1996); Sloan-Lancaster, *Nature* 363: 156-159 (1993). Moreover, T-cell activation can occur even in the absence of co-stimulatory signal if the TCR signal strength is high. More importantly, T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells.

The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting PD-1 and other molecules which signal through interactions with PD-1, such as programmed death ligand 1 (PD-L1) and programmed death ligand 2 (PD-L2) are an area of intense interest. The inhibition of PD-L1 signaling has been proposed as a means to enhance T cell immunity for the treatment of cancer (e.g., tumor immunity) and infection, including both acute and chronic (e.g., persistent) infection. However, as an optimal therapeutic directed to a target in this pathway has yet to be commercialized, a significant unmet medical need exists.

SUMMARY OF THE INVENTION

The present invention provides for anti-PD-L1 antibodies, including nucleic acid encoding and compositions containing such antibodies, and for their use to enhance T-cell function to upregulate cell-mediated immune responses and for the treatment of T cell dysfunctional disorders, including infection (e.g., acute and chronic) and tumor immunity.

In one embodiment, the invention provides for an isolated heavy chain variable region polypeptide comprising an HVR-H1, HVR-H2 and HVR-H3 sequence, wherein:

(a) the HVR-H1 sequence is GFTFSX$_1$SWIH; (SEQ ID NO: 1)

(b) the HVR-H2 sequence is AWIX$_2$PYGGSX$_3$YYADSVKG; (SEQ ID NO: 2)

(c) the HVR-H3 sequence is RHWPGGFDY; (SEQ ID NO: 3)

further wherein: $X_1$ is D or G; $X_2$ is S or L; $X_3$ is T or S. In one specific aspect, $X_1$ is D; $X_2$ is S and $X_3$ is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

HC-FR1 is EVQLVESGGGLVQPGGSLRLSCAAS (SEQ ID NO: 4)

HC-FR2 is WVRQAPGKGLEWV (SEQ ID NO: 5)

HC-FR3 is RFTISADTSKNTAYLQMNSLRAEDTAVYYCAR (SEQ ID NO: 6)

HC-FR4 is WGQGTLVTVSA. (SEQ ID NO: 7)

In a still further aspect, the heavy chain polypeptide is further combined with a variable region light chain comprising an HVR-L1, HVR-L2 and HVR-L3, wherein:

(a) the HVR-L1 sequence is RASQX$_4$X$_5$X$_6$TX$_7$X$_8$A; (SEQ ID NO: 8)

(b) the HVR-L2 sequence is SASX$_9$LX$_{10}$S; (SEQ ID NO: 9)

(c) the HVR-L3 sequence is QQX$_{11}$X$_{12}$X$_{13}$X$_{14}$PX$_{15}$T; (SEQ ID NO: 10)

further wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
                                         (SEQ ID NO: 11)
LC-FR1 is DIQMTQSPSSLSASVGDRVTITC (SEQ ID NO: 12)
LC-FR2 is WYQQKPGKAPKLLIY (SEQ ID NO: 13)
LC-FR3 is GVPSRFSGSGSGTDFTLTISSLQPEDFATYYC (SEQ ID NO: 14)
LC-FR4 is FGQGTKVEIKR.
```

In another embodiment, the invention provides an isolated anti-PD-L1 antibody or antigen binding fragment comprising a heavy chain and a light chain variable region sequence, wherein:
  (a) the heavy chain comprises and HVR-H1, HVR-H2 and HVR-H3, wherein further:

```
                                         (SEQ ID NO: 1)
(i)    the HVR-H1 sequence is GFTFSX₁SWIH;

(SEQ ID NO: 2)
(ii)   the HVR-H2 sequence is AWIX₂PYGGSX₃YYADSVKG (SEQ ID NO: 3)
(iii)  the HVR-H3 sequence is RHWPGGFDY,
and
```

(b) the light chain comprises and HVR-L1, HVR-L2 and HVR-L3, wherein further:

```
                                         (SEQ ID NOs: 8)
(i)    the HVR-L1 sequence is RASQX₄X₅X₆TX₇X₈A (SEQ ID NOs: 9)
(ii)   the HVR-L2 sequence is SASX₉LX₁₀S;
and (SEQ ID NOs: 10)
(iii)  the HVR-L3 sequence is QQX₁₁X₁₂X₁₃X₁₄PX₁₅T;
```

Further wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                         (SEQ ID NO: 4)
HC-FR1    EVQLVESGGGLVQPGGSLRLSCAAS (SEQ ID NO: 5)
HC-FR2    WVRQAPGKGLEWV (SEQ ID NO: 6)
HC-FR3    RFTISADTSKNTAYLQMNSLRAEDTAVYYCAR (SEQ ID NO: 7)
HC-FR4    WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                         (SEQ ID NO: 11)
LC-FR1    DIQMTQSPSSLSASVGDRVTITC (SEQ ID NO: 12)
LC-FR2    WYQQKPGKAPKLLIY (SEQ ID NO: 13)
LC-FR3    GVPSRFSGSGSGTDFTLTISSLQPEDFATYYC (SEQ ID NO: 14)
LC-FR4    FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, the invention provides for an anti-PD-L1 antibody comprising a heavy chain and a light chain variable region sequence, wherein:
  (a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, or
  (b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC- FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                          (SEQ ID NO: 4)
HC-FR1  EVQLVESGGGLVQPGGSLRLSCAAS (SEQ ID NO: 5)
HC-FR2  WVRQAPGKGLEWV (SEQ ID NO: 6)
HC-FR3  RFTISADTSKNTAYLQMNSLRAEDTAVYYCAR (SEQ ID NO: 7)
HC-FR4  WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                          (SEQ ID NO: 11)
LC-FR1  DIQMTQSPSSLSASVGDRVTITC (SEQ ID NO: 12)
LC-FR2  WYQQKPGKAPKLLIY (SEQ ID NO: 13)
LC-FR3  GVPSRFSGSGSGTDFTLTISSLQPEDFATYYC (SEQ ID NO: 14)
LC-FR4  FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, the invention provides for an isolated anti-PD-L1 antibody comprising a heavy chain and a light chain variable region sequence, wherein:

(a) the heavy chain sequence has at least 85% sequence identity to the heavy chain sequence: EVQLVESGGGLVQPGGSLRLSCAASGFTFSDSWIHWVRQAPGKGLEWVAWIS PYGGSTYYADSVKGRFTISADTSKNTAYLQMNSLRAEDTAVYYCARRHWPGGFDYWG QGTLVTVSA (SEQ ID NO:20), or (b) the light chain sequences has at least 85% sequence identity to the light chain sequence: DIQMTQSPSSLSASVGDRVTITCRASQDVSTAVAWYQQKPGKAPKWYSASF LYSGVPSRFSGSGSGTDFTLTISSLQPEDFATYYCQQYLHPATFGQGTKVEIKR (SEQ ID NO:21).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                          (SEQ ID NO: 4)
HC-FR1  EVQLVESGGGLVQPGGSLRLSCAAS (SEQ ID NO: 5)
HC-FR2  WVRQAPGKGLEWV (SEQ ID NO: 6)
HC-FR3  RFTISADTSKNTAYLQMNSLRAEDTAVYYCAR (SEQ ID NO: 7)
HC-FR4  WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                          (SEQ ID NO: 11)
LC-FR1  DIQMTQSPSSLSASVGDRVTITC (SEQ ID NO: 12)
LC-FR2  WYQQKPGKAPKLLIY (SEQ ID NO: 13)
LC-FR3  GVPSRFSGSGSGTDFTLTISSLQPEDFATYYC (SEQ ID NO: 14)
LC-FR4  FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region is IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, the invention provides for compositions comprising any of the above described anti-PD-L1 antibodies in combination with at least one pharmaceutically-acceptable carrier.

In a still further embodiment, the invention provides for isolated nucleic acid encoding a light chain or a heavy chain variable region sequence of an anti-PD-L1 antibody, wherein:
(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, and
(b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
EVQLVESGGGLVQPGGSLRLSCAAS          (SEQ ID NO: 4)

HC-FR2
WVRQAPGKGLEWV                      (SEQ ID NO: 5)

HC-FR3
RFTISADTSKNTAYLQMNSLRAEDTAVYYCAR   (SEQ ID NO: 6)

HC-FR4
WGQGTLVTVSA.                       (SEQ ID NO: 7)
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
DIQMTQSPSSLSASVGDRVTITC            (SEQ ID NO: 11)

LC-FR2
WYQQKPGKAPKLLIY                    (SEQ ID NO: 12)

LC-FR3
GVPSRFSGSGSGTDFTLTISSLQPEDFATYYC   (SEQ ID NO: 13)

LC-FR4
FGQGTKVEIKR.                       (SEQ ID NO: 14)
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, the nucleic acid further comprises a vector suitable for expression of the nucleic acid encoding any of the previously described anti-PD-L1 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

In a still further embodiment, the invention provides for a process of making an anti-PD-L1 antibody or antigen binding fragment thereof, comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

In a still further embodiment, the invention provides for a composition comprising an anti-PD-L1 antibody or antigen binding fragment thereof as provided herein and at least one pharmaceutically acceptable carrier.

In a still further embodiment, the invention provides an article of manufacture comprising a container enclosing a therapeutically effective amount of a composition disclosed herein and a package insert indicating use for the treatment of a T-cell dysfunctional disorder.

In a still further embodiment, the invention provides for an article of manufacture comprising any of the above described anti-PD-L1 compositions in combination with at least one BNCA molecules. In one aspect, the BNCA molecules is an antibody, antigen binding antibody fragment, BNCA oligopeptide, BNCA RNAi or BNCA small molecule. In another aspect, the B7 negative costimulatory molecule is selected from the group consisting of: CTLA-4, PD-1, PD-L1, PD-L2, B7.1, B7-H3 and B7-H4.

In a still further embodiment, the article of manufacture comprises any of the above described anti-PD-L1 compositions in combination with a chemotherapeutic agent. In one aspect, the chemotherapeutic agent is gemcitabine.

In a still further embodiment, the invention provides for an article of manufacture comprising any of the above described anti-PD-L1 antibodies in combination with one or more agonists of a positive costimulatory molecule. In one aspect, a positive costimulatory molecule is a B7 family costimulatory molecule. In another aspect the positive costimulatory molecule is selected from the group consisting of: CD28, CD80, CD86, ICOS/ICOSL. In yet another aspect, the positive costimulatory molecule is a TNFR family costimulatory molecule. In a further aspect, the TNFR costimulatory molecule is selected form the group consisting of: OX40/OX40L, 4-1BB/4-1BBL, CD27/CD27L, CD30/CD30L and HVEM/LIGHT, and soluble fragments, constructs and agonist antibodies thereof.

In a still further embodiment, the invention provides for an article of manufacture comprising any of the above described anti-PD-L1 antibodies in combination with one or more antibiotics. In one aspect, the antibiotic is selected from the group consisting of an anti-viral agent, anti-bacterial agent, anti-fungal agent, anti-protozoan agent.

In another aspect the anti-viral agent is selected from the group consisting of reverse transcriptase inhibitors, protease inhibitors, integrase inhibitors, entry or fusion inhibitors, maturation inhibitors, viral release inhibitors, immune response enhancers, anti-viral synergistic enhancers, vaccines, hepatic agonists and herbal therapies. In yet another aspect, the combination comprises one or more categories of anti-viral agents.

In a still further embodiment, the invention provides for an article of manufacture comprising any of the above described anti-PD-L1 antibodies in combination with one or more vaccines.

In a still further embodiment, the invention provides for a method of enhancing T-cell function comprising administering an effective amount of any of the above described anti-PD-L1 antibodies or compositions. In one aspect, the anti-PD-L1 antibody or composition renders dysfunctional T-cells non-dysfunctional.

In a still further embodiment, the invention provides for a method of treating a T-cell dysfunctional disorder comprising administering a therapeutically effective amount of any of the above described anti-PD-L1 antibodies or compositions. In one specific aspect, the T-cell dysfunctional disorder is infection or tumor immunity. In another aspect the infection is acute or chronic. In another aspect, the chronic infection is persistent, latent or slow. In yet another aspect, the chronic infection results from a pathogen selected from the group consisting of bacteria, virus, fungi and protozoan. In a further aspect, the pathogen level in the host is reduced.

In a still further aspect, the method further comprises treatment with a vaccine. In a still further aspect, the method further comprises treatment with an antibiotic. In a still further aspect, the pathogen is a bacteria, and the method further comprises the administration of an antibacterial agent. In a still further aspect, the bacteria is selected from the group consisting of: *Mycobacterium* spp., *Salmonella* spp., *Listeria* spp., *Streptococcus* spp., *Haemophilus* spp., *Neisseria* spp., *Klebsiella* spp., *Borrelia* spp., *Bacterioides fragillis, Treponema* spp., and *Helicobacter pylori*. In a still further aspect, the pathogen is a virus, and the method further comprises the administration of an anti-viral agent. In a still further aspect, the virus is selected from the group consisting of: hepatitis-B, -C, herpes simplex virus-I, -II, human immunodeficiency virus-I, -II, cytomegalovirus, Eppstein Barr virus, human papillomavirus, human T lymphotrophic viruses,-I, -II, varicella zoster. In a still further aspect, the pathogen is a fungus, and the method further comprises the administration of an anti-fungal agent. In a still further aspect, the disorder is selected from the group consisting of: aspergilosis, blastomycosis, candidiasis albicans, coccidioiodmycosis immitis, histoplasmosis, paracoccidioiomycosis, microsporidiosis. In a still further aspect, the pathogen is a protozoan, and the method further comprises the administration of an anti-protozoan agent. In a still further aspect, the disorder is selected from the group consisting of: leishmaniasis, plasmodiosis (i.e., malaria), cryptosporidiosis, toxoplasmosis, trypanosomiasis, and helminth infections, including those resulting from trematodes (e.g., schistosomiasis), cestodes (e.g., echinococcosis) and nemotodes (e.g., trchinosis, ascariasis, filariosis and strongylodiosis).

In a still further aspect, the T-cell dysfunctional disorder is tumor immunity. In a still further aspect, the PD-L1 antibody or composition is combined with a treatment regimen further comprising a traditional therapy selected from the group consisting of: radiation therapy, chemotherapy, targeted therapy, immunotherapy, hormonal therapy, angiogenesis inhibition and palliative care. In a still further specific aspect, the chemotherapy treatment is selected from the group consisting of: gemcitabine, cyclophosphamide, doxorubicin, paclitaxel, cisplatin. In a still further specific aspect, the tumor immunity results from a cancer selected from the group consisting of: breast, lung, colon, ovarian, melanoma, bladder, kidney, liver, salivary, stomach, gliomas, thyroid, thymic, epithelial, head and neck cancers, gastric, and pancreatic cancer.

BRIEF DESCRIPTION OF THE DRAWINGS

In FIG. 8A, viral titers from the various indicated tissues are analyzed at Days 21 and 28, one and two weeks after Ab treatment, respectively. In FIG. 8B, serum viral titers are analyzed on Days 0, 7, 14, 21 and 28, with LCMV inoculation occurring on day 0 and treatment commencing on day 14.

FIGS. 11A-B are the heavy and light chain variable region sequences, respectively, of 11 anti-PD-L1 antibodies identified by phage display. The shaded bars show CDRs with various definitions, while the boxed areas show the extent of the HVRs.

DETAILED DESCRIPTION OF THE PREFERRED EMBODIMENT

Figure 1:
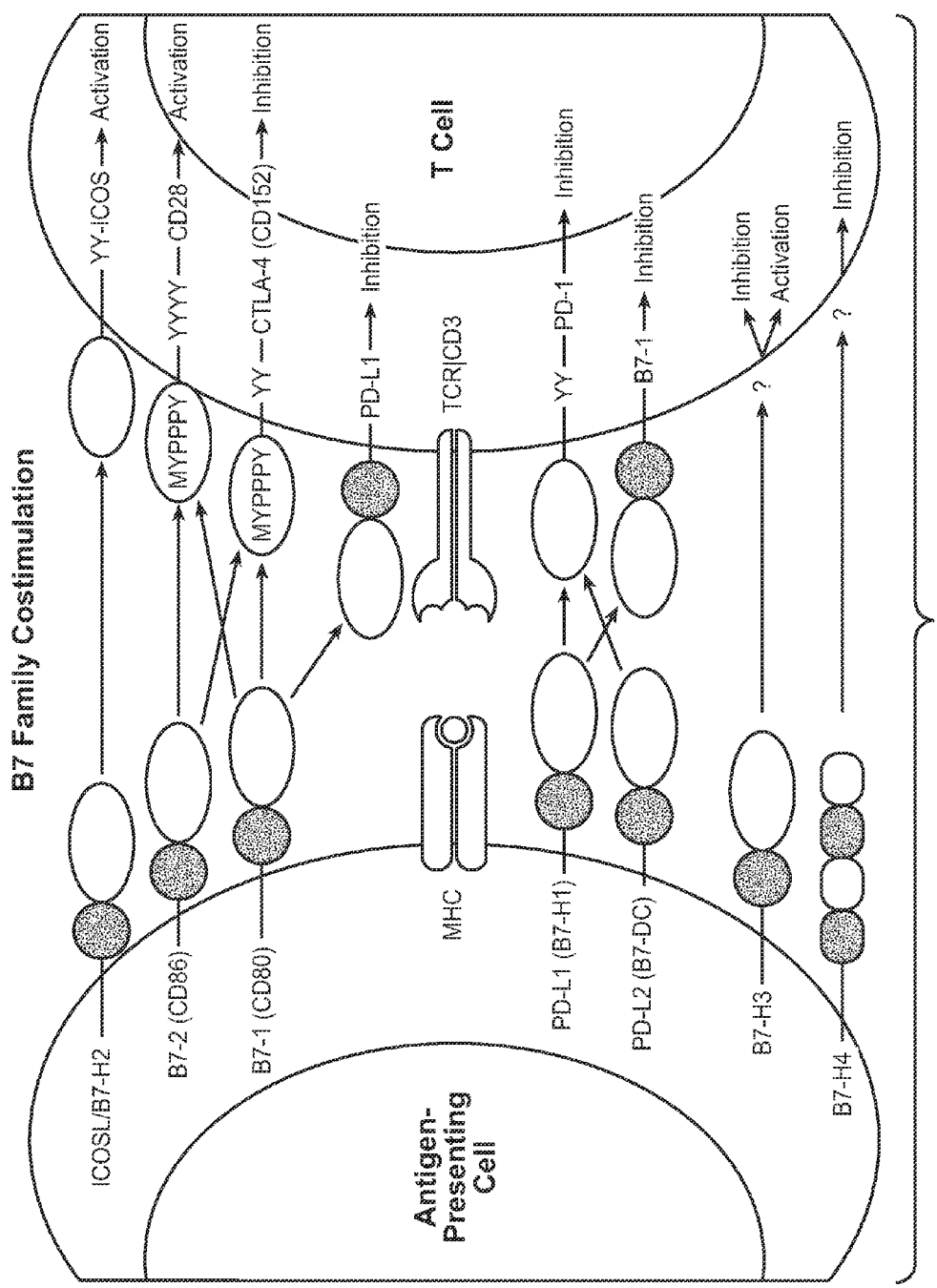
FIG. 1 is a graphical illustration depicting costimulation of T-cells by the B7 family of cell surface molecules.
Figure 2:
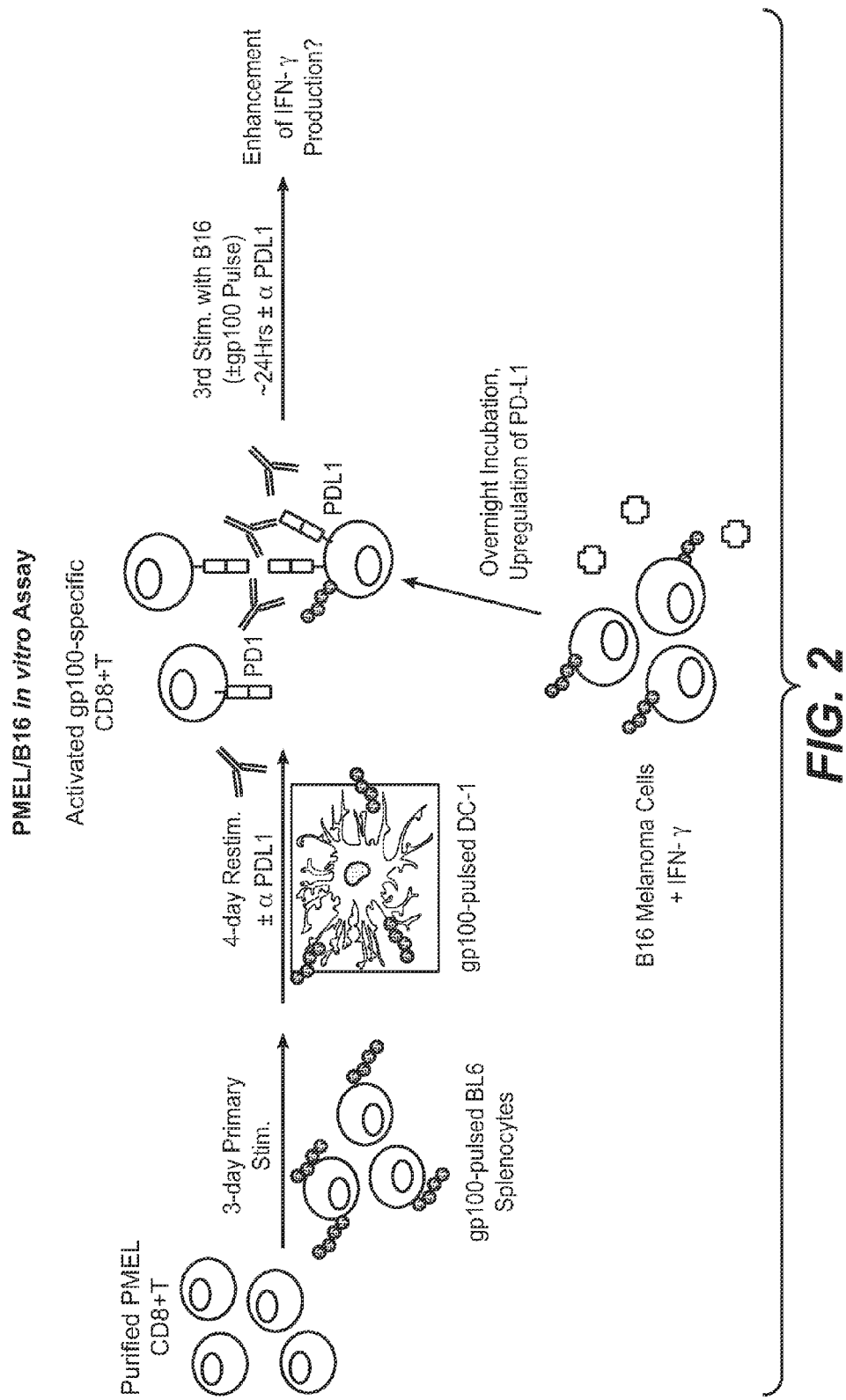
FIG. 2 is a schematic showing the experimental design of the PMEL/B16 T-cell stimulation assay.

All references mentioned herein are specifically incorporated by reference.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds 1987, and periodic updates); *PCR: The Polymerase Chain Reaction*, (Mullis et al., ed., 1994); *A Practical Guide to Molecular Cloning* (Perbal Bernard V., 1988); *Phage Display: A Laboratory Manual* (Barbas et al., 2001).

I. Host Immunity

A. Lymphocyte Development and Activation

The two major types of lymphocytes in humans are T (thymus-derived) and B (bone marrow derived. These cells are derived from hematopoietic stem cells in the bone marrow and fetal liver that have committed to the lymphoid development pathway. The progeny of these stem cells follow divergent pathways to mature into either B or T lymphocytes. Human B-lymphocyte development takes place entirely within the bone marrow. T cells, on the other hand, develop from immature precursors that leave the marrow and travel through the bloodstream to the thymus, where they proliferate and differentiate into mature T lymphocytes.

Mature lymphocytes that emerge from the thymus or bone marrow are in a quiescent, or "resting" state, i.e., they are mitotically inactive. When dispersed into the bloodstream, these "naïve" or "virgin" lymphocytes, travel into various secondary or peripheral lymphoid organs, such as the spleen, lymph nodes or tonsils. Most virgin lymphocytes have an inherently short life span and die without a few days after leaving the marrow or thymus. However, if such a cell receives signals that indicate the presence of an antigen, they may activate and undergo successive rounds of cell division. Some of the resulting progeny cells then revert to the resting state to become memory lymphocytes—B and T cells that are essentially primed for the next encounter with the stimulating allergen. The other progeny of activated virgin lymphocytes are effector cells, which survive for only a few days, but carry out specific defensive activities.

Lymphocyte activation refers to an ordered series of events through which a resting lymphocyte passes as it is stimulated to divide and produce progeny, some of which become effector cells. A full response includes both the induction of cell proliferation (mitogenesis) and the expression of immunologic functions. Lymphocytes become activated when specific ligands bind to receptors on their surfaces. The ligands are different for T cells and B cells, but the resulting intracellular physiological mechanisms are similar.

Some foreign antigens themselves can induce lymphocyte activation, especially large polymeric antigens that cross-link surface immunoglobulins on B-cells, or other glycoproteins on T-cells. However, most antigens are not polymeric and even direct binding to B-cells in large numbers fail to result in activation. These more common antigens activate B cells when they are co-stimulated with nearby activated helper T-lymphocytes. Such stimulation may occur from lymphokines secreted by the T-cell, but is transmitted most efficiently by direct contact of the B cell with T-cell surface proteins that interact with certain B-cell surface receptors to generate a secondary signal.

B. T-cells

T lymphocytes do not express immunoglobulins, but, instead detect the presence of foreign substances by way of surface proteins called T-cell receptors (TCR). These receptors recognize antigens by either direct contact or through influencing the activity of other immune cells. Together with macrophages, T cells are the primary cell type involved in the cell-mediated immunity.

Unlike B-cells, T-cells can detect foreign substances only in specific contexts. In particular, T-lymphocytes will recognize a foreign protein only if it first cleaved into small peptides, which are then displayed on the surface of a second host cell, called an antigen-presenting cell (APC). Many types of host cells can present antigens under some conditions but certain types are more specifically adapted for this purpose and are particularly important in controlling T-cell activity, including macrophages and other B-cells. Antigen presentation depends in part on specific proteins, called major histocompatibility complex (MHC) proteins, on the surface of the presenting cells. Thus, to stimulate cell-mediated immunity, foreign peptides must be presented to T-cells in combination with MHC peptides, and this combination must be recognized by a T-cell receptor.

There are two significant T-cell subsets: cytotoxic T lymphocytes ($T_C$ cells or CTLs) and helper T cells ($T_H$) cells, which can roughly be identified on the basis of cell surface expression of the marker CD8 and CD4. $T_c$ cells are important in viral defense, and can kill viruses directly by recognizing certain cell surface expressed viral peptides. $T_H$ cells promote proliferation, maturation and immunologic function of other cell types, e.g., lymphokine secretion to control activities of B cells, macrophages and cytotoxic T cells. Both virgin and memory T-lymphocytes ordinarily remain in the resting state, and in this state they do not exhibit significant helper or cytotoxic activity. When activated, these cells undergo several rounds of mitotic division to produce daughter cells. Some of these daughter cells return to the resting state as memory cells, but others become effector cells that actively express helper or cytotoxic activity. These daughter cells resemble their parents: CD4+ cells can only product CD4+ progeny, while CD8+ cells yield only CD8+ progeny. Effector T-cells express cell surface markers that are not expressed on resting T-cells, such as CD25, CD28, CD29, CD40L, transferrin receptors and class II MHC proteins. When the activating stimuli is withdrawn, cytotoxic or helper activity gradually subsides over a period of several days as the effector cells either die or revert to the resting state.

Similar to B-cell activation, T-lymphocyte responses to most antigens also require two types of simultaneous stimuli. The first is the antigen, which if appropriately displayed by MHC proteins on an antigen-presenting cell, can be recognized and bound by T-cell receptors. While this antigen-MHC complex does send a signal to the cell interior, it is usually insufficient to result in T-cell activation. Full activation, such as occurs with helper T-cells, requires costimulation with other specific ligands called costimulators that are expressed on the surface of the antigen-presenting cell. Activation of a cytotoxic T cell, on the other hand, generally requires IL-2, a cytokine secreted by activated helper T cells.

C. The Immune Response

The three primary functional properties of the mammalian immune system distinguishing it from the other body's defenses include: (1) specificity—the ability to recognize and respond or not to respond individually among a vast number of target molecules, (2) discrimination—the ability to determine self from non-self so as to peacefully coexist with all the innumerable proteins and other organic material, yet still respond vigorously against foreign material that is introduced to the body, and (3) memory—the ability to be molded by experience such that subsequent encounters with a particular foreign pathogen will provoke a more rapid and vigorous response than what occurred at the initial encounter. When one or more of these functions is frustrated, a pathological condition results.

Virgin lymphocytes are continually released from the primary lymphoid organs into the periphery, each carrying surface receptors that enable antigen binding. Antigen binding in B cells is mediated through surface-bound immunoglobulins, whereas in T-cells it is mediated by T-cell receptors. When virgin lymphocytes are activated, they proliferate, yielding daughter cells that may then undergo further cycles of activation and proliferation. The speed and intensity of response to a given antigen is determined largely by clonal selection: the larger the population of daughter cells or clones specific to a particular antigen, the greater the number of cells that can recognize and participate in the immune response. Every immune response is complex and intricately regulated sequence of events involving several cell types. It is triggered when an immunogen enters the body and encounters a specialized class of cells called antigen-presenting cells (APCs). These APCs capture a minute amount of the immunogen and display it in a form that can be recognized by antigen-specific helper T-lymphocytes. The helper T cells then become activated and, in turn, promote activation of other classes of lymphocytes, such as B cells or cytotoxic T cells. The activated lymphocytes then proliferate and carry out their specific effector functions. At each stage in this process, the lymphocytes and APCs communicate with one another through direct contact or by secreting regulatory cytokines.

Exogenous antigens that are captured by an APC undergo a series of alterations called antigen processing. Such processing, especially of proteinaceous immunogens involves denaturation and partial proteolytic digestions, so that the immunogen is cleaved into short peptides. A limited number of the resulting peptides then associated non-covalently with class II MHC proteins and are transported to the APC surface, a process known as antigen presentation. A CD4+ helper T lymphocyte that comes into direct contact with an APC may become activated, but it will do so only if it expressed a T-cell receptor protein that can recognize and bind the particular peptide-MHC complex presented by the APC.

Helper T ($T_H$) cells are the principal orchestrators of the immune response because they are needed for activation of the two other lymphatic effector cells: cytotoxic T (Tc) cells and antibody secreting plasma cells. $T_H$ activation occurs early in an immune response and requires at least two signals. One signal is provided by binding of the T-cell antigen receptor to the antigenic peptide-MHC complex on the APC surface that is transmitted through the CD3 protein complex, while the second, costimulatory signal through the APC is thought to result from binding of a separate signal-transmitting protein on the T-cell surface with a specific ligand on the APC. One known such interaction is the T-cell protein CD28 and the family of APC surface proteins known as B7. Other surface proteins pairs may also mediate costimulation. The process of co-stimulation is described in greater detail subsequently. The anti-PD-L1 antibodies of the present invention are believed to enhance co-stimulation through antagonism of a negative costimulatory signal provided by signaling through PD-L1.

Together, the two signals induce the helper T cell to begin secreting the cytokine interleukin-2 (IL-2) and also to begin expressing specific high affinity IL-2 receptors on its surface. IL-2 is a highly potent mitogenic factor for T-lymphocytes and is essential for the proliferative response of activated T-cells. The effect of IL-2 on the cell from which it is secreted—a phenomenon known as an autocrine effect. It has further been shown that even if a T-cell has received both signals, it will not proliferate if its own surface IL-2 receptors are blocked. IL-2 can also act on cells in the immediate vicinity, in a so-called paracrine effect. This effect is especially important to activate Tc cells, which generally do not produce enough IL-2 to stimulate their own proliferation. In addition to IL-2, activated $T_H$ cells secrete other cytokines and promote the growth, differentiation, and functions of B-cells, macrophages and other cell types.

The contact between an APC and an antigen-specific $T_H$ cell also has effect on the APC—one of the most important of which is the release of IL-1. This cytokine is believed to act in an autocrine manner to increase surface expression of class II MHC proteins and of various adhesion molecules thereby strengthening the binding of the $T_H$ cell and enhancing antigen presentation. At the same time, IL-1 functions in a paracrine manner on the $T_H$ cell to promote IL-2 secretion and IL-2 receptor expression.

During activation of $T_H$ cells in the manner previously described, some B-cells may also have been engaging the immunogen through their antigen receptors, which are membrane-bound forms of the antibodies that they will later secrete. Unlike T-cells, B-cells recognize an immunogen in its free, unprocessed form. Specific antigen binding provides one type of signal that can lead to B-cell activation. A second type is provided by activated $T_H$ cells, which express proteins that help activate the B cell by binding to non-immunoglobulin receptors on its surface. These $T_H$-derived signals, which act on any B cell regardless of its antigen specificity, are known as helper factors. These helper factors include IL-2, IL-4 and IL-6. However, help is more efficiently achieved through cell-cell contact, which allows proteins on the T-cell surface to directly contact those on the B cell. The most effect form of contact-mediated help occurs when a protein called CD40 ligand (CD40L), which is expressed on $T_H$ cells only after they become activated, binds to a protein called CD40 on B cells. In a process known as by-stander activation, contact with an activated B cell can even be sufficient to activate resting B cells even though its surface immunoglobulins have not engaged in antigen.

$T_c$ lymphocytes function to eradicate cells that express foreign antigens on their surfaces, such as virus-infected host cells. Most $T_c$ cells express CD8 rather than CD4 and hence recognize antigens in association with class I rather than class II MHC proteins. When a somatic cell is infected by a virus, some immunogenic viral proteins may undergo processing within the cell, and the resulting peptides may then appear as surface complexes with class I MHC molecules. These peptide-MHC complexes may then be recognized by the T-cell receptor of an antigen-specific clone, providing one of two signals necessary for $T_c$-cell activation. This first signal alone induces high-affinity IL-2 receptors on the $T_c$ cell. The second signal is furnished by IL-2 secreted from a nearby activated $T_H$ lymphocyte. On receiving both signals, the activated $T_c$ cell acquires cytotoxic activity, enabling it to kill the cell to which it is bound, as well as any other cells bearing the same peptide-MHC class I complexes. In some cases, killing occurs because the $T_c$ releases specific toxins onto the target cell; in others, the $T_c$ induces the target cell to commit suicide by apoptosis. The activated $T_c$ cell also proliferates, giving rise to additional $T_c$ cells with the same antigen specificity.

D. Co-stimulation by the Immunoglobulin Superfamily

1. B7.1/B7.2-CD28/CTLA-4

Perhaps the best characterized T-cell costimulatory pathway is the one that signals through B7.1(CD80)/B7.2(CD86)-CD28/CTLA-4(CD152). This signaling pathway is critical to T-cell activation and tolerance. Karandikar et al., *J. Neuroimmunol.* 89: 10-18 (1998); Oosterwegal et al., *Curr. Opin. Immunol.* 11: 294-300 (1999); Salomon et al., *Annu. Rev. Immunol.* 19: 225-252 (2001); Sansom, D. M., *Immunol.* 101: 169-177 (2000); Chambers et al., *Annu. Rev. Immunol.* 19: 565-592 (2001).

B7.1 [Freeman et al., *J. Exp. Med.* 174: 625-631 (1991); Freedman et al., *J. Immunol.* 137: 3260-3267 (1987); Yokochi et al., *J. Immunol.* 128: 823-827 (1982)] and B7.2 [Freeman et al., *Science* 262: 909-911 (1993); Freeman et al., *J. Exp. Med.* 178: 2185-2192 (1993); Azuma et al., *Nature* 366: 76-79 (1993)] have dual specificity for the two stimulatory receptors CD-28 and CTLA-4. Aruffo et al., *Proc. Natl. Acad. Sci. USA* 84: 8573-8577 (1987); Gross et al., *J. Immunol.* 144: 3201-3210 (1990). CD28 is constitutively expressed on the surface of T cells [Gross et al., *J. Immunol.* 149: 380-388 (1992)], while CTLA-4, the higher affinity receptor, has expression that is rapidly upregulated following T-cell activation. Peach et al., *J. Exp. Med.* 180: 2049-2058 (1994); Linsley et al., *J. Exp. Med.* 176: 1595-1604 (1992); Kinsley et al., *Immunity* 1: 793-801 (1994); Linsley et al., *Immunity* 4: 535-543 (1996). Most APC populations express B7.2 constitutively at low levels, which is rapidly upregulated, while B7.1 is inducibly expressed later after activation. Freeman et al., *Science* 262: 909-911 (1993); Hathcock et al., *J. Exp. Med.* 180: 631-640 (1994). The prior expression of B7.2 and mouse knock-out data suggest that B7.2 is the more important co-stimulatory molecule for initiating immune responses, but otherwise the two molecules have largely overlapping functions. McAdam et al., *Immuno. Rev.* 165: 631-640 (1994).

CD28 intereacts with B7.1 and B7.2 to transmit a signal that synergizes with the TCR signal to promote T-cell activation. Lenschow et al., *Annu. Rev. Immunol.* 165: 233-258 (1996); Lanzavecchia et al., *Cell* 96: 1-4 (1999). In the absence of a TCR signal, CD28 signaling does not have physiological significance. CD28 signaling regulates the threshold for T-cell activation and significantly decreases the number of TCR engagements needed for T-cell activation. Viola et al., *Science* 273: 104-106 (1996). CD28 activation sustains T-cell responses by promoting T-cell survival thereby enabling cytokines to initiate T-cell clonal expansion and differentiation. Thompson et al., *Proc. Natl. Acad. Sci. USA* 86: 1333-1337 (1989); Lucas et al., *J. Immunol.* 154: 5757-5768 (1995); Shahinian et al., *Science* 261: 609-612 (1993); Sperling et al., *J. Immunol.* 157: 3909-3917 (1996); Boise et al., *Immunity* 3: 87-98 (1995). CD28 also optimizes the responses of previously activated T-cells, promoting interleukin 2 (IL-2) production and T-cell survival. While some responses are CD28 independent, it is not yet clear whether this is co-stimulation independence resulting from strong antigenic simuli, or the result of dependence on other, unknown costimulatory pathways.

CTLA-4 activation causes a negative signal, which inhibits TCR- and CD-28 mediated signal transduction. CTLA-4 engagement results in the inhibition of IL-2 synthesis and progression through the cell cycle and termination of T-cell responses. Walunas et al., *Immunity* 1: 405-413 (1994); Walunas et al., *J. Exp. Med.* 183: 2541-2550 (1996); Krummel et al., *J. Exp. Med.* 182: 459-466 (1995); Brunner et al., *J. Immunol.* 162: 5813-5820 (1999); Greenwald et al., *Immunity* 14: 145-155 (2001). CTLA-4 plays an important role in regulating T-cell responses, including peripheral T-cell tolerance. While it is not clear how signaling is coordinated through CTLA-4 and CD28, some possibilities include outcompeting CD28 for binding to B7, by induction of immunosuppressive cytokines, direct antagonism of CD28 signaling and/or TCR-mediated signaling.

As a result, the antagonism of CTLA-4 (e.g., antagonist anti-CTLA antibodies) and or agonizing B7.1/B7.2/CD28 may be useful to enhance immune response in the treatment of infection (e.g., acute and chronic) and tumor immunity.

2. ICOS/ICOSL Signaling

Another pathway of interaction between APC's and T-cells occurs through ICOS (CD278) and ICOSL (B7-H2, CD275). ICOS/ICOSL signaling promotes T-helper cell differentiation and effector function, and is particularly important for interleukin-10 (IL-10) production, but plays a more modest role in regulating T cell expansion and IL-2 production, including regulatory T-cells, T cell tolerance and autoimmunity.

In contrast with CD28, ICOS is not expressed constitutively on naïve T-cells, but is induced rapidly on T-cells after TCR engagement. Hutloff et al., *Nature* 397: 263-266 (1999); Yoshinaga et al., *Nature* 402: 827-832 (1999); Beier et al., *Eur. J. Immunol.* 30: 3707-3717 (2000); Coyle et al., *Immunity* 13: 95-105 (2000); Mages et al., *Eur. J. Immunol.* 30: 1040-1047 (2000); McAdam et al., *J. Immunol.* 165: 5035-5040 (2000). This suggests that ICOS provides a co-stimulatory signal to activated T cells. While co-stimulation by CD28 enhances ICOS expression, and ICOS expression is reduced in the absence of B7.1 and B7.2, ICOS is not entirely dependent on CD28 signals. McAdam et al., *J. Immunol.* 165: 5035-5040 (2000); Aicher et al., *J. Immunol.* 164: 4689-4696 (2000); Kopf et al., *J. Exp. Med.* 192: 53-61 (2000). ICOS is upregulated on both T-helper type 1 and 2 $T_H1$ and $T_H2$) cells during the initial phase of differentiation, but levels remain high on $T_H2$ cells and decrease on $T_H1$ cells. The expression pattern of ICOS on T cells in germinal centers. Beier et al., *Eur. J. Immunol.* 30: 3707-3717 (2000); Mages et al., *Eur. J. Immunol.* 30: 1040-1047 (2000), indicates a role for ICOS in T-cell help for B cells. Functional studies have confirmed this, and even expression of ICOS has been confirmed on rat B cells, although not on other species. Tezuka et al., *Biochem. Biophys. Res. Commun.* 276: 335-345 (2000: McAdam et al., *Nature* 409: 102-105 (2001); Dong et al., *Nature* 409: 97-101 (2001); Dong et al., *J. Immunol.* 166: 3659-3662 (2001); Tafuri et al., *Nature* 409: 105-109 (2001).

One role for ICOS/ICOSL signaling seems to be for regulating cytokine production (e.g., IL-4, IL-13) by recently activated as well as effector T cells. Hutloff et al., *Nature* 397: 263-266 (1999); Coyle et al., *Immunity* 13: 95-105 (2000);

Dong et al., *Nature* 409: 97-101 (2001). In studies of allergic airway disease, $T_H2$ effector function, but not $T_H2$ differentiation, is provided by ICOS blockade. Tesciuba et al., *J. Immunol.* 167: 1996-2003 (2001). Indicating that ICOS can also regulate $T_H1$ effector function, production of both $T_H1$ and $T_H2$ cytokines can be suppressed by ICOS-Ig fusion protein upon reactivation in vitro. Kopf et al., *J. Exp. Med.* 192: 53-61 (2000).

Another potential role for ICOS relates to sustaining $T_H1$ responses. In an experimental model of autoimmune encephalomyelitis (EAE) for multiple sclerosis, a $T_H1$ disease mediated by myelin-specific CD4+ T cells, shows that the outcome of ICOS blockade might be distinct when costimulation is blocked during T-cell priming, then during the effector phase of EAE. Dong et al., *Nature* 409: 97-101 (2001); Rottman et al., *Nature Immunol.* 2: 605-611 (2001); Sporici et al., *Clin. Immunol.* 100: 277-288 (2001). EAE induced by myelin oligodendrocyte glycoprotein (MOG) is greatly exacerbated in ICOS$^{-/-}$ knock-out mice, with increased production of IFN-γ compared to wild type. Similarly, ICOS blockade during induction of EAE, exacerbated the disease also resulting in increased IFN-γ production. Therefore, ICOS blockade during priming leads to $T_H1$ polarization of the response. Interestingly, the priming of myelin-specific TCR transgenic T cells in vitro in the presence of ICOS-Ig inhibited their ability to induce EAE, in stark contrast to the results of ICOS-Ig blockade observed in vivo. Sporici et al., supra. The difference for the opposing outcomes in vitro and in vivo is not yet clear, but might reflect a role for ICOS on IL-10 producing regulatory T-cells, as well as effector T cells during ICOS blockade in vivo. Co-stimulation through IL-10 is very effective at enhancing IL-10 production and is more effective than co-stimulation through CD28. Hutloff et al., supra. The IL-10, IL-12 regulatory loop is critical in regulating EAE because IL-10−/−, but not IL4−/− mice develop exacerbated EAE. Segal et al., *J. Exp. Med.* 187: 537-546 (1998).

Yet another potential role for ICOS is in enhancing T-cell dependent B-cell humoral responses. ICOS$^{-/-}$ and ICOSL$^{-/-}$ mice have shown that ICOS is required for T-cell dependent B cell responses. Hutloff et al., *Nature* 397:263-66 (1999); Chapoval et al., *Nat. Immunol.* 2:269-74 (2001); Coyle et al., *Immunity* 13: 95-105 (2000); McAdam et al., *Nature* 409: 102-5 (2001); Tafuri et al., *Nature* 409: 105-9 (2001); Suh et al., *Nat. Immunol.* 4:899-906 (2003). ICOS$^{-/-}$ mice also show reduced germinal centers in response to primary immunization, profound defects in germinal center formation in response to secondary challenge, and defects in IgG class switching. The role of ICOS in T:B cell interaction was further validated by the identification of homozygous loss of ICOS in T cells in patients with adult onset common variable immunodeficiency disease. Grimbacher et al., *Nat. Immunol.* 4: 261-68 (2003).

As a result, agonism of ICOS/ICOSL (e.g., agonist anti-ICOS antibodies, soluble ICOS/ICOSL ligand) may be useful to enhance immune response in the treatment of infection (e.g., acute and chronic) and/or tumor immunity.

3. PD-1 Pathway

An important negative co-stimulatory signal regulating T cell activation is provided by programmed death-1 receptor (PD-1)(CD279), and its ligand binding partners PD-L1 (B7-H1, CD274) and PD-L2 (B7-DC, CD273). The negative regulatory role of PD-1 was revealed by PD-1 knock outs (Pdcd1$^{-/-}$), which are prone to autoimmunity. Nishimura et al., *Immunity* 11: 141-51 (1999); Nishimura et al., *Science* 291: 319-22 (2001). PD-1 is related to CD28 and CTLA-4, but lacks the membrane proximal cysteine that allows homodimerization. The cytoplasmic domain of PD-1 contains an immunoreceptor tyrosine-based inhibition motif (ITIM, V/IxYxxL/V). PD-1 only binds to PD-L1 and PD-L2. Freeman et al., *J. Exp. Med.* 192: 1-9 (2000); Dong et al., *Nature Med.* 5: 1365-1369 (1999); Latchman et al., *Nature Immunol.* 2: 261-268 (2001); Tseng et al., *J. Exp. Med.* 193: 839-846 (2001).

PD-1 can be expressed on T cells, B cells, natural killer T cells, activated monocytes and dendritic cells (DCs). PD-1 is expressed by activated, but not by unstimulated human CD4+ and CD8+ T cells, B cells and myeloid cells. This stands in contrast to the more restricted expression of CD28 and CTLA-4. Nishimura et al., *Int. Immunol.* 8: 773-80 (1996); Boettler et al., *J. Virol.* 80: 3532-40 (2006). There are at least 4 variants of PD-1 that have been cloned from activated human T cells, including transcripts lacking (i) exon 2, (ii) exon 3, (iii) exons 2 and 3 or (iv) exons 2 through 4. Nielsen et al., *Cell. Immunol.* 235: 109-16 (2005). With the exception of PD-1Δex3, all variants are expressed at similar levels as full length PD-1 in resting peripheral blood mononuclear cells (PBMCs). Expression of all variants is significantly induced upon activation of human T cells with anti-CD3 and anti-CD28. The PD-1Δex3 variants lacks a transmembrane domain, and resembles soluble CTLA-4, which plays an important role in autoimmunity. Ueda et al., *Nature* 423: 506-11 (2003). This variant is enriched in the synovial fluid and sera of patients with rheumatoid arthritis. Wan et al., *J. Immunol.* 177: 8844-50 (2006).

The two PD-1 ligands differ in their expression patterns. PD-L1 is constitutively expressed on mouse T and B cells, CDs, macrophages, mesenchymal stem cells and bone marrow-derived mast cells. Yamazaki et al., *J. Immunol.* 169: 5538-45 (2002). PD-L1 is expressed on a wide range of nonhematopoietic cells (e.g., cornea, lung, vascular epithelium, liver nonparenchymal cells, mesenchymal stem cells, pancreatic islets, placental synctiotrophoblasts, keratinocytes, etc.) [Keir et al., *Annu. Rev. Immunol.* 26: 677-704 (2008)], and is upregulated on a number of cell types after activation. Both type I and type II interferons IFN's) upregulate PD-L1. Eppihimer et al., *Microcirculation* 9: 133-45 (2002); Schreiner et al., *J. Neuroimmunol.* 155: 172-82 (2004). PD-L1 expression in cell lines is decreased when MyD88, TRAF6 and MEK are inhibited. Liu et al., *Blood* 110: 296-304 (2007). JAK2 has also been implicated in PD-L1 induction. Lee et al., *FEBS Lett.* 580: 755-62 (2006); Liu et al., *Blood* 110: 296-304 (2007). Loss or inhibition of phosphatase and tensin homolog (PTEN), a cellular phosphatase that modified phosphatidylinositol 3-kinase (PI3K) and Akt signaling, increased post-transcriptional PD-L1 expression in cancers. Parsa et al., *Nat. Med.* 13: 84-88 (2007).

PD-L2 expression is more restricted than PD-L1. PD-L2 is inducibly expressed on DCs, macrophages, and bone marrow-derived mast cells. PD-L2 is also expressed on about half to two-thirds of resting peritoneal B1 cells, but not on conventional B2 B cells. Zhong et al., *Eur. J. Immunol.* 37: 2405-10 (2007). PD-L2+B1 cells bind phosphatidylcholine and may be important for innate immune responses against bacterial antigens. Induction of PD-L2 by IFN-γ is partially dependent upon NF-κB. Liang et al., *Eur. J. Immunol.* 33: 2706-16 (2003). PD-L2 can also be induced on monocytes and macrophages by GM-CF, IL-4 and IFN-γ. Yamazaki et al., *J. Immunol.* 169: 5538-45 (2002); Loke et al., *PNAS* 100:5336-41 (2003).

PD-1 signaling typically has a greater effect on cytokine production than on cellular proliferation, with significant effects on IFN-γ, TNF-α and IL-2 production. PD-1 mediated inhibitory signaling also depends on the strength of the TCR signaling, with greater inhibition delivered at low levels of TCR stimulation. This reduction can be overcome by costimulation through CD28 [Freeman et al., *J. Exp. Med.* 192: 1027-34 (2000)] or the presence of IL-2 [Carter et al., *Eur. J. Immunol.* 32: 634-43 (2002)].

Evidence is mounting that signaling through PD-L1 and PD-L2 may be bidirectional. That is, in addition to modifying TCR or BCR signaling, signaling may also be delivered back to the cells expressing PD-L1 and PD-L2. While treatment of dendritric cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-α and IL-6, and stimulated T cell proliferation. Nguyen et al., *J. Exp. Med.* 196: 1393-98 (2002). Treatment of mice with this antibody also (1) enhanced resistance to transplanted b16 melanoma and rapidly induced tumor-specific CTL. Radhakrishnan et al., *J. Immunol.* 170: 1830-38 (2003); Radhakrishnan et al., *Cancer Res.* 64: 4965-72 (2004); Heckman et al., *Eur. J. Immunol.* 37: 1827-35 (2007); (2) blocked development of airway inflammatory disease in a mouse model of allergic asthma. Radhakrishnan et al., *J. Immunol.* 173: 1360-65 (2004); Radhakrishnan et al., *J. Allergy Clin. Immunol.* 116: 668-74 (2005).

Further evidence of reverse signaling into dendritic cells ("DC's") results from studies of bone marrow derived DC's cultured with soluble PD-1 (PD-1 EC domain fused to Ig constant region—"s-PD-1"). Kuipers et al., *Eur. J. Immunol.* 36: 2472-82 (2006). This sPD-1 inhibited DC activation and increased IL-10 production, in a manner reversible through administration of anti-PD-1.

Additionally, several studies show a receptor for PD-L1 or PD-L2 that is independent of PD-1. B7.1 has already been identified as a binding partner for PD-L1. Butte et al., *Immunity* 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L1 delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L1), T cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L1 (i.e., no PD-1 and B7.1), T cell proliferation was no longer impaired by anti-CD3 plus PD-L1 coated beads. Thus, PD-L1 can exert an inhibitory effect on T cells either through B7.1 or PD-1.

The direct interaction between B7.1 and PD-L1 suggests that the current understanding of costimulation is incomplete, and underscores the significance to the expression of these molecules on T cells. Studies of PD-L1$^{-/-}$ T cells indicate that PD-L1 on T cells can down-regulate T cell cytokine production. Latchman et al., *Proc. Natl. Acad. Sci. USA* 101: 10691-96 (2004). Because both PD-L1 and B7.1 are expressed on T cells, B cells, DCs and macrophages, there is the potential for directional interactions between B7.1 and PD-L1 on these cells types. Additionally, PD-L1 on non-hematopoietic cells may interact with B7.1 as well as PD-1 on T cells, raising the question of whether PD-L1 is involved in their regulation. One possible explanation for the inhibitory effect of B7.1: PD-L1 interaction is that T cell PD-L1 may trap or segregate away APC B7.1 from interaction with CD28.

As a result, the antagonism of signaling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present invention, may be combined with antagonists of other components of PD-1:PD-L1 signaling, for example, antagonist anti-PD-1 and anti-PD-L2 antibodies.

4. B7-H3

Co-stimulatory signals are also provided through B7-H3 (B7RP-2, CD276, PRO352), which is broadly expressed in lymphoid and non-lymphoid tissues. Chapoval et al., *Nat. Immunol.* 2: 269-74 (2001). In humans, B7-H3 has both a 4Ig and a 2Ig variant, with the 4Ig form predominating, while the 2Ig variant predominates in the mouse. Sun et al., *J. Immunol.* 168: 6294-97 (2002); Steinberger et al., *J. Immunol.* 172: 2352-59 (2004); Ling et al., *Genomics* 82: 365-77 (2003).

Recent studies have shown that B7-H3 is both a stimulator and an inhibitor of T cell responses. Evidence of stimulatory activation is provided by the following: (1) In combination with anti-CD3, B7-H3/Ig fusions costimulated CD4+ and CD8+ T cell proliferation, and stimulated IFN-γ and CD8 lytic activity, Chapoval et al., *Nat. Immunol.* 2: 269-74 (2001); and (2) Injection of B7-H3 expression plasmid into tumors of an EL-4 lymphoma model resulted in complete regression of 50% of tumors, which was dependent upon CD8+ T cells and NK cells. However, several recent studies have shown an inhibitory role for this molecule. B7-H3$^{-/-}$ APC knockouts show a two-fold increase in alloreactive T cell proliferation in an MLR response. Activation of CD4 T cells by anti-CD3 and anti-CD28 was inhibited in HLA-DR2 transfected with either form of B7-H3. Ling et al., *Genomics* 82: 365-77 (2003). The result was reduced proliferation and production of IFN-γ, TNF-α, IL-10 and GM-CSF. The reconciliation of these studies could lie in the existence of two receptors for B7-H3 with opposing functions, similar to how CD28 and CTLA-4 regulate signaling via B7.1 and B7.2.

As a result, the blockade of B7-H3 signaling may contribute to enhancing immune response to infection and tumor immunity when combined with the anti-PD-L1 antibodies of the invention.

5. B7-H4

The most recent addition to the B7 family is B7-H4 (B7x, B7-S1, B7-H.5, VTCN1, PRO1291), which is a negative regulator of T cell responses. Zang et al., *Proc. Natl. Acad. Sci. U.S.A.* 100 (18), 10388-10392 (2003); Watanabe et al., *Nat. Immunol.* 4 (7), 670-679 (2003); Prasad, et al., *Immunity* 18(6), 863-873 (2003); Sica et al., *Immunity* 18 (6), 849-861 (2003). Both human and mouse B7-H4 are expressed broadly in both lymphoid (spleen and thymus) and nonlymphoid organs (including lung, liver, testis, ovary, placenta, skeletal muscle, pancreas and small intestine). B7-H4 is not detected in normal human tissues by IHC or regulation of B7-H4 at the translational level. IHC shows B7-H4 is highly expressed in lung and ovarian tumors, and real-time polymerase chain reaction (PCR) analysis indicate that mouse B7-H4 also is highly expressed in prostate, lung and colon carcinoma cell lines. B7-H4 binds a yet unknown receptor on activated, but not naïve T cells that is distinct from CTLA-4, ICOS, PD-1 and the receptor for B7-H3. Although BTLA was initially reported to be the ligand for B7-H4, the reported binding of B7-H4/Ig fusions to wild-type, but not BTLA$^{-/-}$ cells compels the conclusion that HVEM, and not BTLA is the unique ligand for B7-H4. Sedy et al., *Nat. Immunol.* 6: 90-98 (2004).

Studies with B7-H4 transfectants and immobilized B7-H4/Ig fusions demonstrate that B7-H4 delivers a signal that inhibits TCR-mediated CD4$^+$ and CD8$^+$ T cell proliferation, cell-cycle progression in the G0/G1 phase, and IL-2 production. Sica et al., *Immunity* 18: 849-61 (2003); Zang et al., *PNAS* 100: 10388-92 (2003); Prasad et al., *Immunity* 18: 863-73 (2003). B7.1 costimulation cannot overcome B7-H4/Ig induced inhibition. Blocking anti-B7-H4 antibody increased T cell proliferation and IL-2 production in vitro. In vivo administration of anti-B7-H4 antibody commensurate with administration of kehole limpet hemacyanin (KLH) in complete Freund's adjuvant (CFA) led to a modest increase in anti-KLH antibody IgM production and a two- to three-fold increase in T cell proliferation and IL-2 production upon in vitro restimulation with KLH, suggesting greater T cell priming in vivo in the presence of anti-B7-H4. Anti-B7-H4 blocking antibody markedly accelerated the onset and severity of EAE in increased CD4$^+$ and CD8$^+$ T cells and CD11b$^+$ macrophages in the brain of anti-B7-H4 treated an autoimmune mouse model. The combined experimental data available on B7-H4 suggest that it may downegulate immune responses in peripheral tissues and play a role in regulating T cell tolerance. The expression of B7-H4 may also play a role in evasion of host immune responses in tumor immunity. Choi et al., *J. Immunol.* 171: 4650-54 (2003). As a result, the antagonism of B7-H4 may be useful to enhance immune response to infection and tumor immunity when combined with the anti-PD-L1 antibodies of the invention.

6. BTLA

The B7 family member BTLA (CD272, BTLA-1) is functionally similar to PD-1 and CTLA. Initially identified as a selective marker for Th1 cells, BTLA is only expressed on lymphocytes. Similar to CTLA-4, ICOS and PD-1, BTLA is induced on T cells during activation. However, in contrast with ICOS, which remains elevated on Th2-cells, but is downregulated in Th1 cells, BTLA remains expressed on Th1-cells, but not Th2-cells. Similar to PD-1, BTLA is also expressed on B-cells. Gavrieli et al., *Biochem. Biophys. Res. Commun.* 312: 1236-43 (2003). However, BTLA is expressed on both resting and activated B cells, whereas PD-1 is upregulated on activated B cells. BTLA has two ITIM motifs.

BTLA exerts inhibitory effects on both B and T lymphocytes. Watanabe et al., *Nat. Immunol.* 4: 670-79 (2003). BLTA$^{-/-}$ B cells show modest response to anti-IgM, but an increased response to anti-CD3 in vitro. Polarized BTLA$^{-/-}$ Th1 cells show about a two-fold increase in proliferation in response to antigen exposure, in vitro. In vivo, BTLA$^{-/-}$ mice show a three-fold increase in hapten-specific antibody responses and enhanced susceptibility to EAE. The phenotype of BTLA$^{-/-}$ mice resembles the phenotype of PD-1$^{-/-}$ mice, exhibiting increased susceptibility to autoimmunity, but more subtle phenotypes than CTLA-4$^{-/-}$ mice. However, given its role as a negative regulator, blockade of BTLA may prove useful for enhancing immune response in infection and antitumor immunity when combined with the anti-PD-L1 antibodies of the invention.

Interestingly, it has recently been shown that the Ig superfamily member BTLA also interacts with the TNFR family member HVEM. Sedy et al., *Nat. Immunol.* 6: 90-98 (2005); Gonzalez et al., *Proc. Natl. Acad. Sci. USA* 102: 1116-1121 (2005). HVEM is reviewed below under TNFR Family Costimulators.

E. TNFR Family Costimulators

1. OX40/OX40L (CD134)

OX40 (CD134, TXPG1L, TNFRSF4) and OX40L (CD134L, CD252, GP34, TNFSF4, TXGP1) deficient mice have reduced primary CD4+ T-cell responses both to viral and common protein antigens and in contact-sensitivity reactions. Chen et al., *Immunity* 11: 689-698 (1999); Kopf et al., *Immunity* 11: 699-708 (1999); Murata et al., *J. Exp. Med.* 191: 365-374 (2000); Gramaglia et al., *J. Immunol.* 165: 3043-3050 (2000). Lower frequencies of antigen-specific effector T cells are generated late in the primary response and fewer memory T cells develop. Gramaglia et al., supra. In contrast to T cells deficient in CD27, early proliferation is unimpaired in naïve CD4+ T cell populations that are deficient in OX40. However, reduced proliferation and marked apoptotic cell death occur 4-5 days after activation, with the result that few T cells survive long term. Rogers et al., *Immunity* 15: 445-455 (2001). With OX40-deficient CD8+ T cells, initial cell division is unaffected, but the accumulation of primary effector cells is markedly reduced 3-6 days after encounter with antigen. Croft et al., *Nat. Immunol.* 3: 609-620 (2003).

Transgenic expression of OX40L by dendritic cells or T cells increased the number of antigen-responding CD4+ T cells and produces autoimmune-like symptoms that are associated with aberrant T-cell activation. Brocker et al., *Eur. J. Immunol.* 29:1610-1616 (1999); Murata et al., *J. Immunol.* 169: 4628-4636 (2002). After immunization, injection of agonist anti-OX40 antibodies results in the accumulation of a greater number of antigen-reactive CD4+ T cells at the peak of the primary response, and a concomitant enhancement in the number of memory T cells that are generated. Gramaglia et al., supra., Bansai-Pakala et al., *Nature Med.* 7: 907-912 (2001), Maxwell et al., *J. Immunol.* 164: 107-112 (2000); Weatherill et al., *Cell. Immunol.* 209: 63-75 (2001). Enhanced accumulation of primary effector CTLs occurs when antigen-primed mice are treated with agonist antibody specific for OX40. De Smedt et al., *J. Immunol.* 168: 661-670 (2002).

OX40 is believed to provide a late-acting signal that allow for the survival of newly generated effector cells at the peak of the primary immune response. There is also good evidence that OX40 functions downstream from CD28—in addition to increased expression of OX40 mediated by CD28 signals, functional analysis of CD28 deficiency versus OX40 deficiency have shown that early primary T-cell responses are markedly impaired in the absence of CD28 signals, but only late responses are impaired in the absence of OX40 signals. Rogers et al., *Immunity* 15: 445-455 (2001); Bertram et al., *J. Immunol.* 168: 3777-3785 (2002).

As a result, it is likely that activation of OX40/OX40L, such as through the application of agonist antibodies may be useful when combined with the anti-PD-L1 antibodies of the invention to treat T-cell dysfunctional disorders.

2. 4-1BB (CD137)/4-1BBL

Similar to OX40/OX40L, T-cells that are deficient in 4-1BB (CD137, TNFRSF9) and 4-1BBL (TNFSF9), show fewer antigen-reactive CD8+ T cells accumulate in primary responses when 4-1BBL is absent and fewer memory T cells develop. DeBenedette et al., *J. Immunol.* 163: 4833-4841 (1999); Tan et al., *J. Immunol.* 163: 4859-4868 (1999); Tan et al., *J. Immunol.* 164: 2320-2325 (2000). Also, blocking 4-1BBL does not alter the initial proliferative response of CD8+ T cells, but suppresses the accumulation of effector CTLs at the peak of the primary response after 3-6 days, owing to apoptosis of cells that have divided several times. Cooper et al., *Eur. J. Immunol.* 32: 521-529 (2002). Agonist anti-4-1BB antibodies and anti-4-1BBL-transfected APCs have also produced similar results: CTL and CD4+ T-cell responses are markedly increased in vivo. Melero et al., *Nature Med.* 3: 682-685 (1997); Melero et al., *Eur. J. Immunol.* 28: 1116-1121 (1998); Takahashi et al., *J. Immunol.* 162: 5037-5040 (1999); Guinn et al., *J. Immunol.* 162: 5003-5010 (1999); Halstead et al., *Nature Immunol.* 3: 536-541 (2002); Takahashi et al., *Immunol. Lett.* 76: 183-191 (2001); Bansal-Pakala et al., *J. Immunol.* 169: 5005-5009 (2002). 4-1BB-specific antibody does not alter the initial proliferative response, supporting the conclusions from the 4-1BBL blocking experiments and pointing to the late activity of 4-1BB in supplying cell-survival signals.

Like OX40, 4-1BB is believed to provide a late-acting signal that allow for the survival of newly generated effector cells at the peak of the primary immune response. There is also good evidence that 4-1BB functions later than CD28—in addition to increased expression of OX40 and 4-1 BB mediated by CD28 signals, functional analysis of CD28 deficiency versus 4-1BB deficiency have shown that early primary T-cell responses are markedly impaired in the absence of CD28 signals, but only late responses are impaired in the absence of OX40 signals. Rogers et al., *Immunity* 15: 445-455 (2001); Bertram et al., *J. Immunol.* 168: 3777-3785 (2002).

Agonist anti-CD137 antibody can induce tumor regression in cancer wherein CD8+ CTLs play a central role. Melero et al., *Nat. Med.* 3: 682-5 (1997); Hirano et al., *Cancer Res.* 65(3): 1089-96 (2005). Constitutive and inducible expression of PD-L1 confers resistance is such tumors, which is reversible upon blockade of PD-L1. Hirano et al.

As a result, it is likely that activation of 4-1BB/4-BBL, such as through the application of agonist antibodies, particularly in combination with PD-L1 antagonists (e.g., anti-PD-L1 antibody) may be useful to treat T-cell dysfunctional disorders.

3. CD27/CD27L (CD70)

The importance of CD27 (TNFRSF7, S152) and CD27L (CD70, TNFSF7) signaling in the initial stages of a T-cell response has been demonstrated in in vitro blocking studies, wherein CD27/CD70 interactions were disrupted. Oshima et al., *Int. Immunol.* 10: 517-526 (1998); Agematsu et al., *J. Immunol.* 153: 1421-1429 (1994); Hintzen et al., *J. Immunol.* 154: 2612-2623 (1995). T cells that lack CD27 initially divide normally, but then proliferate poorly 3 or more days after activation. Hendriks et al., *Nature Immunol.* 1: 433-440 (2000). This indicates that CD27 participates in promoting the initial expansion of the naïve T-cell population, by either early suppression of T-cell death or by acting on the cell cycle to allow sustained division 2-3 days after activation. This is reinforced by in vivo studies of CD27-deficient mice, in which lower numbers of antigen-specific responses (days 4-8) and fewer memory T cells develop over 3 or more weeks. Hendriks et al., supra. The expression of CD27 is upregulated early after T-cell activation, suggesting that it mainly delivers signals that maintain early proliferation, before the peak of the effector response.

As a result, it is likely that activation of CD27/CD27L, including through the application of agonist antibodies, particularly in combination with the anti-PD-L1 antibodies described herein, may be useful to treat T-cell dysfunctional disorders.

4. CD30/CD30L (CD153)

CD30 (TNFRSF8, Ki-1) and CD30L (CD153, TNFSF8) signaling is co-stimulatory for several T-cell functions in vitro. Del Prete et al., *J. Exp. Med.* 182: 1655-1661 (1995), Bowen et al., *J. Immunol.* 156: 442-449 (1995). Blocking reagents to CD30L suppressed the development of Th2 cells and enhanced the development of Th1 cells in vitro. This activity is in agreement with data showing that CD30 is preferentially expressed by Th2 cells and type 2 cytotoxic Tc2 cells. Del Prete et al., supra, Nakamura et al., *J. Immunol.* 158: 2090-2098 (1996). CD30 is expressed 3-4 days after the activation of naïve T cells in unpolarized primary responses. Nakamura et al., supra, indicating that its role is not restricted to type 2 cytokine-dominated responses.

While the exact mechanisms of CD30/CD30L signaling is unclear, it has been suggested that it might be similar to OX40 and 4-1BB. When adoptively transferred antigen-specific CD8+ T cells are transferred into CD30L-deficient mice, they do not accumulate in high numbers at the peak of a primary response, and fewer memory T cells develop. As a result, CD30 might also provide proliferation and/or survival signals to allow the generation of high numbers of antigen-specific T cells at the peak of primary responses.

As a result, it is likely that activation of CD27/CD27L, including through the application of agonist antibodies, particularly in combination with the anti-PD-L1 antibodies described herein, may be useful to treat T-cell dysfunctional disorders.

5. HVEM/LIGHT

The effect of HVEM (HVEA, ATAR, LIGHTR, TNFRSF14, PRO509) and LIGHT (CD258, HVEML, TR2, TNFSF14, PRO726) on T-cell costimulation is complicated by 1) the ability of LIGHT to also bind lympotoxin-β receptor (LTβR) and 2) HVEM to bind soluble LTα3. Thus, any study of the effect of HVEM/LIGHT should also take into account the effect of other binding partners for this signaling system. Blocking LIGHT can inhibit early T-cell proliferation and cytokine secretion in allogeneic mixed-lymphocyte reactions (MLRs). Tamada et al., *J. Immunol.* 164: 4105-4110 (2000), Kwon et al., *J. Biol. Chem.* 272: 14272-14276 (1997); Harrop et al., *J. Immunol.* 161: 1786-1794 (1998); Tamada et al., *Nature Med.* 6: 283-289 (2000). The production of pro-inflammatory cytokines is suppressed when LIGHT is blocked in MHC-mismatched heart allografts. Ye et al., *J. Exp. Med.* 195: 795-800 (2002). Moreover, allogeneic skin grafts are rejected with delayed kinetics in recipients that are deficient for both LIGHT and CD28. Scheu et al., *J. Exp. Med.* 195: 1613-1624 (2002). The suggestion that delayed graft rejection might indicate an early suppression of T-cell clonal expansion or cytokine production. This conclusion is bolstered by (i) in vitro studies showing that LIGHT-deficient splenocytes responding to alloantigen have reduced production of both TH1 and TH2 cytokines and weak generation of cytotoxic T lymphocyte activity (CTL) activity [Sheu et al., supra.], and (ii) in vivo studies showing that blocking LIGHT reduces the generation of alloreactive CTLs. Tamada et al., *Nature Med.* 6: 283-289 (2000).

As a result, the HVEM/LIGHT, such as through the application of agonist antibodies, particularly in combination with the anti-PD-L1 antibodies described herein, may be useful to treat T-cell dysfunctional disorders.

II. Definitions

An "allergen" or "immunogen" is any molecule that can trigger an immune response. As used herein, the term covers either the antigenic molecule itself, or its source, such as pollen grain, animal dander, insect venom or food product. This is contrasted with the term antigen, which refers to a molecule that can be specifically recognized by an immunoglobulin or T-cell receptor. Any foreign substance capable of inducing an immune response is a potential allergen. Many different chemicals of both natural and synthetic origin are known to be allergenic. Complex natural organic chemicals, especially proteins, are likely to cause antibody-mediated allergy, whereas simple organic compounds, inorganic chemicals, and metals more preferentially cause T-cell mediated allergy. In some cases, the same allergen may be responsible for more than one type of allergy. Exposure to the allergen may be through inhalation, injection, injection, or skin contact.

"Dysfunction" in the context of immune dysfunction, refers to a state of immune reduced responsiveness to antigenic stimulation. The term includes the common elements of both exhaustion and/or anergy in which antigen recognition may occur, but the ensuing immune response is ineffective to control infection or tumor growth.

"Tolerance" or "immunological tolerance" is the failure of the immune system to mount a defensive immune response to a particular antigen. Tolerance can be natural or self, wherein the body does not attack its own proteins and antigens, or it can be induced, resulting from the manipulation of the immune system. Central tolerance occurs during lymphocyte development and operates in the thymus and bone marrow. During this process, T and B lymphocytes that recognize self antigens are deleted before they develop into fully immunocompetent cells. This process is most active during fetal development, but continues throughout life as immature lymphocytes are generated. Peripheral T-cell tolerance refers to a functional unresponsiveness to self-antigens that are present in peripheral tissues, and occurs after T and B cells mature and enter the periphery. These processes include the suppression of autoreactive cells by "regulatory" T cells and the generation of hyporesponsiveness (anergy) in lymphocytes which encounter antigen in the absence of the co-stimulatory signals that accompany inflammation. "Acquired" or "induced tolerance" refers to the immune system's adaptation to external antigens characterized by a specific non-reactivity of the lymphoid tissues to a given antigen that in other circumstances would likely induce cell-mediated or humoral immunity. In adults, tolerance may be clinically induced by repeated administration of very large doses of antigen, or of small doses that are below the threshold required for stimulation of an immune response, such as via intravenous or sublingual administration of soluble antigens. Immunosuppression also facilitates the induction of tolerance. The breakdown of self tolerance can lead to autoimmunity.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral or pathogen clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Chronic infection" refers to an infection in which an infectious agent (e.g., pathogens such as viruses, bacteria, protozoan parasites, fungi, or the like) has induced an immune response in the infected host, but has not been cleared or eliminated from that host as during an acute infection. Chronic infections may be persistent, latent, or slow. While acute infections are typically resolved by the immune system within a few days or weeks (e.g., influenza), persistent infections can persist at a relatively low level for months, years, decades, or a lifetime (e.g., Hepatitis B). In contrast, a latent infection is characterized by a long period of asymptomatic activity punctuated by a period of rapidly increasing high grade infection and elevated pathogen levels (e.g., herpes simplex). Finally, a slow infection is one characterized by a gradual and continuous increase in disease symptoms, such as a long period of incubation followed by a protracted and progressive clinical course beginning after the onset of clinical symptoms. Unlike latent and persistent infections, slow infection may not begin with an acute period of viral multiplication (e.g., picornaviruses infection, visnavirus, scrapie, Creutzfeldt-Jakob disease). Exemplary infectious agents capable of inducing a chronic infection include viruses (e.g., cytomegalovirus, Epstein Barr virus, hepatitis B virus, hepatitis C virus, herpes simplex virus, types I and II, human immunodeficiency virus, types 1 and 2, human papillomavirus, human T lymphotrophic viruses, types 1 and 2, varicella zoster virus and the like), bacteria (e.g., *Mycobacterium tuberculosis, Listeria* spp., *Klebsiella pneumoniae, Streptococcus pneumoniae, Staphylococcus aureus, Borrelia* spp., *Helicobacter pylori*, and the like), protozoan parasites (e.g., *Leishmania* spp., *Plasmodium falciparum, Schistosoma* spp., *Toxoplasma* spp., *Trypanosoma* spp., *Taenia carssiceps* and the like), and fungi (e.g., *Aspergillus* spp., *Candida albicans, Coccidioides immitis, Histoplasma capsulatum, Pneumocystis carinii* and the like). Additional infectious agents include prions or misfolded proteins that affect the brain or of neuron structure by further propagating protein misfolding in these tissues, resulting in the formation of amyloid plaques which cause cell death, tissue damage and eventual death. Example of disease resulting from prion infection include: Creutzfeldt-Jakob disease and its varieties, Gerstmann-Straussler-Scheinker syndrome (GSS), fatal familial insomnia (sFI), kuru, scrapie, Bovine spongiform encephalopathy (BSE) in cattle (aka "mad cow" disease), and various other animal forms of encephalopathy [e.g., transmissible mink encephalopathy (TME), chronic wasting disease (CWD) in white-tailed deer, elk and mule deer, feline spongiform encephalopathy, exotic ungulate encephalopathy (EUE) in nyala, oryx and greater kudu, spongiform encephalopathy of the ostrich].

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

A "B7-negative costimulatory antagonist" ("BNCA") is an agent that decreases, blocks, inhibits, abrogates or interferes with the negative co-stimulatory signal mediated by or through cell surface proteins expressed on T lymphocytes mediated by a member of the B7 family. In one aspect, a BNCA may either alone, or in combination with the anti-PD-1 antibodies of the invention render a dysfunctional T-cell non-dysfunctional. In another aspect, a BNCA may be an agent that inhibits nucleic acid or protein synthesis, expression, signaling, and/or post-expression processing of a B7-negative costimulatory molecule. In yet another aspect, a BNCA is an antibody, antigen binding antibody fragment, BNCA oligopeptide, BNCA RNAi or BNCA small molecule that decreases, blocks, inhibits, abrogates or interferes with signal transduction by a B7-negative costimulatory molecule. Example B7 negative costimulatory molecules includes: CTLA-4, PD-L1, PD-1, B7.1 (expressed on T-cells), PD-L2, B7-H3 and B7-H4.

A positive costimulatory agonist is a molecule that increases, enhances, augments or facilitates a co-stimulatory signal mediated by or through cell surface proteins expressed on T lymphocytes. In one aspect, a positive costimulatory molecule can be an extracellular domain, soluble construct or agonist antibody which activates a positive costimulatory pathway. Example positive costimulatory molecules include the B7 superfamily molecules, e.g., B7.1, B7.2, CD28 and ICOS/ICOSL. Additional examples include the TNFR family costimulatory molecules, e.g., OX40/OX40L, 41-BB/41-BBL, CD27/CD27L, CD30/CD30L and HVEM/LIGHT.

A "small molecule" or "small organic molecule" is one that has a molecular weight below about 500 Daltons.

An "interfering RNA" "RNAi" is RNA of 10 to 50 nucleotides in length which reduces expression of a target gene, wherein portions of the strand are sufficiently complementary (e.g., having at least 80% identity to the target gene). The method of RNA interference refers to the target-specific suppression of gene expression (i.e., "gene silencing"), occurring at a post-transcriptional level (e.g., translation), and includes all posttranscriptional and transcriptional mechanisms of RNA mediated inhibition of gene expression, such as those described in P. D. Zamore, *Science* 296: 1265 (2002) and Hannan and Rossi, *Nature* 431: 371-378 (2004). As used herein, RNAi can be in the form of small interfering RNA (siRNA), short hairpin RNA (shRNA), and/or micro RNA (miRNA). Such RNAi molecules are often a double stranded RNA complexes that may be expressed in the form of separate complementary or partially complementary RNA strands. Methods are well known in the art for designing double-stranded RNA complexes. For example, the design and synthesis of suitable shRNA and siRNA may be found in Sandy et al., *BioTechniques* 39: 215-224 (2005).

A "small interfering RNA" or siRNA is a double stranded RNA (dsRNA) duplex of 10 to 50 nucleotides in length which reduces expression of a target gene, wherein portions of the first strand is sufficiently complementary (e.g., having at least 80% identity to the target gene). siRNAs are designed specifically to avoid the anti-viral response characterized by elevated interferon synthesis, nonspecific protein synthesis inhibition and RNA degradation that often results in suicide or death of the cell associated with the use of RNAi in mammalian cells. Paddison et al., *Proc Natl Aced Sci USA* 99(3): 1443-8. (2002).

The term "hairpin" refers to a looping RNA structure of 7-20 nucleotides. A "short hairpin RNA" or shRNA is a single stranded RNA 10 to 50 nucleotides in length characterized by a hairpin turn which reduces expression of a target gene, wherein portions of the RNA strand are sufficiently complementary (e.g., having at least 80% identity to the target gene). The term "stem-loop" refers to a pairing between two regions of the same molecule base-pair to form a double helix that ends in a short unpaired loop, giving a lollipop-shaped structure.

A "micro RNA" or "miRNA" (previously known as stRNA) is a single stranded RNA of about 10 to 70 nucleotides in length that are initially transcribed as pre-miRNA characterized by a "stem-loop" structure, which are subsequently processed into mature miRNA after further processing through the RNA-induced silencing complex (RISC).

A "BNCA interfering RNA" or "BNCA RNAi" binds, preferably specifically, to a BNCA nucleic acid and reduces its expression. This means the expression of the B7 negative costimulatory molecule is lower with the BNCA RNAi present as compared to expression of the B7 negative costimulatory molecule in a control where the BNCA RNAi is not present. BNCA RNAi may be identified and synthesized using known methods (Shi Y., *Trends in Genetics* 19(1): 9-12 (2003), WO2003056012, WO2003064621, WO2001/075164, WO2002/044321.

A "BNCA oligopeptide" is an oligopeptide that binds, preferably specifically, to a B7 negative costimulatory polypeptide, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. *Proc. Natl. Acad. Sci. USA*, 87:6378 (1990); Lowman, H. B. et al. *Biochemistry*, 30:10832 (1991); Clackson, T. et al. *Nature*, 352: 624 (1991); Marks, J. D. et al., *J. Mol. Biol.*, 222:581 (1991); Kang, A. S. et al. *Proc. Natl. Acad. Sci. USA*, 88:8363 (1991), and Smith, G. P., *Current Opin. Biotechnol.*, 2:668 (1991).

A "BNCA small molecule antagonist" or "BNCA small molecule" is an organic molecule other than an oligopeptide or antibody as defined herein that inhibits, preferably specifically, a B7 negative costimulatory polypeptide. Such B7 negative co-stimulatory signaling inhibition preferably renders a dysfunctional T-cell responsive to antigen stimulation. Example BNCA small molecules may be identified and chemically synthesized using known methodology (see, e.g., PCT Publication Nos. WO2000/00823 and WO2000/39585). Such BNCA small molecules are usually less than about 2000 daltons in size, alternatively less than about 1500, 750, 500, 250 or 200 daltons in size, are capable of binding, preferably specifically, to a B7 negative stimulatory polypeptide as described herein, and may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

The term "antibiotic" includes any molecule that specifically inhibits or abolishes the growth of micro-organisms, such as virus, bacteria, fungi or protozoa, but is non-lethal to the host at the concentration and dosing interval administered. As used herein, the term antibiotic includes anti-bacterial agent, anti-viral, agent, anti-fungal agent and anti-protozoan agent. In a specific aspect, an antibiotic is non-toxic to the host at the administered concentration and dosing intervals. Anti-bacterial antibiotics or anti-bacterials can be broadly classified as either bactericidal (i.e., directly kills) or bacteriostatic (i.e., prevents division). Anti-bacterial antibiotics can be further subclassified as narrow-spectrum (i.e., only affects a small class of subset of bacteria, e.g., gram-negative, etc.) or broad-spectrum (i.e., affects a broad class). Examples of antibiotics include: (i) aminoglycosides, e.g., amikacin, gentamicin, kanamycin, neomycin, netilmicin, streptomycin, tobramycin, paromycin, (ii) ansamycins, e.g., geldanamycin, herbimycin, (iii) carbacephems, e.g., loracarbef, (iv), carbapenems, e.g., ertapenum, doripenem, imipenem/cilastatin, meropenem, (v) cephalosporins (first generation), e.g., cefadroxil, cefazolin, cefalotin, cefalexin, (vi) cephalosporins (second generation), e.g., ceflaclor, cefamandole, cefoxitin, cefprozil, cefuroxime, (vi) cephalosporins (third generation), e.g., cefixime, cefdinir, cefditoren, cefoperazone, cefotaxime, cefpodoxime, ceftazidime, ceftibuten, ceftizoxime, ceftriaxone, (vii) cephalosporins (fourth generation), e.g., cefepime, (viii), cephalosporins (fifth generation), e.g., ceftobiprole, (ix) glycopeptides, e.g., teicoplanin, vancomycin, (x) macrolides, e.g., axithromycin, clarithromycin, dirithromycine, erythromycin, roxithromycin, troleandomycin, telithromycin, spectinomycin, (xi) monobactams, e.g., axtreonam, (xii) penicilins, e.g., amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin, (xiii) antibiotic polypeptides, e.g., bacitracin, colistin, polymyxin B, (xiv) quinolones, e.g., ciprofloxacin, enoxacin, gatifloxacin, levofloxacin, lemefloxacin, moxifloxacin, norfloxacin, orfloxacin, trovafloxacin, (xv) sulfonamides, e.g., mafenide, prontosil, sulfacetamide, sulfamethizole, sulfanilamide, sulfasalazine, sulfisoxazole, trimethoprim, trimethoprim-sulfamethoxazole (TMP-SMX), (xvi) tetracyclines, e.g., demeclocycline, doxycycline, minocycline, oxytetracycline, tetracycline and (xvii) others such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or tinidazole.

The term "antiviral agent" includes any molecule that inhibits or abolishes the growth, morbidity and/or survival of viruses. This includes anti-retroviral drugs such as (1) reverse transcriptase inhibitors including for example: (a) nucleoside analog reverse transcriptase inhibitors (NRTIs) (E.g., aciclovir/acyclovir (ZOVIRAX®, ZOVIR®), cidofovir, azidothymidine/zidovudine (AZT, RETROVIR®), didanosine (ddI, VIDEX®; zalcitabine (ddC, HIVID®); stavudine (d4T, ZERIT®; lamivudine (3TC, EPIVIR®); abacavir (ZIAGEN®); emtricitabine (EMTRIVA®); brivudine (HELPIN®); entecavir (BARACLUDE®); idoxuridine; viramidine (taribavirin by Valeant Pharmaceuticals), cytidine nucleoside analog polymerase inhibitor PCI-6130, and prodrug variants (e.g., R7128) by Pharmasset/Roche; nucleoside analog inhibitor by Merck/Isis Pharmaceuticals—MK-0608, (b) nucleotide analog reverse transcriptase inhibitors (NtRTIs) (E.g., tenofovir (VIREAD®); adefovir (PREVEON®, HEPSERA®); fomivirsen (VITRAVENE®); (c) non-nucleoside reverse transcriptase inhibitors, (NNRTIs), efavirenz (SUSTIVA®, STOCRIN®); nevirapine (VIRAMUNE®), delavirdine (RESCREPTOR®), etravirine (INTELENCE®), loviride; non-nucleoside inhibitor of HCV RNA-dependent RNA polymerase by ViroChem Pharma—VCH-759, non-nucleoside inhibitor of HCV polymerase inhibitor by Pfizer—PF-868554; and (d) polymerase inhibitors, including: RNA-dependent RNA polymerase of the hepatitis C virus by Boehringer Ingelheim—BILB-1941, RNA polymerase inhibitor by Roche—R1626; ACH-0137171 a replicase inhibitor by Achillion Pharmaceuticals, R7128—polymerase inhibitor by Roche/Pharmasset, ABT-333, and ABT-072—polymerase inhibitors by Abbott, BI 207127 polymerase inhibitor by Boehringer Ingelheim, PSI-7851—polymerase inhibitor by Pharmasset, ANA598—polymerase inhibitor by Anadys Pharmaceuticals, MK-3281—polymerase inhibitor by Merck, IDX184—polymerase inhibitor by Idenix, GSK 625433—polymerase inhibitor by Glaxo Smith Kline, INX-189—polymerase inhibitor by Inhibitex, NM283—polymerase inhibitor by Idenix, HCV796—polymerase inhibitor by Wyeth, GL60667 and GS9190—polymerase inhibitors by Gilead, PF-00868554 0 polymerase inhibitor by Pfizer, VCH759, VCH916, VX222 and VX759—polymerase inhibitors by Virochem, IDX184 and IDX375—polymerase inhibitors by Idenix, BMS650032—polymerase inhibitor by Bristol Myers Squibb; (2) protease inhibitors including for example: saquinavir (FOROVASE®/INVIRASE®), ritonavir (NORVIR®), indinavir (CRIXIVAN®), nelfinavir (VIRACEPT®), amprenavir (AGENERASE®), lopinavir (KALETRA®), atazanavir (REYATAZ®), fosamprenavir (LEXIVA®), tipranavir (APTIVUS®), darunavir (PREZISTA®), telapravir (VX-950); the second generation HCV protease inhibitors by Vertex Pharmaceuticals—VX-500 and VX-813; the NS3/4A protease inhibitor by Intermune/Roche—ITMN-191/R-7227, boceprevir, the protease inhibitor by Schering-Plough—SCH 503034, the HCV NS3/4A protease inbihitor by Medivir/Tibotec—TMC435/TMC435350, ACH-1625 protease inhibitor by Achillion. Pharmaceuticals, ACH-806—protease inhibitor by Achillion/Gilead, BI201335 and BILN 2061—protease inhibitors by Boehringer Ingelheim, SCH 900518/SP900518 (narlaprevir)—protease inhibitor by Schering-Plough, MK-7009—protease inhibitor by Merck, BMS-650032, BMS-790052 and BMS-791325—protease inhibitors by Bristol Myeres Squibb, R7227—protease inhibitor by Roche, PHX1766—protease inhibitor by Phenomix, AVL-181—protease inhibitor by Avila Therapeutics, biliverdin, CTS-1027—protease inhibitor by Roche Biosciences, VX985—protease inhibitor by Vertex, VCH-759 and VCH-917—protease inhibitors by Virochem/Vertex, IDX-136 and 316—protease inhibitors by Idenix, ABT-450—protease inhibitor by Abbott, VBY 376—protease inhibitor by Virobay; (3) integrase inhibitors including for example: raltegravir (ISENTRESS®), elvitegravir; (4) combo therapies of nucleoside analog/nucleotide analog inhibitors, atripla (tenofovir+embricitabine+efavirenz), combivir (lamivudein+zidovudine), (5) entry or fusion inhibitors including for example: maraviroc, enfuvirtide, docosanol, anti-CD4 antibody, anti-gp120 antibody, anti-CCR5 antibody, HCV NS5a antagonists: (a) A-831, A-689 and AZD 2836 by Arrow Therapeutics, (b) BMS-790052 and BMS-824393 by Bristol Myers Squibb, (c) GSK-625433 by Glaxo Smith Kline, (d) NS4a antagonists ACH-1095; (5) maturation inhibitors including for example: bevirimat and vivecon; (6) viral release inhibitors including for example: zanamivir (RELENZA®), oseltamivir (TAMIFLU®), arbidol; (7) immune response enhancers, including for example interferon-α (E.g., BLX-883 and BLX 883 CR by Biolex Therapeutics, belerofon by Nautilus Biotech, long-acting IFN-α, IFN-α SR by LG Life Sciences, long acting IFN-α2b CR and IFN-α2b XL by Flamel Technologies, pegylated IFN-α (E.g., PEG-IFN-α-2a, PEGASYS®; PEG-IFN-α2b, PEGINTRON®), IFN-α2b-Human serum albumin fusion protein (ALBUFERON®); interferon-β, including IFN-β-1b (BETASERON®), interferon-γ, interferon-λ, pegylated interferon-λ

(e.g., PEG-rIL-29 by ZymoGenetics/Novo Nordisk), interferon-ω/leukocyte II interferon (E.g., Intarcia Therapeutics), toll-like receptor 7 agonists including imiquimod, isatoribine and prodrug variants thereof (e.g., ANA-975 and ANA-971) by Anadys Pharmaceuticals, oglufanide (IM862, L-Glu-L-Trp-OH) and lipid- or -glycosylconjugated variants thereof by Implicit Bioscience, NOV-205 (E.g., Molixan®—a peptidic antiviral by Novelos Therapeutics, Inc.), the antiviral EHC18 by Enzo Biochem, gamma-D-glutamyl-L-tryptophan (E.g., SCV-07, SciClone Pharmaceuticals/Verta), aloferon (E.g., aloferon-1-HGVSGHGQHGVHG, aloferon-2-GVSGHGQHGVHG), CPG 10101—a TLR-9 agonist by Coley Pharmaceuticals/Actilon; (8) anti-viral synergistic enchancers, i.e., little or no anti-viral properties alone, but enhances the effect of other anti-virals—e.g., choroquine, grapefruit juice, hydroxyurea, leflunomide, mycophenolic acid, resveratrol, ritonavi; as well as other anti-viral drugs such as amantadine, edoxudine, famciclovir (FAMVIR®), penciclovir, fascarnet, fosfonet, ganciclovir (CYTOVENE®, CYMEVENE®, VITRASERT®), gardasil, ibacitabine, immunovir, moroxydine, nexavir, peramivir, pleconaril, podophyllotoxin, ribavirin, rimantadine, trifluridine, trizivir, tromantadine, truvada, valaciclovir, valganciclovir, vidarabine, and interferon enchancers such as EMZ702 by Transition Therapeutics, histamine dihydrochloride (E.g., Ceplene®+IFN-α); and (9) miscellaneous or unclassified anti-virals such as: KPE-02003002 (Artenimol) by Kemin Pharmaceuticals, mitoquinone—a coenzyme Q10 anti-oxidant agonist by Antipodean Pharmaceuticals, alpha-glucosydase I inhibitors (E.g., MX-3253-celgosivir by Migenix Pharmaceuticals, castanospermine, glucocorticoid antagonists (e.g., HCV IRES inhibitors, mifepristone, VGX-410C by VGX Pharmaceuticals), hepatic agonists (E.g., PYN17 by Phynova Pharmaceuticals), anti-viral agents derived from traditional herbal therapies, e.g., PYN18 by Phynova Pharmaceuticals, caspase inhibitors (E.g., LB-84451—by LG Life Sciences, emricasan—PF-03491390/IDN-6556 by Pfizer), cyclosporine analogs that inhibit viral replication by preventing binding to cyclophilin A (E.g., SDZ NIM 911 by Novartis, Debio-025 by Debiopharm), The term "anti fungal agent" includes any molecule that inhibits or abolishes the growth, morbity and/or survival of fungi. This includes for example, (1) polyene antifungals such as natamyin, rimocidin, filipin, nystatin, Amphotericin B, candicin; (2) imidazoles such as miconazole, ketoconazole (LOTRIMIN®), econazole, bifonazole, butoconazole, fenticonazole, isoconazole, oxiconazole, sertaconazole (ERTACZO®), sulconazole, tioconazole, (3) triazoles such as fluconazole, itraconazole, isavuconazole, ravuconazole posaconazole, voriconazole, terconazole; (4) allylamines such as terbinafine (LAMISIL®), amorolfine, naftifine (Naftin®), butenafine (LOTRIMIN ULTRA®); (5) Echinocandins, such as anidulafungin, caspofungin, micafungin, and other substances with anti-fungal properties such as benzoic acid, cicclopix, flucytosine, griseofulvin, gentian violet, haloprogin, tolnaftate (TINACTIN®, DESENEX®, AFTATE®), undecylenic acid, tea tree oil—ISO 4730 (Oil of Melaleuca, Terpinen-4-ol type) citronella oil, lemon grass, orange oil, palmarosa oil, patchouli, lemon myrtle, neem seed oil, Coconut Oil.

The term "anti-protozoan agent" or "anti-protozoal agent" includes any molecule that inhibits or abolishes the growth, morbidity and/or survival or protozoan organisms. Example anti-protozoan agents include, (1) anti-malarial agents, E.g., quinine, quinimax, quinidine, quinimax, chloroquine (ARALEN®), Hydroxycloroquine (PLAQUENIL®), amodiaquine, pyrimethamine (DARAPRIM®), sulphadoxine, proguanil, mefloquine (LARIAM®), halofantrine, primaquine, artemesinin and it derivatives (e.g., artemether, artensunate, dihydroartemisinin, arteether), clindamycin and combinations thereof; (2) protease inhibitors, and the drugs, benznidaole, buparvaquone, carbarsone, clioquinol, disulfuram, eflornithine, emetine, furazolidone, meglumine antimoniate, melarsoprol, metronidazole (FLAGYL®), miltefosine, nifurtimox, nitazoxanide, ornidazole, paromomycin sulfate, pentamidine, pyrimethamine (DARAPRIM®), secnidazole, tinidazole.

The term "vaccine" as used herein includes any nonpathogenic immunogen that, when inoculated into a host, induces protective immunity against a specific pathogen. Vaccines can take many forms. Vaccines can be whole organisms that share important antigens with the pathogem, but are not pathogenic themselves (e.g., cowpox). Vaccines can also be prepared from killed (e.g., Salk polio vaccine) or attenuated (lost ability to produce disease—e.g., Sabin polio vaccine). Vaccines can also be prepared from purified macromolecules isolated from the pathogenic organism. For example, toxoid vaccines (e.g., tetanus and diphtheria) containing the inactive form of soluble bacterial toxin—resulting in the production of anti-toxin antibodies, but not immunity to the intact bacteria. Subunit vaccines (e.g., Hepatitis B) contain only a single immunogenic protein isolated from the pathogen of interest. Hapten conjugate vaccines attaches certain carbohydrate or polypeptide epitopes isolated from the pathogen of interest to immunogenic carriers, such as tetanus toxoid. These strategies essentially use the epitopes as haptens to induce antibody production, which then recognize the same epitope in the native pathogen. However, to be maximally effective, such vaccines must incorporate both B- and T-cell cell epitopes, and the T-cell epitopes must be chosen to ensure that they can be recognized, presented and responded to by the immune systems of the host individuals.

DNA vaccines exploit the ability of host cells to take up and express DNA encoding pathogenic proteins that is injected intramuscularly.

Examples of anti-viral vaccines that can be used in combination with the anti-PD-L1 antibodies for the methods described herein include: HCV vaccine (virasome) by Pevion Biotech., TG4040 (MVA-HCV by Transgene viron designed to enhance cellular (Cytotoxic T lymphocytes CD4+ and CD8+) immune response against NS3, NS4 and NS5B, CHRONVAC®—a codon-optimized NS3/4a DNA vaccine by Inovio Biomedical, HCV/CpG vaccines by Novartis, GI-5005—an HCV vaccine by Globeimmune, IC41 a mixture of synthetic peptides having HCV CD4 and CD8 T epitopes in combination with poly-L-arginine by Intercell.

Host responses to immunogens can be enhanced if administered as a mixture with adjuvants. Immune adjuvants function in one or more of the following ways: (1) prolonging retention of the immunogen, (2) increased effective size of the immunogen (and hence promoting phagocytosis and presentation to macrophages), (3) stimulating the influx of macrophage or other immune cells to the injection site, or (4) promoting local cytokine production and other immunologic activities. Example adjuvants include: complete Freund's adjuvant (CFA), aluminum salts, and mycobacterial derived proteins such as muramyl di- or tri-peptides.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

An "isolated" antibody is one that has been identified, separated and/or recovered from a component of its production environment (E.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993);

U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332: 323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVESGGGLVQPGGSL-RLSCAAS (HC-FR1) (SEQ ID NO:4), WVRQAPGK-GLEWV (HC-FR2), (SEQ ID NO:5), RFTISADTSKNTAY-LQMNSLRAEDTAVYYCAR (HC-FR3, SEQ ID NO:6), WGQGTLVTVSA (HC-FR4), (SEQ ID NO:7).

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSLSASVGDRVTITC (LC-FR1) (SEQ ID NO:11), WYQQKPGKAPKLLIY (LC-FR2) (SEQ ID NO:12), GVPSRFSGSGSGTDFTLTISS-LQPEDFATYYC (LC-FR3) (SEQ ID NO:13), FGQGT-KVEIKR (LC-FR4) (SEQ ID NO:14).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154 (7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≦1 µM, ≦100 nM, ≦10 nM, ≦1 nM, or ≦0.1 nM. In certain embodiments, an antibody specifically binds to an epitope on a protein that is conserved among the protein from different species. In another embodiment, specific binding can include, but does not require exclusive binding.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the invention block the signaling through PD-1 so as to restore a functional response by T-cells from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "solid phase" describes a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments of the invention, effector function is eliminated through a mutation in the constant region that eliminated glycosylation, e.g., "effector-less mutation." In one aspect, the effector-less mutation is an N297A or DANA mutation (D265A+N297A) in the CH2 region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycolsylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Effector cells" are leukocytes which express one or more FcRs and perform effector functions. In one aspect, the effector cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source, e.g., blood. Effector cells generally are lymphocytes associated with the effector phase, and function to produce cytokines (helper T cells), killing cells in infected with pathogens (cytotoxic T cells) or secreting antibodies (differentiated B cells).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

The N-glycosylation site in IgG is at Asn297 in the CH2 domain. The present invention also provides compositions of an antigen-binding, humanized antibody having an Fc region with reduced or no effector function. One manner in which this can be accomplished is an A297N substitution, which has previously been shown to abolish complement binding and effector function ("effector-less Fc mutant") in an anti-CD20 antibody. Idusgie et al., supra. As a result of this mutation, the production of anti-PD-L1 antibodies of the present inventions containing this Fc mutation in mammalian cells such as CHO will not have any glycosylation and, which in turn results in reduced or minimal effector function. Alternatively, antibody effector function may be eliminated without CH2 substitution by expression in non-mammalian cells such as *E. Coli*.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

The "Kd" or "Kd value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol. Biol* 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the Kd is measured by using surface-plasmon resonance assays using a BIACORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µL/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.) at 25° C. with immobilized antigen CM5 chips at about 10 response units (RU). Briefly, carboxymethylated dextran biosensor ships (CM5, BIAcore Inc.) are activated with N-ethyl-N'-(3-dimethylamino propyl)-carbodiimide hydrochloride (ECD) and N-hydroxysuccinimide (NHS) according to the supplier's instructions. Antigen is diluted with 10 mM sodium acetate, ph 4.8, into 5 mg/ml 0.2 mM) before injection at a flow rate of 5 ml/min. to achieve approximately 10 response units (RU) of coupled protein. Following the injection of antigen, 1M ethanolamine is added to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol. Biol* 293:865-881. However, if the on-rate exceeds $10^6 M^{-1} S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, authored by Genentech, Inc. The source code of ALIGN-2 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

An "isolated" nucleic acid molecule encoding the antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "epitope tagged" when used herein refers to a chimeric polypeptide comprising a polypeptide or antibody described herein fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the extracellular or PD-1 binding portions of PD-L1 or PD-L2, or vice versa, fused to a constant domain of an immunoglobulin sequence.

A "fusion protein" and a "fusion polypeptide" refer to a polypeptide having two portions covalently linked together, where each of the portions is a polypeptide having a different properly. The property may be a biological property, such as activity in vitro or in vivo. The property may also be simple chemical or physical property, such as binding to a target molecule, catalysis of a reaction, etc. The two portions may be linked directly by a single peptide bond or through a peptide linker will be in reading frame with each other.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. subcutaneous administration) to a patient to be treated with the protein of interest and, in certain embodiments of the invention, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzensulfonic, napthalene-2-sulphonic, p-toluenesulphonic, camphorsulphonic, 4-methylbicyclo [2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine. Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

"Treatment" refers to clinical intervention designed to alter the natural course of the individual or cell being treated, and can be performed either for prophylaxis or during the course of clinical pathology. Desirable effects of treatment include preventing occurrence or recurrence of disease, preventing metastasis, decreasing the rate of disease progression, ameliorating or palliating the disease state, and remission or improved prognosis. In some embodiments, antibodies of the invention are used to delay development of a disease or disorder. A subject is successfully "treated", for example, using the apoptotic anti-PD-L1 antibodies of the invention if one or more symptoms associated with a T-cell dysfunctional disorder is mitigated.

An "effective amount" refers to at least an amount effective, at dosages and for periods of time necessary, to achieve the desired or indicated effect, including a therapeutic or prophylactic result. For example, an effective amount of the anti-PD-L1 antibodies of the present invention is at least the minimum concentration that results in inhibition of signaling from PD-L1, either through PD-1 on T-cells or B7.1 on other APCs or both.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. For example, a therapeutically effective amount of the anti-PD-L1 antibodies of the present invention is at least the minimum concentration that results in inhibition of at least one symptom of a T cell dysfunctional disorder.

A "prophylactically effective amount" refers to an amount effective, at the dosages and for periods of time necessary, to achieve the desired prophylactic result. For example, a prophylactically effective amount of the anti-PD-L1 antibodies of the present invention is at least the minimum concentration that prevents or attenuates the development of at least one symptom of a T cell dysfunctional disorder.

"Chronic" administration refers to administration of the medicament(s) in a continuous as opposed to acute mode, so as to main the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, horses, rabbits, cattle, pigs, hamsters, gerbils, mice, ferrets, rats, cats, etc. Preferably, the mammal is human.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

The term "about" as used herein refers to the usual error range for the respective value readily known to the skilled person in this technical field.

An "autoimmune disorder" is a disease or disorder arising from and directed against an individual's own tissues or organs or a co-segregation or manifestation thereof or resulting condition therefrom. Autoimmune diseases can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Preferred such diseases include autoimmune rheumatologic disorders (such as, for example, RA, Sjögren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjögren's syndrome, Graves' disease, IDDM, pernicious anemia, thyroiditis, and glomerulonephritis.

The term "cytotoxic agent" as used herein refers to a substance that inhibits or prevents the function of cells and/or causes destruction of cells. The term includes radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), and toxins such as small-molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al., *Angew. Chem. Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. A particularly preferred chemotherapeutic agent useful in combination with the anti-PD-L1 antibodies of the invention, especially in the treatment of tumor immunity is gemcitabine.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

A "growth-inhibitory agent" refers to a compound or composition that inhibits growth of a cell, which growth depends on receptor activation either in vitro or in vivo. Thus, the growth-inhibitory agent includes one that significantly reduces the percentage of receptor-dependent cells in S phase. Examples of growth-inhibitory agents include agents that block cell-cycle progression (at a place other than S phase), such as agents that induce G1 arrest and M-phase arrest. Classical M-phase blockers include the vincas and vinca alkaloids (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb).

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-12, IL-13, IL-15 ... IL-35, including PROLEUKIN® rIL-2; a tumor-necrosis factor such as TNF-α or TNF-β; and other polypeptide factors including LIF and kit ligand (KL), while the term "interleukin" has now essentially become a synonym for cytokine. As used herein, the term cytokine includes proteins from natural sources or from recombinant cell culture and biologically active equivalents of the native-sequence cytokines, including synthetically produced small-molecule entities and pharmaceutically acceptable derivatives and salts thereof. Cytokines can be classified on the proximal location of the intended target, wherein autocrine refers to action on the same cell from which it is secreted, paracrine refers to action restricted to the immediate vicinity into which the cytokine is secreted, and endocrine refers to action in distant regions of the body. Immune cytokines can also be classified by whether they enhance a type I response, (e.g., IFN-γ, TGF-β etc), which favor cellular immunity or a type II response (IL-4, IL-10, IL-13, etc.), which favor antibody or humoral immunity. Immune cytokines play roles in co-stimulation, maturation, proliferation, activation, inflammation, growth, differentiation, cytokines production and secretion, survival of various immune cells.

The term "hormone" refers to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; hormone-replacement therapy; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

III. Modes for Carrying Out the Invention

A. Humanization Using Phage Display

The hypervariable region-grafted variants described herein were generated by Kunkel mutagenesis of nucleic acid encoding the human acceptor sequences, using a separate oligonucleotide for each hypervariable region. Kunkel et al., *Methods Enzymol.* 154:367-382 (1987). Appropriate changes can be introduced within the framework and/or hypervariable region using routine techniques, to correct and re-establish proper hypervariable region-antigen interactions.

Phage(mid) display (also referred to herein as phage display) can be used as a convenient and fast method for generating and screening many different potential variant antibodies in a library generated by sequence randomization. However, other methods for making and screening altered antibodies are available to the skilled person.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage (mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

| IUB CODES | | |
|---|---|---|
| G (Guanine) | Y (C or T) | H (A or C or T) |
| A (Adenine) | M (A or C) | B (C or G or T) |
| T (Thymine) | K (G or T) | V (A or C or G) |
| C (Cytosine) | S (C or G) | D (A or G or T) |
| R (A or G) | W (A or T) | N (A or C or G or T) |

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA,* 75:5765 (1978).

The DNA template is generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate a single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a $^{32}$-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease to cut at other than the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously, the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.,* 153:3 (1987). Thus, the DNA that is to be mutated must be inserted into one of these vectors in order to generate a single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides.

The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids. Antibody selectants that meet the desired criteria, as selected through appropriate screening/selection steps can be isolated and cloned using standard recombinant techniques.

B. Recombinant Preparation

The invention also provides an isolated nucleic acid encoding anti-PD-L1 antibodies, vectors and host cells comprising such nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

1. Antibody Production in Prokaryotic Cells
a) Vector Construction

Polynucleotide sequences encoding polypeptide components of the antibodies of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components. One technique for modulating translational strength is disclosed in Simmons et al., U.S. Pat. No. 5,840, 523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

b) Prokaryotic Host Cells.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus.* In one embodiment, gram-negative cells are used. In one embodiment, *E. coli* cells are used as hosts for the invention. Examples of *E. coli* strains include strain W3110 (Bachmann, *Cellular and Molecular Biology,* vol. 2 (Washington, D.C.: American Society for Microbiology, 1987), pp. 1190-1219; ATCC Deposit No. 27,325) and derivatives thereof, including strain 33D3 having genotype W3110 ÿfhuA (ÿtonA) ptr3 lac Iq lacL8 ÿompTÿ(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Antibody Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli,* the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

The expressed antibody proteins of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance,* 2:63-72 (1996).

*E. coli* strains deficient for proteolytic enzymes and transformed with plasmids overexpressing one or more chaperone proteins may be used as host cells in the expression system encoding the antibodies of the invention.

d) Antibody Purification

The antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 411(D cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the antibody of interest is recovered from the solid phase by elution.

2. Antibody Production in Eukaryotic Cells

For Eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the invention.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the invention, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the antibody encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired antibody sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucletotide. A the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody polypeptide.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the antibody-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences. Examples of useful mammalian host cellines are h) Culturing the Host Cells The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABXTMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

C. Antibody Preparation

1) Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride, $SOCl_2$, or $R^1N\!=\!C\!=\!NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

2) Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.,* 133: 3001 (1984); Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.,* 5:256-262 (1993) and Pliickthun, *Immunol. Revs.* 130:151-188 (1992).

In a further embodiment, antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3) Humanized Antibodies

The antibodies of the invention may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) (HVR as used herein) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321:522-525 (1986); Riechmann et al., Nature 332:323-327 (1988); Verhoeyen et al., Science 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies. Carter et al., Proc. Natl. Acad. Sci. USA, 89:4285 (1992); Presta et al., J. Immunol., 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent(s) in order to generate an immunoconjugate. Alternatively, the humanized antibody may be an intact antibody, such as an intact IgG1 antibody.

4) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); U.S. Pat. No. 5,591,669 and WO 97/17852.

Alternatively, phage display technology can be used to produce human antibodies and antibody fragments in vitro, from immunoglobulin variable (V) domain gene repertoires from unimmunized donors. McCafferty et al., Nature 348: 552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Curr. Opin Struct. Biol. 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol. 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human antibodies may also be generated in vitro by activated B cells (see U.S. Pat. Nos. 5,567,610 and 5,229,275).

5) Antibody Fragments

In certain circumstances there are advantages to using antibody fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, e.g., Morimoto et al., *J Biochem Biophys. Method.* 24:107-117 (1992); and Brennan et al., *Science* 229:81 (1985)). However, these fragments can now be produced directly by recombinant host cells. Fab, Fv and scFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ with increase in vivo half-life is described in U.S. Pat. No. 5,869,046. In other embodiments, the antibody of choice is a single chain Fv fragment (scFv). See WO 93/16185; U.S. Pat. No. 5,571,894 and U.S. Pat. No. 5,587,458. The antibody fragment may also be a "linear antibody", e.g., as described in U.S. Pat. No. 5,641,870. Such linear antibody fragments may be monospecific or bispecific.

6) Antibody Dependent Enzyme-Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anticancer drug 5-fluorouracil; proteases, such as *serratia* protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin Vamidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The above enzymes can be covalently bound to the polypeptide or antibodies described herein by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604-608 (1984)).

7) Bispecific and Polyspecific Antibodies

Bispecific antibodies (BsAbs) are antibodies that have binding specificities for at least two different epitopes, including those on the same or another protein. Alternatively, one arm can bind to the target antigen, and another arm can be combined with an arm that binds to a triggering molecule on a leukocyte such as a T-cell receptor molecule (e.g., CD3), or Fc receptors for IgG (FcγR) such as FcγR1 (CD64), FcγRII (CD32) and FcγRIII (CD16), so as to focus and localize cellular defense mechanisms to the target antigen-expressing cell. Such antibodies can be derived from full length antibodies or antibody fragments (e.g. F(ab')$_2$ bispecific antibodies).

Bispecific antibodies may also be used to localize cytotoxic agents to cells which express the target antigen. Such antibodies possess one arm that binds the desired antigen and another arm that binds the cytotoxic agent (e.g., saporin, anti-interferon-α, vinca alkoloid, ricin A chain, methotrexate or radioactive isotope hapten). Examples of known bispecific antibodies include anti-ErbB2/anti-FcgRIII (WO 96/16673), anti-ErbB2/anti-FcgRI (U.S. Pat. No. 5,837,234), anti-ErbB2/anti-CD3 (U.S. Pat. No. 5,821,337).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA,* 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

8) Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain (s) comprise two or more variable domains. For instance, the polypeptide chain(s) may comprise VD1-(X1)$_n$-VD2-(X$_2$)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

9) Heteroconjugate Antibodies

Heteroconjugate antibodies are also within the scope of the present invention. Heteroconjugate antibodies are composed of two covalently joined antibodies. For example, one of the antibodies in the heteroconjugate can be coupled to avidin, the other to biotin. Such antibodies have, for example, been proposed to target immune system cells to unwanted cells, U.S. Pat. No. 4,676,980, and for treatment of HIV infection. WO 91/00360, WO 92/200373 and EP 0308936. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

10) Effector Function Engineering

It may be desirable to modify the antibody of the invention with respect to Fc effector function, e.g., so as to modify (e.g., enhance or eliminate) antigen-dependent cell-mediated cyotoxicity (ADCC) and/or complement dependent cytotoxicity (CDC) of the antibody. In a preferred embodiment, Fc effector function of the anti-PD-L1 antibodies is reduced or eliminated. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

11) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells in *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table A below under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |

TABLE A-continued

Amino Acid Substitutions

| Original Residue | Exemplary Substitutions | Preferred Substitutions |
|---|---|---|
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its target (e.g., PD-L1, B7.1). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants to the antibodies of the invention are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant versions.

12) Other Antibody Modifications

The antibodies of the present invention can be further modified to contain additional nonproteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

D. Pharmaceutical Formulations

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

When the therapeutic agent is an antibody fragment, the smallest inhibitory fragment which specifically binds to the binding domain of the target protein is preferred. For example, based upon the variable region sequences of an antibody, antibody fragments or even peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90: 7889-7893 [1993]).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition, supra.

Stability of the proteins and antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Example anions that can form water soluble salts with the above polyvalent metal cations include those formed from inorganic acids and/or organic acids. Such water-soluble salts have a solubility in water (at 20° C.) of at least about 20 mg/ml, alternatively at least about 100 mg/ml, alternatively at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

E. Methods of Treatment

For the prevention or treatment of disease, the appropriate dosage of an active agent, will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

In a particular embodiment, the invention relates to costimulation resulting from attenuating signaling through PD-1, specifically by the application of PD-L1 antibodies that prevent binding to PD-1 and/or B7.1, as well to the therapeutic treatment of T-cell dysfunctional disorders.

1. Infections

PD-1 and its ligands ("PD-1:PD-L") plays an important role in regulating immune defenses against pathogens that cause acute and chronic infections. PD-1:PD-L signaling plays a key role in regulating the balance between an effective antimicrobial immune defense and immune-mediated tissue damage. For example, while PD-1 knock-out mice clear adenovirus infection more rapidly than their wild type counterparts, they develop more severe hepatocellular injury. Iwai et al., *J. Exp. Med.* 198: 39-50 (2003). In a mouse model of herpes stromal keratitis, blocking anti-PD-L1 antibody exacerbated keratitis, increasing HSV-1 specific effector CD4 T cell expansion and IFN-γ production and survival. Jun et al., *FEBS Lett.* 579: 6259-64 (2005).

Microorganisms that cause chronic infection have exploited the PD-1:PD-L signaling pathway to evade the host immune responses that results in chronic infections. Viruses that cause chronic infection can render virus-specific T cells non-functional and thereby silence the antiviral T cell response. Barber et al., Nature 439: 682-87 (2006); Wherry et al., *J. Virol.* 78: 5535-45 (2004). Exhaustion of T cells or anergy, of $CD8^+$ T cells is an important reason for ineffective viral control during chronic infections and is characteristic of chronic LCMV infections in mice as well as HIV, HBV, HCV and HTLV infection in human and SIV infection in primates. There appears to be a hierarchical, progressive loss of function within the phenotype of exhausted virus-specific $CD8^+$ T cells, with cytotoxicity and IL-2 production lost first, followed by effector cytokine production.

PD-1 is upregulated upon activation, and expression is maintained at a high level by exhausted $CD8^+$ T cells in mice with LCMV chronic infection. Barber et al., supra. Administration of antibodies that blocked PD-1: PD-L1 binding resulted in enhanced T cell responses and a substantial reduction in viral burden. In persistently infected mice with ineffective $CD4^+$ $T_H$ response, blockade of PD-1:PD-L1 restored $CD8^+$ T cells from an dysfunctional state resulting in proliferation, secretion of cytokines, killing of infected cells, and decreased viral load, strongly suggesting a therapeutic approach for the treatment of chronic viral infections.

As a result of the role of PD-1:PD-L in LCMV, strong interest has been shown in targeting this pathway to the treatment of chronic infection in humans. PD-1 expression is high on HIV-specific [Petrovas et al., *J. Exp. Med.* 203: 2281-92 (2006); Day et al., Nature 443: 350-54 (2006); Traumann et al., *Nat. Med.* 12: 1198-202 (2006)], HBV-specific [Boettler et al., *J. Virol.* 80: 3532-40 (2006); Boni et al., *J. Virol.* 81: 4215-25 (2007)], and HCV-specific T cells [Urbani et al., *J. Virol.* 80: 11398-403 (2006)]. PD-L1 is also upregulated on peripheral blood $CD14^+$ monocytes and myeloid DC's in patients with chronic HBV infection [Chen et al., *J. Immunol.* 178: 6634-41 (2007); Geng et al., *J. Viral Hepat.* 13: 725-33 (2006)], and on CD14+ cells and T cells in HIV patients [Trabattoni et al., Blood 101: 2514-20 (2003)]. Blocking PD-1:PD-L1 interactions in vitro reverses the exhaustion of HIV-specific, HBV-specific, HCV-specific and SIV-specific CD8+ and CD4+ T cells and restores proliferation and cytokine production. Petrovas et al., J. Exp. Med. 203: 2281-92 (2006); Day et al., supra; Trautmann et al., supra; Boni et al., supra; Urbani et al., supra; Velu et al., *J. Virol.* 81: 5819-28 (2007).

The degree of PD-1 expression may also be a useful diagnostic marker on virus-specific $CD8^+$ T cells to indicate the degree of T cell exhaustion and disease severity. The level of PD-1 expression on HIV-specific $CD8^+$ T cells correlates with viral load, declining $CD4^+$ counts, and decreased capacity of $CD8^+$ T cells to prolifeate in response to HIV antigen in vitro. Corresponding to in vivo observations, there is a direct correlation between PD-1 expression on HIV-specific CD4+ T cells and viral load. D'Souza et al., *J. Immunol.* 179: 1979-87 (2007). Long-term nonprogressors have functional HIV-specific memory $CD8^+$ T cells with markedly lower PD-1 expression, in contrast to typical progressors who express significantly upregulated PD-1, which correlates with reduced CD4+ T cell number, decreased CD4+ T cell number, decreased HIV-specific effector memory CD8$^+$ T cell function, and elevated plasma viral load. Zhang et al., *Blood* 109: 4671-78 (2007).

The PD-1:PD-L pathway has also been implicated in the chronicity of bacterial infections. *Helicobacter pylori* causes chronic gastritis and gastroduodenal ulcers and is a risk factor for the development of gastric cancer. During a *H. pylori* infection, T cell responses are insufficient to clear infection, leading to persistent infection. Following exposure to *H. pylori* in vitro or in vivo, PD-L1 is upregulated on gastric epithelial cells. Gastric epithelial cells express MHC class II molecules and are thought to play in important APC function during *H. pylori* infection. Anti-PD-L1 antibodies that block PD-1 to PD-L1 interaction enhance T cell proliferation and IL-2 production in cultures of gastric epithelial cells explosed to *H. pylori* and CD4 T cells. Blocking PD-L1 with either antibodies or siRNA prevented the generation of the regulatory T cells, suggesting that PD-L1 may promote T cell suppression and persisting infections by controlling the dynamic between regulatory and effector T cells during *H. pylori* infection. Beswick et al., *Infect. Immun.* 75: 4334-41 (2007).

Parasitic worms have also exploited the PD-1:PD-L1 pathway to induce macrophages that suppress the immune response. During *Taenia crassiceps* (i.e., tapeworm) infections in mice, PD-1 and PD-L2 are upregulated on activated macrophages, and CD4+ T cells express PD-1. Blockade of PD-1, PD-L1 or PD-L2 significantly decreased suppression of in vitro T cell proliferation by macrophages from tapeworm infected mice. Terrazas et al., *Int. J. Parasitol.* 35: 1349-58 (2005). During *Shistosoma mansoni* infection in mice, macrophages express high levels of PD-L1 and more modest levels of PD-L2. Anti-PD-L1 removed the ability of these macrophages to suppress T cell proliferation in vitro, whereas anti-PD-L2 had no effect. PD-L1 expression on macrophages from infected mice declines after 12 weeks of infection, correlating with a break in T cell anergy. Smith et al., *J. Immunol.* 173: 1240-48 (2004).

2. Tumor Immunity

Empirical evidence for tumor immunity includes (i) the observance of spontaneous remission, (ii) the presence of detectable, but ineffective host immune response to tumors, (iii) the increased prevalence of primary and secondary malignancies in immunodeficient patients, (iv) the detection of increased levels of antibodies and T-lymphocytes in tumor patients, and (v) the observation that test animals can be immunized against various types of tumors.

Studies have shown that most human tumors express tumor-associated antigens (TAAs) that can be recognized by T cells and thus are potentially capable of inducing immune response. Boon et al., *Immunol. Today* 16:334-336 (1995). Early phase clinical trials have been initiated by vaccinating cancer patients with TAA or professional antigen-presenting cells pulsed with TAA. Dudley et al., *Science* 298: 850-854 (2002); Gajewski et al., *Clin. Cancer Res.* 7: 895s-901s (2001); Marincola et al., *Adv. Immunol.* 74: 181-273 (2000); Peterson et al., *J. Clin. Oncol.* 21: 2342-2348 (2003). Induction of tumor antigen-specific CD8+ T cells has been achieved in many of these trials. Mackensen et al., *Eur. Cytokine Netw* 10: 329-336 (1999); Peterson et al., supra. Adoptive transfer of tumor antigen-specific T cells into patients also has been pursued and has revealed homing of the expanded cytotoxic T lymphocytes (CTLs) to tumor sites. Meidenbauer et al., *J. Immunol.* 170: 2161-2169 (2003). However, despite tumor infiltration of immune effector cells, tumor growth was seldom controlled.

It is well established that the tumor microenvironment can protect tumor cells from immune destruction. Ganss et al., *Cancer Res.* 58: 4673-4681 (1998); Singh et al., *J. Exp. Med.* 175: 139-146 (1992). Soluble factors, as well as membrane-bound molecules including transforming growth factor β (TGF-β), interleukin (IL)-10, prostaglandin $E_2$, FASL, CTLA-4 ligands, tumor necrosis factor-related apoptosis-inducing ligand (TRAIL), and programmed death receptor ligand 1 (PD-L1, aka B7-H1) have been found to be expressed by tumors and are believed to mediate immune evasion. Thus, blockade of this negative immune regulatory signals on tumor cells is a promising approach to enhance tumor-specific CD8+ T-cell immunity in vivo.

PD-L1 expression on many tumors is a component to this suppression and may act in concert with other immunosuppressive signals. PD-L1 negatively regulates T-cell receptor signaling. PD-L1 expression has been shown in situ on a wide variety of solid tumors, including breast, lung, colon, ovarian, melanoma, bladder, liver, salivary, stomach, gliomas, thyroid, thymic, epithelian, head and neck cancers. Brown et al., *J. Immunol.* 170: 1257-66 (2003); Dong et al., *Nat. Med.* 8: 793-800 (2002); Hamanishi et al., *PNAS* 104: 3360-65 (2007); Strome et al., *Cancer Res.* 63: 6501-5 (2003); Inman et al., *Cancer* 109: 1499-505 (2007); Konishi et al., *Clin. Cancer Res.* 10: 5094-100 (2004); Nakanishi et al., *Cancer Immunol. Immunother.* 56: 1173-82 (2007); Nomi et al., *Clin. Cancer Res.* 13: 2151-57 (2004); Thompson et al., PNAS 101: 17174-79 (2004); Wu et al., *Acta Histochem.* 108: 19-24 (2006).

Immunological staining also reveals the expression of PD-1:PD-L expression on various cancers.

Interestingly, cancer has also been characterized as a chronic inflammatory disease. Coussens et al., *Nature* 420: 860-867 (2002). While up to 15% of cancers worldwide have a direct infectious origin [Kuper et al., *J. Intern. Med.* 248: 171-183 (2000)], many human tumors are related to chronic irritation and inflammation. Zou et al., *Ntu. Rev. Cancer* 5: 263-274 (2005).

Studies relating to PD-L1 expression on tumors to disease outcome show that PD-L1 expression strongly correlates with unfavorable prognosis in kidney, ovarian, bladder, breast, gastric, and pancreatic cancer, but perhaps not small cell lung cancer. Hamanishi et al., *Proc. Natl. Acad. Sci. USA* 104: 3360-65 (2007), Inman et al., *Cancer* 109: 1499-505 (2007), Konishi et al., *Clin. Cancer Res.* 10:5094-100 (2004); Nakanishi et al., *Cancer Immunol. Immunother.* 56: 1173-82 (2007); Nomi et al., *Clin. Cancer Res.* 13: 2151-57 (2007); Thompson et al., *Proc. Natl. Acad. Sci. USA* 101: 17174-79 (2004); Wu et al., *Acta Histochem.* 108: 19-24 (2006). In addition, these studies suggest that higher levels of PD-L1 expression on tumors may facilitate advancement of tumor stage and invasion into deeper tissue structures.

The PD-1:PD-L pathway may also play a role in hematologic malignancies. PD-1 or PD-L1 are rarely expressed B cell malignancies, but PD-L2 is overexpressed in mantle cell malignancies. Brown et al., supra; Rosenwald et al., *J. Exp. Med.* 198: 851-62 (2003). PD-L1 is expressed on multiple myeloma cells, but not on normal plasma cells. T cell expansion in response to myeloma cells is enhanced in vitro by PD-L1 blockade. Liu et al., *Blood* 110: 296-304 (2007). PD-L1 is expressed on some primary T cell lymphomas, particularly anaplastic large cell T lymphomas, and PD-L1 is expressed on the associated follicular dendritic cell network. Dorfman et al., *Am. J. Surg. Pathol.* 30: 802-10 (2006).

Microarray analysis further suggests that tumor-associated T cells are responding to PD-1 signals in situ in Hodgkin lymphoma. Chemnitz et al., *Blood* 110: 3226-33 (2007). PD-1 and PD-L1 are expressed on CD4$^+$ T cells in HTLV-1 mediated adult T cell leukemia and lymphoma. Shimauchi et al., *Int. J. Cancer* 121: 2585-90 (2007). These tumor cells are hyporesponsive to TCR signals, and PD-1 blockade increased their expression of TNF-α, but not IFN-γ. Studies in animal models demonstrate that PD-L1 expression on tumors inhibits T cell activation and lysis of tumor cells and in some cases leads to increased tumor-specific T cell death. Dong et al., *Nat. Med.* 8: 793-800 (2006); Hirano et al., *Cancer Res.* 65: 1089-96 (2005).

Thus, the suppression of signaling through PD-L1 with the anti-PD-L1 antibodies of the invention, so as to enhance T cell function, shows promise to attenuate tumor immunity, and as a result, can be effective treatment for cancer.

F. Combination Therapies

The method of the invention can be combined with known methods of treatment chronic infection or cancer, either as combined or additional treatment steps or as additional components of a therapeutic formulation.

1. Cancer

Enhancing the host's immune function to combat tumors is the subject of increasing interest. Conventional methods include (i) APC enhancement, such as (a) injection into the tumor of DNA encoding foreign MHC alloantigens, or (b) transfecting biopsied tumor cells with genes that increase the probability of immune antigen recognition (e.g., immune stimulatory cytokines, GM-CSF, co-stimulatory molecules B7.1, B7.2) of the tumor, (iii) adoptive cellular immunotherapy, or treatment with activated tumor-specific T-cells. Adoptive cellular immunotherapy includes isolating tumor-infiltrating host T-lymphocytes, expanding the population in vitro, such as through stimulation by IL-2 or tumor or both. Additionally, isolated T-cells that are dysfunctional may be also be activated by in vitro application of the anti-PD-L1 antibodies of the invention. T-cells that are so-activated may then be readministered to the host.

Traditional therapies for cancer include the following: (i) radiation therapy (e.g., radiotherapy, X-ray therapy, irradiation) or the use of ionizing radiation to kill cancer cells and shrink tumors. Radiation therapy can be administered either externally via external beam radiotherapy (EBRT) or internally via brachytherapy; (ii) chemotherapy, or the application of cytotoxic drug which generally affect rapidly dividing cells; (iii) targeted therapies, or agents which specifically affect the deregulated proteins of cancer cells (e.g., tyrosine kinase inhibitors imatinib, gefitinib; monoclonal antibodies, photodynamic therapy); (iv) immunotherapy, or enhancement of the host's immune response (e.g., vaccine); (v) hormonal therapy, or blockade of hormone (e.g., when tumor is hormone sensitive), (vi) angiogenesis inhibitor, or blockade of blood vessel formation and growth, and (vii) palliative care, or treatment directed to improving the quality of care to reduce pain, nausea, vomiting, diarrhea and hemorrhage. Pain medication such as morphine and oxycodone, anti-emetics such as ondansetron and aprepitant, can permit more aggressive treatment regimens.

In the treatment of cancer, any of the previously described conventional treatments for the treatment of cancer immunity may be conducted, prior, subsequent or simultaneous with the administration of the anti-PD-L1 antibodies of the invention. Additionally, the anti-PD-L1 antibodies of the invention may be administered prior, subsequent or simultaneous with conventional cancer treatments, such as the administration of tumor-binding antibodies (e.g., monoclonal antibodies, toxin-conjugated monoclonal antibodies) and/or the administration of chemotherapeutic agents.

2. Infection

In the treatment of infection (e.g., acute and/or chronic), administration of the anti-PD-L1 antibodies of the invention can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-PD-L1 antibodies of the invention to reactivate dysfunctional T-cells would be particularly useful to treat chronic infections, in particular those in which cell-mediated immunity is critical for complete recovery.

a. Bacteria

For infections resulting from a bacterial infection, the anti-PD-L1 antibodies of the invention may be combined by administration simultaneous with, prior or subsequent to standard therapies for treating bacterial infection. Bacterial infections are most commonly treated today with antibacterial antibiotics, but serum containing pathogen-specific antibodies from immunized hosts can also be effective.

Bacteria that are pathogenic as a result of the secretion of toxins, (toxogenic bacteria), vaccination with inactive toxin and/or the administration of therapeutic agents that block the toxicity of the toxins are usually effective (e.g., polyclonal serum, antibodies, antibiotics etc.). These organisms include *Clostridium* spp., *bacillus* spp., *Corynebacterium* spp., *Vibrio chloerae*, *Bordetella pertussis*, *Staphylococcus* spp., *Streptococcus* spp. Gram negative bacteria that also typically respond to such traditional therapies include Enterobacteria (E.g., *Escherichia*, *Klebsiella*, *Proteus*, *Yersinia*, *Erwina*), *Salmonella*, and *Pseudomonas aeruginosa*. Encapsulated bacteria, which are resistant to phagocytosis and opsonization, and thus often prevent a more significant challenge to immune clearance include: *Streptococcus* spp., *Haemophilus* spp. *Neisseria* spp., *Klebsiella* spp. and *Bacterioides fragillis*.

Bacteria that evade host defenses by invading cells so as to evade serum antibody and complement post a particular challenge. The clearance of these infections is almost entirely dependent upon T-lymphocyte mediated immunity, and are especially prone to becoming chronic infections. Specific examples include *Salmonella* (*S. typhi*, *S. choleraesuis*, *S. enteritidis*), *Legionella* spp., *Listeria* spp., *Brucella* spp. and *Mycobacterium*, including *M. tuberculosis*, *M. avium* and *M. leprae*.

Spirochetes, including *Treponema* spp., *Borrelia* spp. and *Leptospira* spp. are bacteria that cause persistent and latent infections. *Treponema palladium*, the pathogen causing the disease syphilis is a sexually transmitted disease which can have severe pathological consequences if left untreated. The disease progresses through distinct stages. The initial clinical stage is an ulcer or chancre at the site treponemal inoculation. Following this is a period of spirochetemia and metastatic distribution of microorganisms that continues, including repeating cycles of infection and resolution in a condition known as secondary syphilis. Following the resolution of secondary syphilis, the disease enters an asymptomatic latency period which may conclude in tertiary syphilis, which is a serious and often fatal condition. Tertiary syphilis may manifest in (i) the heart as aortisis with aneurysm formation and secondary aortic value insufficiency, (ii) central nervous system (tabes dorsalis, general paresis), (iii) eyes (interstitial keratitis) or (iv) ears (nerve deafness). Non-venereal forms resemble the clinical manifestations of the venereal forms, but are transmitted primary by direct contact and poor hygiene. They include yaws (*T. pallidum* subp. pertenue,) pinta (*T. carateum*) and bejel (*T. pallidum* subsp. endemicum).

Treatments for syphilis include penicillin (E.g., penicillin G.), tetracycline, doxycycline, ceftriaxone and azithromycin. The anti-PD-L1 antibodies of the invention would be most advantageously administered to treat the latent infection period.

Lyme disease, caused by *Borrelia burgdorferi* is transmitted into humans through tick bites. The disease manifests initially as a localized rash, followed by flu-like symptoms including malaise, fever, headache, stiff neck and arthralgias. Later manifestations can include migratory and polyarticular arthritis, neurologic and cardiac involvement with cranial nerve palsies and radiculopathy, myocarditis and arrhythmias. Some cases of Lyme disease become persistent, resulting in irreversible damage analogous to tertiary syphilis.

Current therapy for Lyme disease includes primarily the administration of antibiotics. Antibiotic-resistant strains may be treated with hydroxychloroquine or methotrexate. Antibiotic refractory patients with neuropathic pain can be treated with gabapentin. Minocycline may be helpful in late/chronic Lyme disease with neurological or other inflammatory manifestations. The anti-PD-L1 antibodies would be most advantageously administered to treat the latent infection period.

Other forms of borreliois, such as those resulting from *B. recurentis*, *B. hermsii*, *B. turicatae*, *B. parikeri*, *B. hispanica*, *B. duttonii* and *B. persica*, as well leptospirosis (E.g., *L. interrogans*), typically resolve spontaneously unless blood titers reach concentrations to cause intrahepatic obstruction.

b. Virus

For infections resulting from viral causes, the anti-PD-L1 antibodies of the invention may be combined by application simulatenous with, prior to or subsequent to application of standard therapies for treating viral infections. Such standard therapies vary depending upon type of virus, although in almost all cases, administration of human serum containing antibodies (e.g., IgA, IgG) specific to the virus can be effective.

1) Influenza

Influenza infection results in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia.

Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

2) Measles Virus

After an incubation of 9-11 days, hosts infected with the measles virus develope fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the anti-PD-L1 antibodies of the invention so as to facilitate viral clearance would be desirable.

3) Hepatitis B virus

Hepatitis B virus (HB-V) is the most infectious known bloodborne pathogen. It is a major cause of acute and chronic heptatis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection.

Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trials. Additional treatments for HBV include pegylated α-interferon, adenfovir, entecavir and telbivudine. While passive immunity can be conferred through parental administration of anti-HBsAg serum antibodies, vaccination with inactivated or recombinant HBsAg also confers resistance to infection. The anti-PD-L1 antibodies of the invention may be combined with conventional treatments for hepatitis B infections for therapeutic advantage.

4) Hepatitis C Virus

Hepatitis C virus (HC-V) infection may lead to a chronic form of hepatitis, resulting in cirrhosis. While symptoms are similar to infections resulting from Hepatitis B, in distinct contrast to HB-V, infected hosts can be asymptomatic for 10-20 years. Treatment for HC-V infection includes the administration of a combination of α-interferon and ribavirin. A promising potential therapy for HC-V infection is the protease inhibitor telaprevir (VX-960). Additional treatments include: anti-PD-1 antibody (MDX-1106, Medarex), bavituximab (an antibody that binds anionic phospholipid phosphatidylserine in a B2-glycoprotein I dependent manner, Peregrine Pharmaceuticals), anti-HPV viral coat protein E2 antibod(y)(ies) (E.g., ATL 6865-Ab68+Ab65, XTL Pharmaceuticals) and Civacir® (polyclonal anti-HCV human immune globulin). The anti-PD-L1 antibodies of the invention may be combined with one or more of these treatments for hepatitis C infections for therapeutic advantage.

Protease, polymerase and NS5A inhibitors which may be used in combination with the anti-PD-L1 antibodies of the invention to specifically treat Hepatitis C infection include the following identified in Table B

TABLE B

Hepatitis C protease and polymerase inhibitors

| Type of inhibitor | Inhibitor Name | Manufacturer(s) |
| --- | --- | --- |
| Protease | R7227/ITMN 191 | Roche/InterMune |
|  | CTS-1027 | Roche Biosciences |
|  | VX500, VX813, VX985 | Vertex |
|  | Telaprevir (VX950) | Vertex/Tibotec |
|  | TMC435350/TMC 435 | Medivir/Tibotec |
|  | Boceprevir (SCH503034), Narlaprevir (SCH900518/SP900518) | Schering-Plough |
|  | BI201335, BILN 2061 | Boehringer Ingelheim |
|  | MK7009 | Merck |
|  | IDX-136, IDX-316 | Idenix |
|  | BMS-790052, BMS-791325 | Bristol Myers Squibb |
|  | PHX-1766 | Phenomix |
|  | ACH-806 | Achillion/Gilead |
|  | ACH-1625 | Achillion |
|  | ABT-450 | Abbott Labs |
|  | VBY 376 | Virobay |
| Polymerase Inhibitors | R1626 | Roche |
|  | R7128 | Roche/Pharmasset |
|  | NM283 | Idenix |
|  | HCV796 | Wyeth |
|  | BILB 1941, BI-207127 | Boehringer Ingelheim |
|  | GL60667, GS9190 | Gilead |
|  | PF-00868554 | Pfizer |
|  | VCH757, VCH916 | Virochem |
|  | VX222, VX759 | Vertex |
|  | MK-3281 | Merck |
|  | ANA598 | Anadys |
|  | IDX184, IDX375 | Idenix |
|  | PSI-7851 | Pharmasset |
|  | ABT-072, ABT-333 | Abbott Labs |
|  | BMS650032 | Bristol Myers Squibb |
| NS5A Inhibitors | BMS790052, BMX824393 | Bristol Myers Squibb |
|  | AZD 2836, AZD 7295 | Arrow Therapeutics |
|  | GSK 625433 | Glaxo Smith Kline |

5) Human Immunodeficiency Virus (HIV)

HIV attacks CD4+ cells, including T-lymphocytes, monocyte-macrophages, follicular dendritic cells and Langerhan's cells, and CD4+ helper/inducer cells are depleted. As a result, the host acquires a severe defect in cell-mediated immunity. Infection with HIV results in AIDS in at least 50% of individuals, and is transmitted via sexual contact, administration of infected blood or blood products, artificial insemination with infected semen, exposure to blood-containing needles or syringes and transmission from an infected mother to infant during childbirth.

A host infected with HIV may be asymptomatic, or may develop an acute illness that resembling mononucleosis—fever, headache, sore throat, malaise and rash. Symptoms can progress to progressive immune dysfunction, including persistent fever, night sweats, weight loss, unexplained diarrhea, eczema, psoriasis, seborrheic dermatitis, herpes zoster, oral candidiasis and oral hairy leukoplakia. Opportunistic infections by a host of parasites are common in patients whose infections develop into AIDS.

Treatments for HIV include antiviral therapies including nucleoside analogs, zidovudine (AST) either alone or in combination with didanosine or zalcitabine, dideoxyinosine, dideoxycytidine, lamivdudine, stavudine; reverse transcriptive inhibitors such as delavirdine, nevirapine, loviride, and proteinase inhibitors such as saquinavir, ritonavir, indinavir and nelfinavir. The anti-PD-L1 antibodies of the invention may be combined with conventional treatments for HIV infections for therapeutic advantage.

6) Cytomegalovirus

Cytomegalovirus (CMV) infection is often associated with persistent, latent and recurrent infection. CMV infects and remains latent in monocytes and granulocyte-monocyte progenitor cells. The clinical symptoms of CMV include mononucleosis-like symptoms (i.e., fever, swollen glands, malaise), and a tendency to develop allergic skin rashes to antibiotics. The virus is spread by direct contact. The virus is shed in the urine, saliva, semen and to a lesser extent in other body fluids. Transmission can also occur from an infected mother to her fetus or newborn and by blood transfusion and organ transplants. CMV infection results in general impairment of cellular immunity, characterized by impaired blastogenic responses to nonspecific mitogens and specific CMV antigens, diminished cytotoxic ability and elevation of CD8 lymphocyte number of CD4+ lymphocytes.

Treatments of CMV infection include the anti-virals ganciclovir, foscarnet and cidovir, but these drugs are typically only prescribed in immunocompromised patients. The anti-PD-L1 antibodies of the invention may be combined with conventional treatments for cytomegalovirus infections for therapeutic advantage.

7) Epstein-Barr Virus

Epstein-Barr virus (EBV) can establish persistent and latent infections and primarily attacks B cells. Infection with EBV results in the clinical condition of infectious mononucleosis, which includes fever, sore throat, often with exudate, generalized lymphadenopathy and splenomegaly. Hepatitis is also present, which can develop into jaundice.

While typical treatments for EBV infections are palliative of symptoms, EBV is associated with the development of certain cancers such as Burkitt's lymphoma and nasopharyngeal cancer. Thus, clearance of viral infection before these complications result would be of great benefit. The anti-PD-L1 antibodies of the invention may be combined with conventional treatments for Epstein-Barr virus infections for therapeutic advantage.

8) Herpes Virus

Herpes simplex virus (HSV) is transmitted by direct contact with an infected host. A direct infection may be asymptomatic, but typically result in blisters containing infectious particles. The disease manifests as cycles of active periods of disease, in which lesions appear and disappear as the viral latently infect the nerve ganglion for subsequent outbreaks. Lesions may be on the face, genitals, eyes and/or hands. In some case, an infection can also cause encephalitis.

Treatments for herpes infections are directed primarily to resolving the symptomatic outbreaks, and include systemic antiviral medicines such as: acyclovir (e.g., Zovirax®), valaciclovir, famciclovir, penciclovir, and topical medications such as docosanol (Abreva®), tromantadine and zilactin. The clearance of latent infections of herpes would be of great clinical benefit. The anti-PD-L1 antibodies of the invention may be combined with conventional treatments for herpes virus infections for therapeutic advantage.

9) HTLV

Human T-lymphotrophic virus (HTLV-1, HTLV-2) is transmitted via sexual contact, breast feeding or exposure to contaminated blood. The virus activates a subset of $T_H$ cells called Th1 cells, resulting in their overproliferation and overproduction of Th1 related cytokines (e.g., IFN-γ and TNF-α). This in turn results in a suppression of Th2 lymphocytes and reduction of Th2 cytokine production (e.g., IL-4, IL-5, IL-10 and IL-13), causing a reduction in the ability of an infected host to mount an adequate immune response to invading organisms requiring a Th2-dependent response for clearance (e.g., parasitic infections, production of mucosal and humoral antibodies).

HTLV infections cause lead to opportunistic infections resulting in bronchiectasis, dermatitis and superinfections with *Staphylococcus* spp. and *Strongyloides* spp. resulting in death from polymicrobial sepsis. HTLV infection can also lead directly to adult T-cell leukemia/lymphoma and progressive demyelinating upper motor neuron disease known as HAM/TSP. The clearance of HTLV latent infections would be of great clinical benefit. The anti-PD-L1 antibodies of the invention may be combined with conventional treatments for HTLV infections for therapeutic advantage.

10) HPV

Human papilloma virus (HPV) primarily affects keratinocytes and occurs in two forms: cutaneous and genital. Transmission it believed to occurs through direct contact and/or sexual activity. Both cutaneous and genital HPV infection, can result in warts and latent infections and sometimes recurring infections, which are controlled by host immunity which controls the symptoms and blocks the appearance of warts, but leaves the host capable of transmitting the infection to others.

Infection with HPV can also lead to certain cancers, such as cervical, anal, vulvar, penile and oropharynial cancer. There are no known cures for HPV infection, but current treatment is topical application of Imiquimod, which stimulates the immune system to attack the affected area. The clearance of HPV latent infections would be of great clinical benefit. The anti-PD-L1 antibodies of the invention may be combined with conventional treatments for HPV infections for therapeutic advantage.

c. Fungus

Fungal infections, or mycoses, can result as either a primary infection or as opportunistic colonization of hosts with compromised immune systems by endogenous flora. Immunity to mycoses is principally cellular, involving neutrophils, macrophages, lymphocytes and probably natural killer (NK) cells. Mycoses are typically not susceptible to direct killing by antibody and complement. Systemic invasive mycoses resulting from primary infection include blastomycosis, coccidioiodmycosis, histoplamosis, and paracoccidioiodmycosis. For chronic infections results from fungal infections, the anti-PD-L1 antibodies of the invention may be administered prior to simultaneously with or subsequent to any of the conventionally known treatments for these mycoses.

Blastomycosis, caused by *Blastomyces dermatitis* is inhalation-acquired and produces a primary pulmonary infection or hematogenously disseminated disease involving predominantly skin, bones, and the male genitourinary tract. Primary exposure may be asymptomatic, or it may produce an influenza-like syndrome. This disease can manifest in a chronic indolent form. The disease is also associated with compromised immune such as in patients with AIDS. Conventional therapy for *B. dermatitis* infection include itraconazole, ketoconazole or intravenous injection of amphotericin B.

Coccidioiodmycosis, caused by *Coccidioides immitis*, is inhalation-acquired and can cause primary pulmonary infection, progressive pulmonary disease, or hematogenously disseminated disease involving predominantly skin, subcutaneous tissues, bones, joints, and meninges. Primary exposure may be asymptomatic (60%) or associated with an influenza-like syndrome. Pneumonia, pleuritis, and pulmonary cavitation may occur. Metastatic manisfestations include skin lesions, including nodules, ulcers, sinus tracts from deeper loci and verrucouse granulomas, bones, joints, tendon sheaths and meninges, including meningitis. The disease is also associated with compromised immunity such as in patients with AIDS. Treatment for coccidioidiomycosis includes ketoconazole, intraconazole and fluconazole, especially for long-term maintenance therapy of nonmeningial disease. Meningial forms are treated usually with intrathecal administration of Amphotericin B.

Histoplasmosis, caused by *Histoplasma capsulatum*, is an inhalation-acquired disease of the reticuloendothelial system in which tiny yeasts reside in macrophages. It can produce primary pulmonary infection, progressive pulmonary disease or hematogenously disseminated disease involving predominantly the reticuloendothelial system, mucosal surfaces, and adrenal glands. Reactivation of latent infections often occur in patients with compromised immunity, such as in patients with AIDS. Primary exposure may be asymptomatic or associated with a flu-like syndrome, including pneumonia, pleuritis, pulmonary cavitation and mediastinal adenopathy. Metastatic sites include the reticuloendothelial system (hepatosplenomegaly, lymphadenopathy, anemia, leucopenia and thrombocytopenia), mucous membranes (oronasopharnygeal ulcerations), gastrointestinal tract (malabsorption), and adrenal insufficiency. While most primary infections resolve spontaneously, when associated with compromised immunity such as in patients with AIDS, relapse is ongoing and is often associated with hematogenous pneumonia, ARDS, disseminated intravascular coagulation (DIC), hematogenously distributed papulopustules and meningitis. Histoplasmosis is treated with Amphotericin B (especially in immunocompromised patients acutely ill with hematogenous dissemination), intraconzoles and ketoconazole.

Paracoccidioiomycosis, caused by *Paracoccidioides brasiliensis*, is an inhalation-acquired mycosis that can produce primary pulmonary infection or hematogenously disseminated disease involving predominantly the skin, mucouse membranes, reticulendothelial system and adrenals. Infection may be initially asymptomatic but dormant, and then revive. Treatment of this infection uses ketoconazole, intraconzole and sulfonamides.

Systemic invasive mycoses resulting from opportunistic pathogens, which occur in immunocompromised hosts, include candidiasis, cryptococcosis, aspergillossi, mucomycosis and pneumocystosis. By heightening immune response in a compromised immune system, the anti-PD-L1 antibodies of the invention may also have therapeutic value in the treatment of these conditions, especially when combined with conventional therapies.

Treatments for candidiasis (caused by *Candida albicans, C. tropicalis, C. glabrata*), crytococcosis (caused by *Cryptococcus neoformans*), aspergillosis (caused by *Aspergillus flavus, A. fumigatus, A. tereus* and *A. niger*) and mucormycosis (caused by *Rhizopus arrhizus, Rhizomuco, Absidia, Cunninghamella, Mortierella, Saksenaea* spp.) may be treated by one or more of the following imidazole, ketoconazole, intraconazole, fluconazole, amphotericin B with and without flucytosine. Pneumocystitis (caused by penumocystis carnii) recently reclassified from protozoan to fungi is treated with trimethoprim-sulfamethoxole (TMP-SMZ) and intravenous pentamidine isethionate, as well as dapsone, TMP-dapson, trimetrexate, clindamycin-primaquine and atovagnone.

Microsporidiosis caused by Microsporidia parasites, was recently reclassified from protozoan to fungi. They are unicellular organisms which have mitosomes instead of mitochondria. Organisims that can cause disease in humans include: *Enterocytozoon bieneusi, Encephalitozoon hellem, Encephalitozoon intestinalis, Encephalitozoon cuniculi, Pleistophora* spp, *Trachipleistophora hominis, Trachipleistophora anthropophthera, Nosema connori, Nosema ocularum, Brachiola vesicularum, Vittaforma corneae, Microsporidium ceylonensis, Microsporidium africanum, Brachiola algerae.*

Infections are believed to be transmitted to humans from direct contact with animals, contaminated water or another infected host. After infecting host cells, the sporoplasm grows, dividing or forming a multinucleate *plasmodium* which can have complex life cycles including both asexual and sexual reproduction. Autoinfection by successive generations and chronic, debilitating diseases often characterize Microsporidial infections.

The clinical manifestations of the disease can vary depending on the species and the host's immune status, and include conjunctivitis (e.g., *V. corneae*), chronic diarrhea, malabsorption and wasting (e.g., *E. bieneusi, E. intestinalis*).

Treatments for ocular, intestinal and disseminated microsporosis includes administration of albendazole. Topical application of fumagillin may also be used effectively to treat microsporidial keratoconjunctivitis. Other drugs include antihelminthics (e.g., albendazole), antibiotics (e.g., fumagillin), immunomodulators (e.g., thalidomide), antiprotozoals, (e.g., metronidazole).

d. Protozoan

Disease resulting from parasitic disorders such as malaria, schistosomiasis and leishmaniasis are among the most prevalent and important health problems in developing countries. These diseases pose particular challenges because they may evade host immunity through various means, including: 1) living inside host cells (e.g., *Leishmania*), 2) rapidly change surface antigens (e.g., trypansomes) and 3) "disguising" themselves as host cells by displaying host antigens (e.g., schistosomisasis). The use of immunosuppressive drugs in the treatment of cancer and in conjunction with organ transplants, as well the global prevalence of AIDs can reactivate latent or subclinical infections from *Plasmodium* spp., *Toxoplasma* spp., *Leishmania* spp., *Cryptosporidium* spp., *Trypanosoma* spp. and helminths.

For chronic infections resulting from infections with protozoan parasites, the anti-PD-L1 antibodies of the invention may be combined by administration in combination with, prior to or subsequent with standard anti-protozoan therapies.

Malaria, caused by parasites of genus *Plasmodium* (E.g., *P. ovale, P. malariae, P. falciparum, P. vivax*), begins the infectious cycle as a sporozite which develops in the gut of the female anopheline mosquito. Upon transmission into humans, these sporozites invade and multiply within hepatic cells without inducing an inflammatory reaction. The progeny of these organisms, called merozoites, then invade erythrocytic cells and initiate the clinical phase of the disease, typically characterized by fever and chills. In areas of the world where infection is endemic, nearly all residents harbor continuous low level chronic infections of low to moderate pathogenicity, with increasing levels of IgG antibodies providing protection from merozoite entry into erythrocytes.

Currently available anti-malarial drugs for both treatment of clinical disease and prophylaxic include: Artemether-lumefantrine (therapy, E.g., Coartem® and Riamet®), artesunate-amodiaquine (therapy), artesunate-mefloquine (therapy), artesunate-Sulfadoxine/pyrimethamine (therapy), atovaquone-proguanil, (therapy and prophylaxis, E.g., Malarone®), quinine (therapy), chloroquine (therapy and prophylaxis), cotrifazid (therapy and prophylaxis), doxycycline (therapy and prophylaxis), mefloquine, (therapy and prophylaxis, E.g., Lariam®), primaquine (Therapy in *P. vivax* and *P. ovale* only; not for prophylaxis), proguanil (prophylaxis), sulfadoxine-pyrimethamine (therapy and prophylaxis), hydroxychloroquine, (therapy and prophylaxis, E.g., Plaquenil®)

Through reactivating anerigic T-cells, the anti-PD-L1 antibodies of the invention may particularly therapeutic in aiding clearance of malarial parasites.

Toxoplasmosis, caused by parasites of the genus *Toxoplasma*, is often asymptomatic, but a small fraction can develop clinical disease, which can range from benign lymphadenopathy acute to fatal infections of the central nervous system. The sources of infection include cysts in raw or partially cooked pork or mutton and oocytes passed in feces of infected cats. Infection occus in humans usually through the gastrointestinal tract, and the protozoa can penetrate and proliferate (as tachyzoites) in virtually every cell of the body. These tachyzoites can produce cysts filled with minute slow-growing infective bodies (bradyzoites) that remain viable for long periods of time, resulting in a latent chronic infection. Hosts with compromised immune systems, such as those taking immunosuppressive drugs or suffering from HIV are particularly prone to suffering from toxicoplasmosis.

Medications that are used to treat primary toxoplasmosis include the following: pyrimethamine, both with and without an accompanying antibiotics (E.g., sulfadiazine, clindamycin, spiramycin and minocycline). Latent toxoplasmosis may be treated with the antibiotics atovaquone, both with and without clindamycin.

Leishmaniasis, caused by parasites of the genus *Leishmania*, infect macrophages of the skin and viscera, and is transmitted into humans through sandflies. As there is little or no specific serum antibody, cell-mediation immunity through activated T-cells appears to be a critical route by which infection is cleared. Old World Leishmaniasis, also known as tropical sore, is caused by several species of Leishmania: *L. tropica, L. major* and *L. aethiopica*. New World Leishmaniasis is caused by various subspecies of *L. Mexicana* and *L. braziliensis*. These parasites induce a strong cell-mediated immune response, but the outcome of the clinical disease results also in part to the host response. If the host mounts in a suppressed or inadequate cell-mediated response, the result is diffuse chronic cutaneous leishmaniasis, with little hope for spontaneous cure (E.g. *L. aethiopica, L. Mexicana*). If the host mounts an excessive cell-mediated response, the response is a lupoid or recidiva leishmaniasis, with persistent nonulcerated lymphoid nodules appearing at the edge of primary lesions (E.g., *L. tropica*). Recidiva leishmaniasis can appear from 1 to 10 years after the initial lesion. There are two forms of the disease, cutaneous and visceral, with the cutaneous form manifesting in cutaneous lesions with cell mediated immunity is critical to clearance. In the visceral form, cell-mediated immunity is insufficient or non-existent, and the disease manifest clinically as polyclonal B-cell hypergammaglobulinemia, leukopenia, splenomegaly and elevated production of TNF-α.

Miltefosine (E.g., Impavido®) and paramyocin are currently available treatments for both cutaneous and visceral leishmaniasis.

Crytosporidiosis, caused by infections from protozoans of the genus *Crytosporidia* and results from direct human contact with fecal excrement of infected hosts. The infection of intestinal mucosal tissue can result in diarrhea. The disease typically manifests as an acute infection, but it can become chronic, especially in immunocompromised individuals. Treatments are typically palliative, especially hydration, but paromomycin, azithromycin and serum Ig (e.g., Lactobin-R®) have been successful in clearing infection.

Trypanosomiasis, caused by the parasite *Trypanosoma* (E.g., *T. Brucei*, subsp. gambiense, rodesiense infects humans and cattle through bites from the Tsetse-fly. The challenge that this pathogen poses results from successive generations of populations with displaying different surface antigens. Infections are characterized by elevated levels of non-specific and non-protective serum immunoglobulins.

Treatments for Trypanosomiasis include intravenous administration of the following: pentamidine (for T.b. gambiense), intravenous suramin (for T.b. rhodesiense), eflornithine, melarsoprol both with and without nifurtimox.

Helminthic infection, resulting from trematodes (E.g., *Schistomsoma* spp.), cestodes and nemotodes share the common immune responses of eosinophila and reaginic antibody, responses which are T-cell dependent.

Schistosomiasis (aka bilharzia), caused by *Shistosoma mansoni, S. japonicum, S. haematobium* and *S. mekongi* start their life cycle as eggs in water, which then hatch into miracidia, which penetrate snails and create multiple generations of sporocysts. These in turn produce fork-tailed cercariae which can infect the bloodstream of a human host as a shistosomula, which migrate initially to the lungs, and then to the liver. These flukes eventually pair, mate, and lay eggs in the mesenteric venules. While many of these eggs travels to the intestines and are excreted, some are trapped in the submucosa, portal venules of the liver and other organs of the body. The granulomatous inflammation associated with the trapped eggs is the definitive symptom of chronic schistomsomiasis.

Treatments for schistosomiasis include adminisriaton of Praziquantel®, antimony, Oxamniquine (*S. mansoni*) and Mirazid®.

Cestode infections can be classified into two groups, one is the intestinal dwelling adult tapeworms such as *Diphyllobothrium latum* and *Taenia saginata*, which have a restricted, non-humoral immune effect. The second group describes a migratory tissue-encysting larval tapeworms such as *Hymenolepis nana, Echinococcus granulosus* and *Taenia solium*, which induce strong parenteral host responses and protective serum antibodies. The most serious cestode infection in human is Echinococcosis, which when implanted in the liver, lungs, brain, kidneys or other parts of the body can result in the formation of hydatid cysts.

Treatments for Echinococcosis include administration of metronidazole, albendazole and surgical intervention, such as removal, aspiration, marsupialization or omentopexy.

Nematodes are the most common varied and widely distributed helminths that infect humans, caused disorders such as trichinosis, ascariasis, filariosis and strongylodiosis. Trichinosis, caused by *Trichinella spiralis*, can result from ingestion of the larvae of *T. spiralis* in raw meat or partially cooked meat such as pork. In humans, infections elicit strong humoral response with elevated IgM, followed by IgG production, followed by rapid expulsion of antibody-damaged worms by T-lymphocytes.

The only known treatment for killing adult worms in the intestine is thiabendazole, while there is no known treatment to kill the larvae.

*Ascaris*, also known as giant roundworm (*Ascaris lumbricoides*), is a common parasite in humans resulting from ingestion of fecally-contaminated substances. While patients can remain asymptomatic for very long periods of time, as larval stages travel through the body, they may cause visceral damage, peritonitis and inflammation, enlargement of the liver or spleen, toxicity, and pneumonia.

Treatments for *ascariasis* include administration of mebendazole (E.g., Vermox®), piperazine, pyrantel pamoate (E.g., Antiminth®, Pin-Rid®, Pin-X®), albendazole, thiabendazole with or without piperazine, hexylresorcinol, santonin and oil of *Chenopodium*. The anti-PD-L1 antibodies of the invention may be administered in combination with, prior or subsequent to administration of these therapies for the treatment of *ascariasis*.

Filariosis, caused by filarid nematodes, are introduced into humans by insect vectors. *Onchocerca volvulus*, which caused onchoceriasis or river blindness, is transmitted by bites from the blackfly. Infectious larvae lodge themselves subcutaneously and develop into adults, induce a fibrogenic host response, and shed large amount of microfilariae, which disperse subcutaneously and throughout the eyes, further inducing a keratisis or retininitis which then causes the cornea to become opaque. Lymphatic filariasis results from infection by *Brugia* spp. and *Wuchereria* spp. Over time, scarring of the lymph tissue, especially in the groin, may prevent draining, resulting in disfiguring the condition elephantiasis.

The primary treatment for filariosis is the administration of the antibiotic ivermectin, abendazole and diethylcarbamazine citrate (DEC, Hetrazan®) with or without ivermectin or albendazole. Other treatment prospects includes doxycycline, which kills a symbiotic bacteria, wolbochia.

Strongylodiosis, caused by parasites of the genus *Strongyloides* (E.g., *S. stercoralis, S. fulleborni*), is a disease that is passed to humans through fecally contaminated soil. They can exist in both a free living cycle (rabditiform larvae maturing into adult worms) as well as a parasitic cycle (filariform larvae maturing into adult worms) which penetrates the skin, travel to the lungs, then the pharynx and ultimately reside in the intestine. Autoinfection with Strongyloides is also known to occur, which is essentially repeated infection by successive generations of filariform larvae.

Infections may be ayptomatic, or can be characterized by pain and diarrhea in the gastrointestinal tract, Löffler's syndrome in the lungs (i.e., eosinophila) and urticaria. Blood eosinophila may also be present. As persistent infection of *Strongyloides* can mimic peptic ulcer, gallbladder disease and Crohn's disease, misdiagnosis is common. It is a particular problem in immunocompromised hosts.

Known treatments for *Strongyloidiosis* is ivermectin, albenazole or thiabendazole but as this mediation only kills adult worms, repeated administration is necessary.

e. Vaccination

Vaccination or the administration of antigenic material to induce immunity to disease is routinely used to prevent or ameliorate the effects of infection by a pathogen. Enhancing host immunity can be used on undesired antigens found not only on infectious pathogens, but also host tissue that has become diseased (e.g., cancerous). Traditionally, vaccines are derived from weakened or dead whole pathogens, but they can also be peptides representing epitopes on the intact pathogen that are specifically recognized by human class I or class II major histocompatability complex (MHC) molecules. Peptide antigens of particular interest are those which are specifically recognized by T cells.

Recently, it has been shown that combining a therapeutic vaccination with administration of PD-L1 blockade on exhausted CD8+ T cells resulted in enhanced function and viral control in a chronic infection mouse model. Ha et al., *J. Exp. Med.* 205(3): 543-555 (2008). As a result, the anti-PD-L1 antibodies described herein may also be combined with antigen vaccination (e.g., administered prior, simultaneous or after) to treat infection (e.g., acute and chronic) resulting from viral, bacterial, fungal or protozoan invasion as well as tumor immunity.

G. Pharmaceutical Dosages

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the polypeptides or antibodies described herein are used, normal dosage amounts may vary from about 10 ng/kg up to about 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

H. Administration of the Formulation

The formulations of the present invention, including but not limited to reconstituted and liquid formulations, are administered to a mammal in need of treatment with the anti-PD-L1 antibodies, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the mammal by subcutaneous (i.e. beneath the skin) administration. For such purposes, the formulation may be injected using a syringe. However, other devices for administration of the formulation are available such as injection devices (e.g. the INJECT-EASE™ and GENJECT™ devices); injector pens (such as the GENPEN™); auto-injector devices, needleless devices (e.g. MEDIJECTOR™ and BIOJECTOR™); and subcutaneous patch delivery systems.

In a specific embodiment, the present invention is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to anti-PD-L1 antibody, the format of the formulation used, and the discretion of the attending physician. The anti-PD-L1 antibody is suitably administered to the patient at one time or over a series of treatments and may be administered to the patient at any time from diagnosis onwards. The anti-PD-L1 antibody may be administered as the sole treatment or in conjunction with other drugs or therapies useful in treating the condition in question.

For anti-PD-L1 antibodies, an initial candidate dosage can range from about 0.1-20 mg/kg for administration to the patient, which can take the form of one or more separate administrations. However, other dosage regimens may be useful. The progress of such therapy is easily monitored by conventional techniques.

I. Articles of Manufacture

In another embodiment of the invention, an article of manufacture is provided which contains the formulation and preferably provides instructions for its use. The article of manufacture comprises a container. Suitable containers include, for example, bottles, vials (e.g. dual chamber vials), syringes (such as single or dual chamber syringes) and test tubes. The container may be formed from a variety of materials such as glass or plastic. The container holds the formulation. The label, which is on, or associated with the container may indicate directions for reconstitution and/or use. The label may further indicate that the formulation is useful or intended for subcutaneous administration, and/or for the treatment of a T-cell dysfunctional disorder. The container holding the formulation may be a multi-use vial, which allows for repeat administrations (e.g. from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All citations throughout the disclosure are hereby expressly incorporated by reference.

In another embodiment, the invention provides for an article of manufacture comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

EXAMPLE 1

Identification of Anti-PD-L1 Antibodies in Phage Libraries

Library Sorting and Screening to Identify Anti-PD-L1 Antibodies

Human (R&D Systems, cat#156-B7) and murine (R&D Systems, cat#1019-B7) PD-L1-Fc fusions were used as antigens for alternate library sorting. Specifically, phage libraries were sorted first against human antigen, followed by murine, human, and murine antigen in the subsequent three rounds. Nunc 96 well Maxisorp® immunoplates were coated overnight at 4° C. with target antigen (10 µg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., *J. Immunol. Meth.* 284:119-132, 2004) and VH/VL (see Liang et al., *J. Mol. Biol.* 366: 815-829, 2007) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH 7.5). Recovered phages were amplified in *E. coli* XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to both human and murine PD-L1-Fc. The variable regions of these clones were PCR sequenced to identify unique sequence clones.

The parental clones of interest were reformatted into IgGs by cloning $V_L$ and $V_H$ regions of individual clones into the LPG3 and LPG4 vector (Lee et al., supra), respectively, transiently expressing in mammalian CHO cells, and purifying with a protein A column. The 13 Phage antibodies were evaluated for their ability to block the interaction between soluble PD-1-Fc fusion protein and human or mouse PD-L1 expressed in 293 cells (IC 50 values are designated in Table 1—upper half). YW243.55, the antibody with the lowest $IC_{50}$ for blocking human PD-L1 binding to PD-1 was selected for subsequent affinity maturation to improve its affinity for both human and mouse PD-L1. (Table 1). An antibody with comparable cross reactivity against both primate and murine species (as well as retaining affinity to human) would provide for a therapeutic of enhanced value, in that the same antibody that has been well characterized in experimental models can be used in human clinical trials. This avoids the uncertainly resulting from the use of a model-specific surrogate.

Construct Libraries for Affinity Improvement of Clones Derived from the $V_H$ Library Phagemid pW0703 (derived from phagemid pV0350-2b (Lee et al., *J. Mol. Biol.* 340: 1073-1093 (2004)), containing stop codon (TAA) in all CDR-L3 positions and displaying monovalent Fab on the surface of M13 bacteriophage) served as the library template for grafting heavy chain variable domains ($V_H$) of clones of interest from the $V_H$ library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol.* 340, 1073-1093 (2004)). For soft randomization, residues at positions 91-94, and 96 of CDR-L3, 28-31 and 34-35 of CDR-H1, 50, 52, and 53-58 of CDR-H2, 95-99 and 100A of CDR-H3, were targeted; and two different combinations of CDR loops, L3/H1/H2 and L3/H3, were selected for randomization. To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *Journal of Medicinal Chemistry* 37:1233-1251 (1994)).

Phage Sorting to Generate Affinity Improvement

The phage clones previously identified were subjected to plate sorting for the first round, followed by five or six rounds of solution sorting. The libraries were sorted against human and murine PD-L1-Fc separately (R&D Systems, cat. #156-B7, cat #1019-B7, respectively). For the human PD-L1-Fc target, at the first round of plate sorting, three libraries were sorted against target coated plate (NUNC Maxisorp® plate) separately with phage input about 3 O.D./ml in 1% BSA and 0.05% Tween 20 for 2 hours at room temperature. After the first round of plate sorting, solution sorting was performed to increase the stringency of selection. For solution sorting, 1 O.D./ml phage propagated from the first round of plate sorting were incubated with 20 nM biotinylated target protein (the concentration is based on parental clone phage $IC_{50}$ value) in 100 µL buffer containing 1% Superblock (Pierce Biotechnology) and 0.05% Tween-20 for 30 minutes at room temperature. The mixture was further diluted 10× with 1% Superblock, and 100 µL/well was applied to neutravidin-coated wells (5 µg/ml) for 15 minutes at room temperature with gentle shaking such that biotinylated target bound phage. The wells were washed 10× with PBS-0.05% Tween-20. To determine background binding, control wells containing phage with targets that were not biotinylated were captured on neutravidin-coated plates. Bound phage was eluted with 0.1N HCl for 20 minutes, neutralized by 1/10 volume of 1M Tris pH-11, titered, and propagated for the next round. Next, five more rounds of solution sorting were carried out together with two methods of increasing selection stringency. The first of which is for on-rate selection by decreasing biotinylated target protein concentration from 4 nM to 0.5 nM, and the second of which is for off-rate selection by adding excess amounts of non-biotinylated target protein (100~2000 fold more) to compete off weaker binders either at room temperature or 37° C. Also, the phage input was decreased (0.1~0.5 O.D/ml) to lower background phage binding. For murine PD-L1-Fc target, phage sorting method is similar to the one described above for the human PD-L1 Fc antigen, with a few modifications. Specifically, 100 nM biotinylated murine PD-L1-Fc was used for solution panning immediately after first round of plate panning. In the four subsequent rounds of solution panning, biotinylated target was reduced from 10 nM to 1 nM, and 200-500 fold excess of non-biotinylated target was added at room temperature.

The affinity matured clones were then further screened with the High Throughput Affinity Screening ELISA procedure described in the following example.

High Throughput Affinity Screening ELISA (Single Spot Competition)

Colonies were picked from the seventh and sixth round screens for the human and murine PD-L1 target, respectively. Colonies were grown overnight at 37° C. in 150 µL/well of 2YT media with 50 µg/ml carbenicillin and 1E10/ml KO7 in 96-well plate (Falcon). From the same plate, a colony of XL-1 infected parental phage was picked as control. 96-well Nunc Maxisorp® plates were coated with 100 µL/well of human and murine PD-L1-Fc protein (2 µg/ml) separately in PBS at 4° C. overnight or room temperature for 2 hours. The plates were blocked with 65 µL of 1% BSA for 30 min and 40 µL of 1% Tween 20 for another 30 minutes.

The phage supernatant was diluted 1:10 in ELISA (enzyme linked immunosorbent assay) buffer (PBS with 0.5% BSA, 0.05% Tween-20) with or without 10 nM target protein in 100 µl, total volume and incubated at least 1 hour at room temperature in an F plate (NUNC). 75 µL of mixture with or without target protein was transferred side by side to the target protein coated plates. The plate was gently shaken for 15 min to allow the capture of unbound phage to the target protein-coated plate. The plate was washed at least five times with PBS-0.05% Tween-20. The binding was quantified by adding horseradish peroxidase (HRP)-conjugated anti-M13 antibody in ELISA buffer (1:5000) and incubated for 30 minutes at room temperature. The plates were washed with PBS-0.05% Tween 20 at least five times. Next, 100 µL/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 µL 1M Phosphoric Acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation.

$$OD_{450nm}\text{ reduction }(\%)=[OD_{450nm}\text{ of wells with competitor}/(OD_{450nm}\text{ of well with no competitor})]\times 100$$

In comparison to the $OD_{450nm}$ reduction (%) of the well of parental phage (100%), clones that had the $OD_{450nm}$ reduction (%) lower than 50% for both the human and murine target were picked for sequence analysis. Unique clones were selected for phage preparation to determine binding affinity (phage $IC_{50}$) against both human and murine PD-L-Fc by comparison with parental clones.

Materials hPD-1-Fc, hPD-L1-Fc, hB7.1-Fc, mPD-1-Fc, mPD-L1-Fc, and mB7.1 were purchased from R & D Systems. hPD-L1 expressing 293 cells were generated at Genentech using conventional techniques. F(ab')$_2$ goat anti-human IgG Fc was purchased from Jackson ImmunoResearch Laboratories.

Conjugation of Proteins

PD-1-Fc, and B7.1-Fc proteins were biotinylated with EZ-Link sulfo-NHS-LC-LC-biotin (Pierce) for 30 minutes at room temperature as described by the manufacturer. Excess non-reacted biotin was removed with Quick Spin High Capacity Columns, G50-Sephadex (Roche) as described by the manufacturer.

F(ab')$_2$ goat anti-human IgG Fc was Ruthenium labeled with MSD Sulfo-Tag NHS-Ester Meso Scale Discovery) as described by the manufacturer and excess non-reacted Sulfo-Tag was removed with Quick Spin High Capacity Column, G50-Sephadex.

ECL Cell-Binding Assay for Testing Phage Antibodies

Antibody concentrations resulting in 50% inhibition ($IC_{50}$) of the binding of hPD-1-Fc to hPD-L1 expressing 293 cells were measured by electrochemiluminescent (ECL) cell-binding assay. hPD-L1 expression 293 cells were washed with phosphate buffered saline (PBS) and seeded at 25,000 cells per well in 25 µL PBS on 96 well High Bind plate (Meso Scale Discovery). Incubate plate at room temperature to allow the cells to attach to the carbon surface of the plate. Add 25 µL of 30% FBS to each well and incubate the plate for 30 minutes with mild agitation to block non-specific binding sites. Wash plate three times with PBS on an ELISA microplate washer (ELx405 Select, Bio-Tek Instruments) under gentle dispense and aspiration conditions. Remove excess PBS in the wells by blotting plate on paper towels. Add 12.5 µL of 2× concentration of antibodies to each well in 3% FBS in PBS (Assay Buffer) and followed by 12.5 µL of 4 µg/mL (2× concentration) of hPD-1-biotin in Assay Buffer and incubate plate for one hour with mild agitation. Wash plate 3× with PBS on a microplate washer, and blot plate on paper towels. Add 25 µL of 2 µg/mL of Streptavidin-Ruthenium (Meso Scale Discovery) and incubate in assay buffer at room temperature for 30 minutes with gentle agitation. Wash 3× with PBS on microplate washer and blot plate on paper towels. Add 150 µL of 1×MSD Read Buffer without surfactant (Meso Scale Discovery). Read emitted luminescent light at 620 nm on Sector Imager 6000 reader (Meso Scale Discovery). The ECL values were analyzed with the concentrations of the test antibodies used in the assay, using a four-parameter nonlinear least squares fit, to obtain the $IC_{50}$ values of each competitor in the assay.

Results and Discussion

Figure 11B-3:
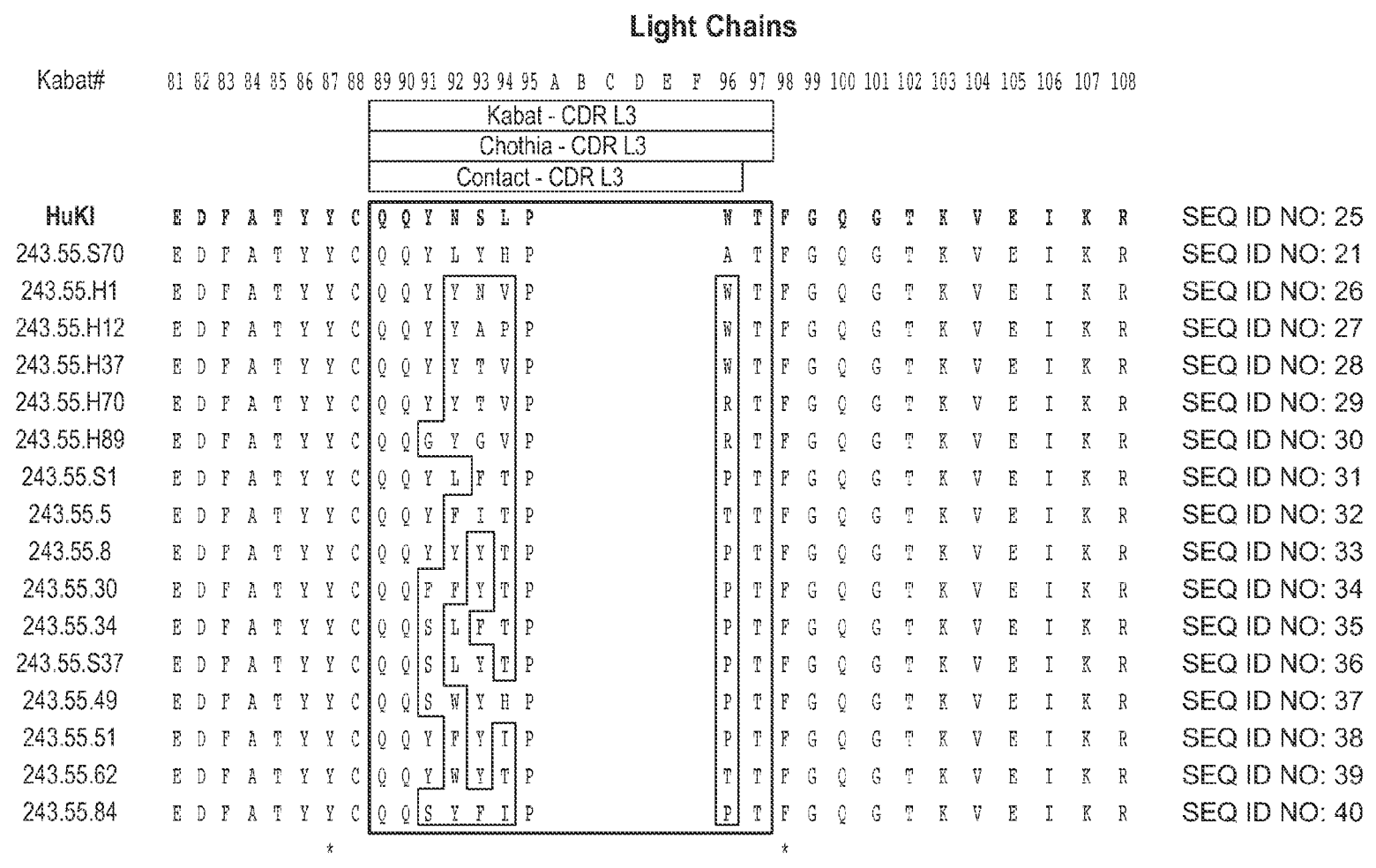

Fifteen unique phage antibodies derived from YW243.55 that bound both human and murine PD-L1 were chosen and reformatted to full length IgG1 antibodies for further evaluation. The light and heavy chain variable region sequences of these antibodies are reported in FIGS. 11A and B.

The fifteen reformatted Abs were tested for their ability to block the binding of PD-1 to 293 cells expressing either human or mouse PD-L1 via an electrochemiluminescent (ECL) cell-binding assay. (Table 1—lower half: In Table 1 "Format 1" describes soluble human PD-1-Fc binding to human PD-L1-tranfected 293 cells; "Format 2" describes murine PD-1-Fc binding to murine PD-L1 transfected 293 cells, and "Format 3" describes human PD-1 binding to murine PD-L1-transfected 293 cells. While all fifteen affinity improved Abs had acquired significant cross-reactivity to mouse PD-L1, YW243.55S70 was selected as the primary candidate to pursue based on its ability to block binding of both human and mouse PD-L1 to PD-1 (Table 1: $IC_{50}$ values of 49 pM and 22 pM, respectively).

TABLE 1

| Clone | Format 1 hPD1-Fc-biotin/ hPDL1-293 $IC_{50}$ in nM | Format 2 mPD1-Fc-biotin/ mPDL1-293 $IC_{50}$ in nM | Format 3 hPD1-Fc-biotin/ mPDL1-293 $IC_{50}$ in nM |
|---|---|---|---|
| YW251.11 | 8.6 | | |
| YW243.1 | 0.234 | | |
| YW243.55 | 0.099 | | >100 |
| YW254.1 | >100 | 0.795 | |
| YW254.2 | >100 | 3.76 | |
| YW254.3 | >100 | >100 | |
| YW254.4 | 1.73 | 15.6 | |
| YW254.9 | >100 | 0.224 | |
| YW254.33 | 2.2 | >100 | |
| YW262.4 | 50 | 1.42 | |
| YW262.5 | 90 | 25 | |
| YW262.16 | 7.5 | 0.626 | |
| YW262.64 | 0.256 | 100 | |
| YW243.55.5 | 0.104 | | 0.141 |
| YW243.55.8 | 0.061 | | 0.063 |
| YW243.55.30 | 0.108 | | 0.100 |

TABLE 1-continued

| Clone | Format 1 hPD1-Fc-biotin/ hPDL1-293 IC$_{50}$ in nM | Format 2 mPD1-Fc-biotin/ mPDL1-293 IC$_{50}$ in nM | Format 3 hPD1-Fc-biotin/ mPDL1-293 IC$_{50}$ in nM |
|---|---|---|---|
| YW243.55.34 | 0.084 | | 0.049 |
| YW243.55.49 | 0.08 | | 0.032 |
| YW243.55.51 | 0.078 | | 0.031 |
| YW243.55.62 | 0.096 | | 0.066 |
| YW243.55.84 | 0.124 | | 0.051 |
| YW243.55.89 | 0.066 | | 0.13 |
| YW243.55.H12 | 0.103 | | 0.156 |
| YW243.55.H37 | 0.109 | | 0.163 |
| YW243.55.H70 | 0.084 | | 0.042 |
| YW243.55.S1 | 0.114 | | 0.074 |
| YW243.55.S37 | 0.100 | | 0.024 |
| YW243.55.S70 | 0.049 | | 0.022 |

EXAMPLE 2

Characterization of Anti-PD-L1 Antibodies (BIAcore)

Binding affinities of anti-PD-L1 phage antibodies YW243.55 and YW243.55S70 against recombinant human and mouse PD-L1 were measured by surface plasmon resonance (SRP) using a BIAcore™-3000 instrument. Recombinant human PD-L1-Fc (R&D Systems, cat #156-B7) and recombinant mouse PD-L1-Fc (R&D Systems, cat#1019-B7) were directly coated on CM5 biosensor chips to achieve approximately 500 response units (RU). For kinetics measurements, two-fold serial dilutions (3.9 nm to 500 nm) were injected in PBT buffer (PBS with 0.05% Tween-20) at 25° C. with a flow rate of 30 μL/min. Association rates ($k_{on}$) and dissociation rate ($k_{off}$) were calculated using a simple one-to-one Languir binding model (BIAcore Evaluation Software version 3.2). The equilibrium dissociation constant (kD) was calculated as the ratio $k_{off}/k_{on}$.

The binding affinities of anti-PD-L1 phage antibody clones YW243.55 and YW243.55.S70 measured are reported below in Table 2.

Human and mouse PD-L1 were stably transfected into 293 cells. Cells were harvested and plated at 150,000 cells per well in a 96-well plate for binding studies.

Rhesus blood was obtained from Southwest Foundation for Biomedical Research (San Antonio, Tex.). Blood was diluted with an equal volume of PBS and overlayed on 96% Ficoll-Paque (GE Healthcare) for separation of mononuclear cells. Mononuclear cells were lysed of red blood cells using erythrocyte lysis buffer (Qiagen) and cultured overnight at $1.5 \times 10^6$ cells/ml with 5 ng/ml PMA plus 1 μM ionomycin in 6-well plates. Culture media was RPMI 1640 with 10% fetal bovine serum, 20 μM HEPES, and 1:100 dilutions of the following supplements from Gibco: Gluta-MAX, sodium pyruvate, penicillin/streptomycin, and non-essential amino acids. Cells were harvested the following day and aliquoted to a 96-well plate for binding studies (approximately 120,000 cells per well).

The PD-L1 antibody YW243.55.S70 or Herceptin® antibody control were titrated starting at 10 μg/ml, in three-fold serial dilutions and bound to cells in 50 μl volumes for 25 minutes on ice. Cells were washed and then bound with anti-human IgG PE (Caltag) at 20 μg/ml for 25 minutes on ice. Rhesus cells were also co-stained with CD3 FITC and CD4 APC (BD Biosciences) to distinguish CD4+ T cells.

All samples were run on a Beckman Dickinson FACSCalibur and Mean Fluorescence Intensity of PD-L1 binding data as a function of anti-PD-L1 antibody concentration was analyzed using Tree Star, Inc. FlowJo® software; EC$_{50}$ values (Ab concentration associated with half-maximal binding) were calculated using Kaleidagraph. In addition, equilibrium binding studies were performed to define accurate affinities (Kds) for YW24355S70 binding to human and mouse PD-L1 expressed on 293 cells (Example 3B). These values are summarized below in Table 3:

TABLE 2

BIAcore binding affinities

| Clone | Immobilized rhPD-L1 Fc | | | Immobilized rmPD-L1 Fc | | |
|---|---|---|---|---|---|---|
| | $k_{on}$/(1/Ms) | $k_{off}$/(1/s) | kD (M) | $k_{on}$/(1/Ms) | $k_{off}$/(1/s) | kD (M) |
| YW243.55 (Fab) | $5.80 \times 10^5$ | $7.30 \times 10^{-3}$ | $1.26 \times 10^{-8}$ | — | — | $>1 \times 10^{-6}$ |
| YW243.55 (IgG) | $2.70 \times 10^5$ | $2.60 \times 10^{-4}$ | $9.63 \times 10^{-10}$ | $5.80 \times 10^4$ | $9.20 \times 10^{-3}$ | $1.59 \times 10^{-7}$ |
| YW243.55.S70 (Fab) | $5.30 \times 10^5$ | $1.00 \times 10^{-4}$ | $1.89 \times 10^{-10}$ | $4.80 \times 10^5$ | $1.40 \times 10^{-3}$ | $2.92 \times 10^{-9}$ |
| YW243.55.S70 (IgG) | $3.90 \times 10^5$ | $6.30 \times 10^{-5}$ | $1.62 \times 10^{-10}$ | $2.80 \times 10^5$ | $1.80 \times 10^{-4}$ | $6.43 \times 10^{-10}$ |

EXAMPLE 3A

Specificity of Anti-PD-L1 Abs for Human, Rhesus and Mouse PD-L1—FACS and Radioligand Cell Binding Assay This example shows the specificity for the anti-PD-L1 antibody of the invention for human, rhesus and mouse PD-L1. In addition, it shows the affinity of the Ab for mouse and human PD-L1 expressed at the cell membrane on 293-transfected cells.

TABLE 3

EC$_{50}$ Summary

| Species | EC$_{50}$ (nm) FACS | Kd (nM) Equilibrium radioligand binding |
|---|---|---|
| Human | 0.4 | 0.4 |
| Rhesus | 0.3 | |
| Mouse | 0.3 | 0.13 |
| Rat | 0.8 | |

EXAMPLE 3B

Affinity Measurement of Anti-PD-L1 Abs to Human and Mouse PD-L1

Equilibrium Binding Radioligand Cell Binding Assay 293 cells transfected with human or mouse PD-L1 were cultured in growth media, which consisted of RPMI 1640 media supplemented with 10% fetal bovine serum (FBS), 2 mM L-glutamine, 1× penicillin-streptomycin, at 37 degrees C. in 5% $CO_2$. Cells were washed with binding buffer (50:50 DMEM/F12 with 2% FBS and 50 mM Hepes, pH 7.2) and were placed into 96-well plates at approximately 230,000 cells in 0.2 mL of binding buffer. The anti-PD-L1 antibody, YW243.55.S70.hIgG, was iodinated using the Iodogen method. The radiolabeled anti-PD-L1 antibodies were purified from free $^{125}$I-NA by gel filtration using a NAP-5 column; the purified Ab had a specific activity of 17.41 µCi/µg. Competition reaction mixtures of 50 µL volume containing a fixed concentration of iodinated antibody and decreasing concentrations of serially diluted unlabeled antibody were placed into 96-well plates. 293 stable transfectant cell lines expressing human PD-L1 and murine PD-L1 were cultured in growth media, which consisted of 50:50 DMEM/F12 media supplemented with 10% fetal bovine serum (FBS), 2 mM L-glutamine, 1× penicillin-streptomycin, at 37° C. in 5% $CO_2$. Cells were washed with binding buffer (50:50 DMEM/F12 with 2% FBS, 50 mM HEPES, pH 7.2, and 2 mM sodium azide) and were added at an approximate density of 200,000 cells in 0.2 mL of binding buffer to the 50 µL competition reaction mixtures. The final concentration of the iodinated antibody in each competition reaction with cells was ~150 pM (~120,000 cpms per 0.25 mL) and the final concentration of the unlabeled antibody in the competition reaction with cells varied, starting at 500 nM and then decreasing by 2 fold for 10 concentrations. Competition reactions with cells were incubated for 2 hours at room temperature. Competition reaction with cells for each concentration of unlabeled antibody was assayed in triplicate. After the 2 hour incubation, the competition reactions were transferred to a Millipore Multiscreen filter plate and washed 4× with binding buffer to separate the free from bound iodinated antibody. The filters were counted on a Wallac Wizard 1470 gamma counter (PerkinElmer Life and Analytical Sciences Inc. Wellesley, Mass.). The binding data was evaluated using NewLigand software (Genentech), which uses the fitting algorithm of Munson and Robard to determine the binding affinity of the antibody. Musson et al., *Anal. Biochem.* 107: 220-39 (1980).

The Kd values as determined by Scatchard analysis corroborates the EC50 values of anti-PD-L1 antibody binding to human and mouse PD-L1 as shown in Table 3.

EXAMPLE 4

Selectivity and Affinity of Anti-PD-L1 Abs ($IC_{50}$)

This example shows the binding selectivity and affinity (as $IC_{50}$) assay used to evaluate the full-length anti-PD-L1 antibodies of the present invention for their ability to block binding of PD-L1 to both PD-1 and B7.1.

Methods hB7.1-Fc-Biotin and hPD-1-Fc-Biotin Binding to hPD-L1-Fc ELISA (Format 4):

Nunc Maxisorp 384 well plate was coated with 25 µL of 250 ng/mL hPD-L1-Fc in PBS overnight. Wash wells three times with 0.05% Tween in PBS (Wash Buffer) on a microplate washer and block wells with 0.5% BSA in PBS. Add 12.5 µL of 2× concentration of antibodies to each well in 0.05% Tween, 0.5% BSA in PBS (Assay Diluent) and followed by 12.5 µL of 250 ng/mL (2× concentration) of hB7.1-Fc-biotin in Assay Diluent and incubate plate for one and half hour with agitation. Wash wells six times with Wash Buffer and add 25 µL of Streptavidin-HRP (1:40,000 in Assay Diluent, GE Healthcare). Incubate plate for 30 minutes with agitation and wash wells six times with Wash Buffer. Add 25 µL of TMB substrate (Kirkegaard and Perry Laboratories) for one hour and stop reaction with 25 µL of 1 M Phosphoric Acid. Read absorbance at 450 nm and analyze $IC_{50}$ values as described under ECL cell-binding assay in Example 1.

Formats 5, 6, 7:

For hPD-1-Fc-biotin binding to hPD-L1-Fc (Format 5), the format is similar to the above assay except hPD-1-Fc-biotin was used instead of hB7.1-Fc-biotin for binding. The TMB substrate reaction time was 17 minutes.

For mB7.1-Fc-biotin binding to mPD-L1-Fc (Format 6), the format is similar to Format 5, except that mPD-L1-Fc was used to coat plate instead of hPD-L1-Fc and mB7.1-Fc-biotin was used for binding instead of hB7.1-Fc-biotin. The TMB substrate reaction time was 7 minutes.

For mPD-1-Fc-biotin binding to mPD-L1-Fc (Format 7), the format is similar to the mouse ELISA mentioned above except mPD-1-Fc-biotin was used for binding instead of mB7.1-Fc-biotin. The TMB substrate reaction time was 5 minutes.

Results

Assessment of the $IC_{50}$ of the affinity-matured phage anti-PD-L1 Antibody YW243.55.S70 to block interactions between the designated binding pairs is reported in Table 4. YW243.55S70 was able to block binding of human PD-L1 to hB7.1 Fc with a half-maximal inhibitory concentration of 38 pM, a concentration relatively comparable to its $IC_{50}$ value for blocking the PD-L1/PD-1 interaction (42 µM). Biacore studies measuring the capacity of YW243.55S70 to block both interactions of PD-L1 with PD-1 and B7.1 were consistent with these ELISA results (data not shown).

TABLE 4

| Antibody | Format 4 hB7.1-biotin/ hPD-L1 $IC_{50}$ in pM | Format 5 hPD-1-biotin/ hPD-L1 $IC_{50}$ in pM | Format 6 mB7.1-biotin/ mPD-L1 $IC_{50}$ in pM | Format 7 mPD-1-biotin/ mPD-L1 $IC_{50}$ in pM |
|---|---|---|---|---|
| YW243.55.S70 | 38 | 42 | 29 | 48 |

EXAMPLE 5

Enhancement of CD4+ and CD8+ T cell activity in vitro by anti-PD-L1 antibody YW243.55.S70 PMEL/B16 In Vitro Assay This example shows the effect of the anti-PD-L1 antibodies of the invention upon activation of PMEL T cell receptor transgenic CD8+ T cells, as measured by enhancement of γ-IFN production in response to melanocyte peptide, gp100. In this procedure, CD8+ T cells are obtained from PMEL TCR transgenic mice whose CD8+ T cells express a TCR specific for the gp100 peptide. Following purification of the CD8+ T cells, multiple rounds of stimulation are performed to generate and expand the activated CD8+ T-cells, which will then in turn upregulate PD-1 expression. In parallel, B16 melanoma cells are treated with IFN-γ to upregulate their PD-L1 expression. Then, the cells are co-cultured in the presence of anti-PD-L1 antibody, and the effect on IFN-γ production is evaluated. B16 cells were chosen for the tertiary stimulation because they endogenously express low levels of gp100 peptide (as opposed to exogenous application of the peptide). Moreover, as these cells also do not express PD-L2, B7.1 or B7.2, the effect of additional signaling unrelated to PD-L1 (e.g. signaling through CD28 or CTLA-4 or PD-L2 induced signaling through PD-1) is minimized.

Figure 3:
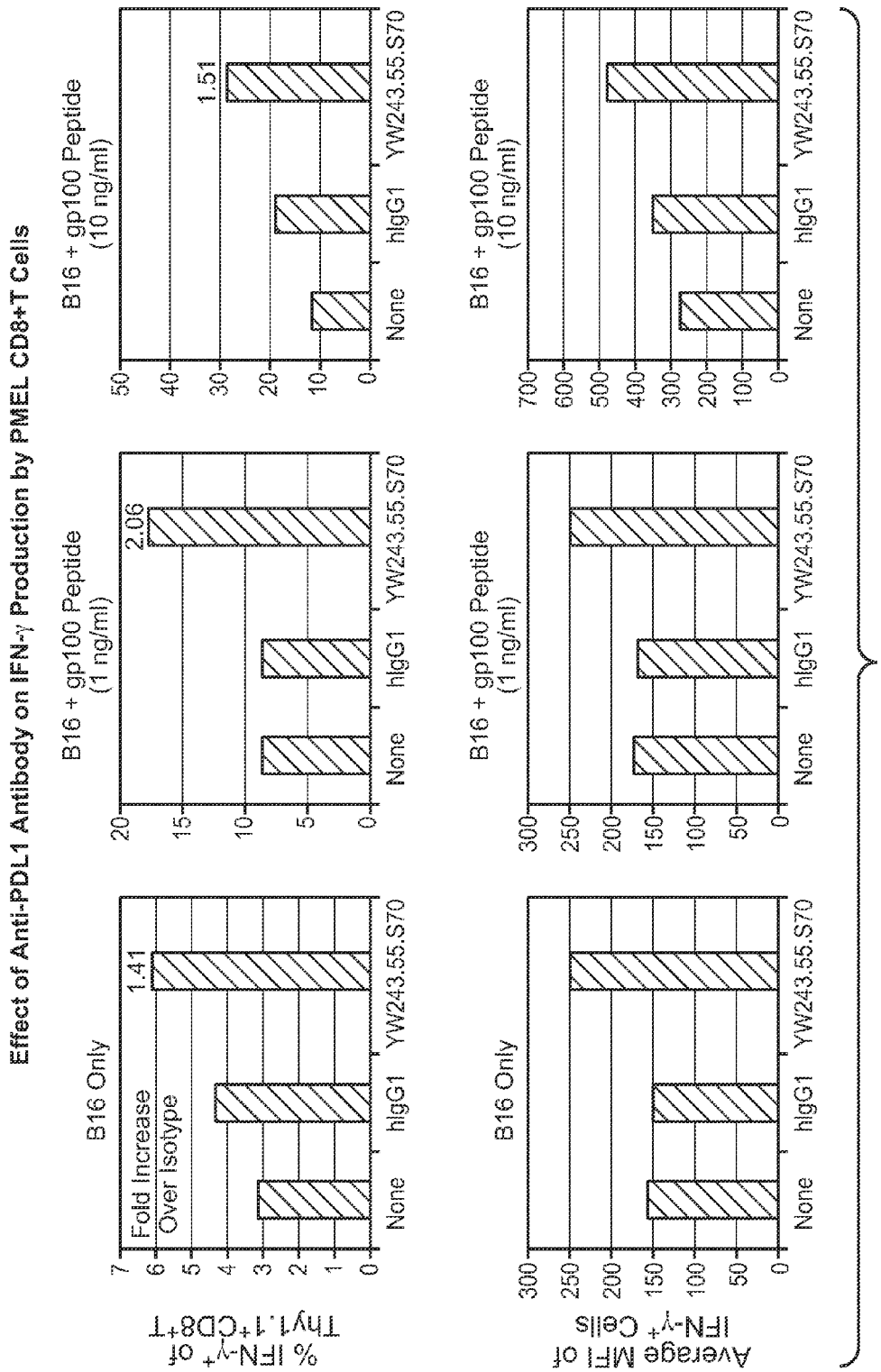
FIG. 3 is a bar graph showing the effect of anti-PD-L1 Ab on antigen-specific T cell function through enhanced IFN-γ production in PMEL CD8+ T cells in response to melanocyte peptide gp100. Both the percentage of IFN-γ producing CD8+ T-cells and their levels of IFN-γ production are increased during stimulation in the presence of the anti-PD-L1 antibody.

PMEL Assay:

As shown in FIG. 3, anti-PD-L1 antibodies enhance both the percentage of IFN-γ-producing PMEL CD8+ T cells and the average levels of IFN-γ produced in response to the designated amounts of gp 100 peptide.

Figure 4:
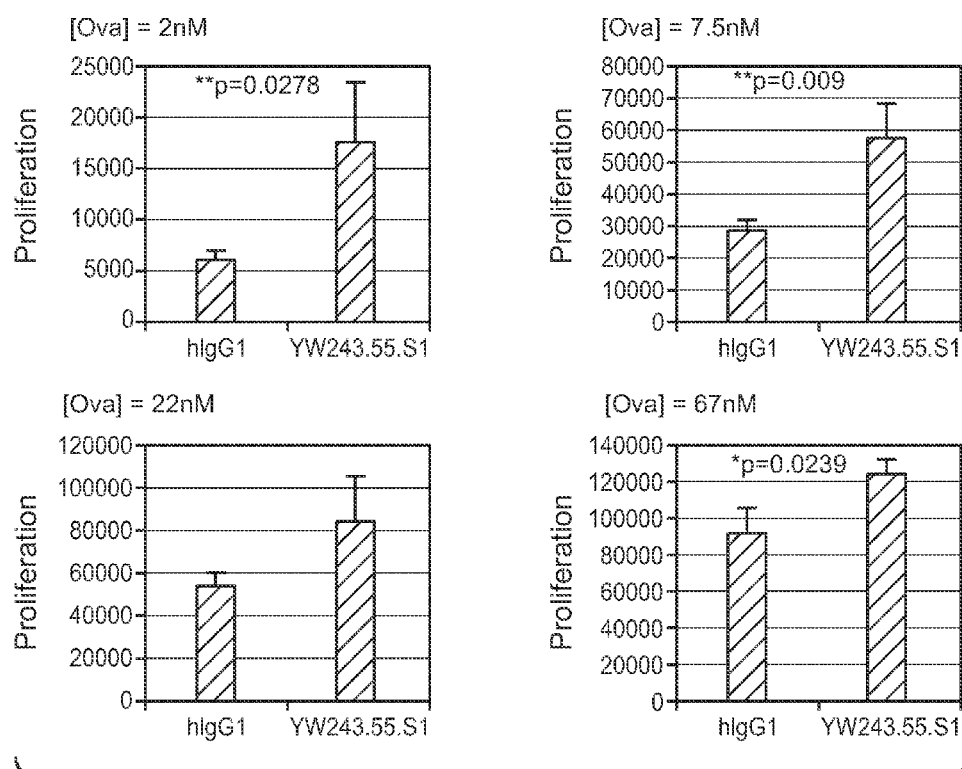
FIG. 4 is a bar graph showing the effect of anti-PD-L1 Ab on antigen-specific T cell function through enhancement in proliferation of Ova-specific CD4+ T cells by the anti-PD-L1 Ab YW243.55.S1 in a secondary stimulation with Ova-pulsed A20 B cells/mPD-L1 APCs.

D.011.10 In Vitro assay:

A similar assay utilizing Ova-specific TCR Tg CD4+ T cells shows enhanced T cell proliferation in the presence of the anti-PD-L1 Ab following prior stimulation with Ova peptide to induce expression of PD-1 (FIG. 4). In the final stimulation, irradiated A20 B cells that express PD-L1 were used to present the designated concentrations of Ova peptide to the DO.11.10 T cells. Notably, the contribution of the PD-1/PD-L1 axis is more pronounced at lower degrees of antigen receptor stimulation, levels that more closely reflect the physiologically relevant magnitude of stimulation.

Materials and Methods

PMEL Assay

Primary Stimulation (day 0-4)

Spleen and mesenteric lymph nodes were harvested from PMEL transgenic T cell receptor mice. Organs were crushed into single cell suspensions and lysed of red blood cells. CD8+ T cells were isolated using the CD8+ T cell isolation kit and AutoMACS cell separator (Miltenyi Biotec) as per manufacturer's instructions.

Spleen was isolated from a non-transgenic sex-matched mouse and crushed into a single cell suspension and red blood cell lysed. Cells were pulsed with 0.1 µg/ml of gp100-peptide for two hours at 37° C. and washed.

Cells were co-cultured in a 96-well flat-bottom plate with 200,000 PMEL CD8+ T cells and 75,000 gp100-pulsed splenocytes for 4 days. Culture media was Iscove's Modified Dulbecco's medium+10% fetal bovine serum+20 µM HEPES, and 1:100 dilutions of the following supplements from Gibco: Gluta-MAX, sodium pyruvate, penicillin/streptomycin, and non-essential amino acids.

Secondary Stimulation (Day 4-7)

PMEL cultures were spun down and the media was aspirated using a multi-channel pipet. Fresh media was added and mixed to wash the cells, followed by another spin. Majority of the media was removed and antibodies (Herceptin®, YW243.55.S70, or none) were added for a final concentration of 10 µg/ml. Conditions were set up in duplicate wells such that the average IFN-γ production could be assessed at the endpoint.

DC-1 cells were pulsed with 0.1 µg/ml gp100 peptide for 2 hours at 37° C. and washed. Gp100-pulsed DC-1 cells were added to washed PMEL cultures at 40,000 cells/well. PMEL and DC-1+ antibody were co-cultured for 3 days.

Third Stimulation (day 7-8)

One day prior to third stimulation on day 6, B16 melanoma cells were incubated with 20 ng/ml of mouse IFN-γ (R&D Systems) overnight to upregulate their PD-L1 expression.

On day 7, PMEL cultures were spun down and the media was aspirated using a multi-channel pipet. Fresh media was added and mixed, followed by another spin. Majority of the media was removed and antibodies were added for a final concentration of 10 µg/ml.

After overnight stimulation with IFN-γ, B16 cells were washed and split into three groups for a two hour incubation with either no gp100, gp100 at 1 ng/ml (gp100 low), and gp100 at 10 ng/ml (gp100 high). Cells were washed and then added to the washed PMEL+Ab cultures at 40,000 cells per well and incubated together overnight.

Day 8 IFN-γ Intracellular Staining

Golgi-Plug (BD Biosciences) was added for the last 5 hours of culture as per manufacturer's instructions. IFN-γ intracellular staining was done using BD Biosciences Cytofix/Cytoperm Fixation/Permeabilization Solution kit as per manufacturer's instructions and all staining antibodies were also from BD Biosciences. Cells were surface stained with CD8a PE and Thy1.1 FITC and intracellular stained with IFN-γ APC at saturating concentrations.

All samples were run on a Beckman Dickinson FACSCalibur and data was analyzed using Tree Star, Inc. FLUWJO™ software.

D011.10 In Vitro Assay

Spleen and mesenteric lymph nodes from D011.10 transgenic mice were harvested, crushed into single cell suspensions, and lysed of red blood cells. Cells were cultured for 72 hours at a density of $1 \times 10^6$ cells per ml in 6 well plates with Ova peptide at 0.3 µM. Culture media was RPMI 1640+10% fetal bovine serum+20 µM HEPES, and 1:100 dilutions of the following supplements from Gibco: Gluta-MAX, sodium pyruvate, penicillin/streptomycin, and non-essential amino acids.

After the primary stimulation, cells were harvested and purified for CD4+ T cells using a mouse CD4 T cell purification kit as per manufacturer's instructions (Miltenyi Biotec). Purified CD4+ T cells were then rested overnight.

The next day, cells were harvested, washed, and co-cultured with irradiated (10,000 rads) A20 cells. Co-culture was set up in 96-well U bottom plates in triplicate wells, with 50,000 CD4+ T cells to 40,000 A20 cells with titrated Ova peptide and antibody at a final concentration of 20 µg/ml. After 48 hours, cultures were pulsed overnight with 1 µCi/well of 3H-thymidine and frozen the next day. Plates were later thawed, harvested on a cell harvester, and read on a beta-counter.

EXAMPLE 6

Enhanced Proliferation of Human CD8+ T Cells in a Mixed Lymphocyte Reaction by Anti-PD-L1

Figure 5:
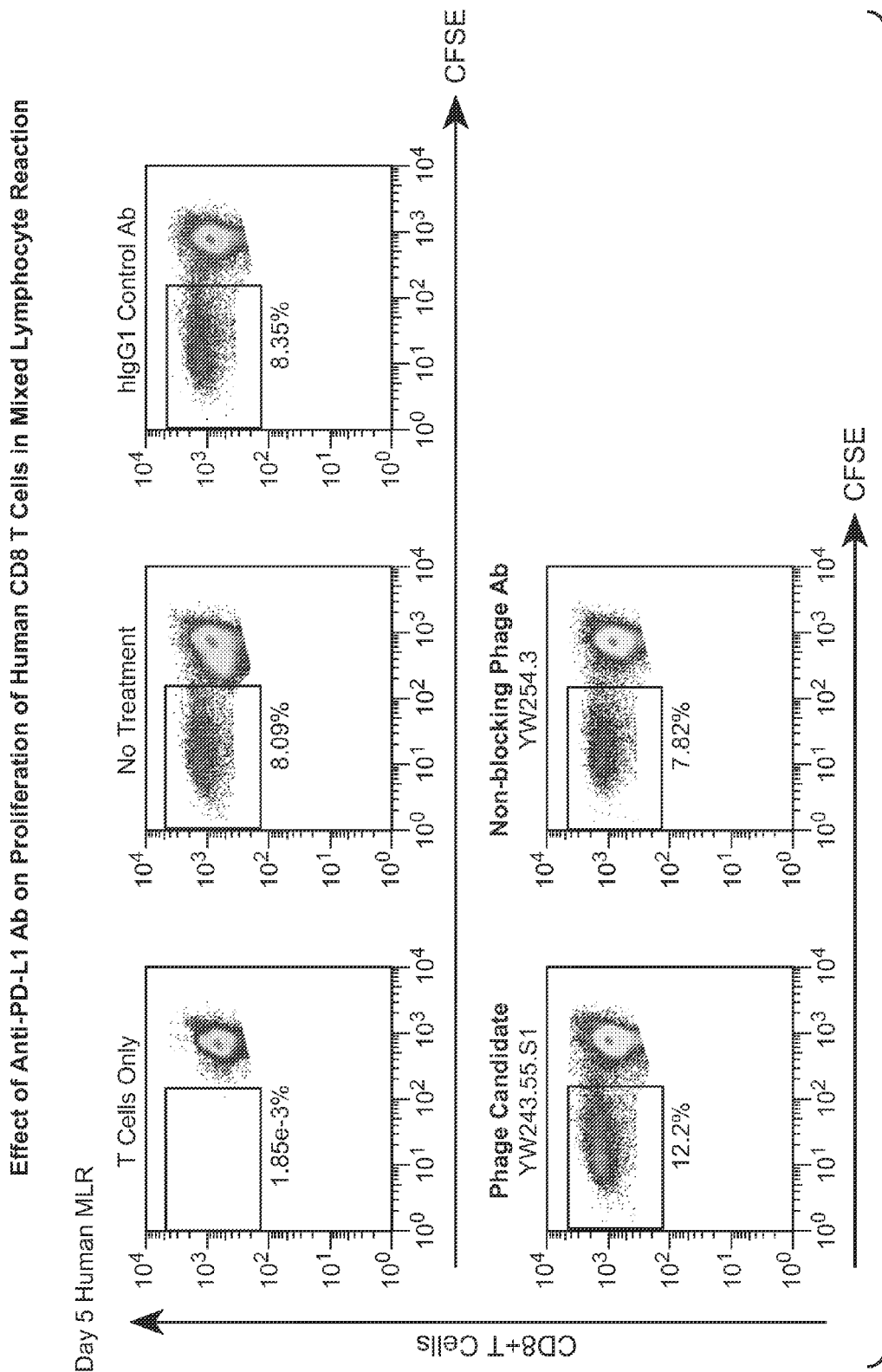
FIG. 5 is a series of FACS plots showing the enhancement in proliferation of human CD8 T cells by anti-PD-L1 antibody YW243.55S1 in a Mixed Lymphocyte Reaction. The percent of proliferating cells as measured by the dilution in intensity of CFSE is also reported.

FIG. 5 demonstrates the ability of anti-PD-L1 (e.g., YW243.55.S1) to enhance proliferation of human CD8 T cells in response to cells from an MHC-mismatched donor.

Responding CD8+ T cells were enriched from whole blood of Donor A by first using CD8+ T cell RosetteSep® (StemCell Technologies) as per manufacturer's instructions. Cells were then diluted by an equal volume of phosphate buffered saline (PBS) and separated by gradient centrifugation by overlaying on Ficoll-Paque Plus (GE Healthcare). After separation, cells were stained with CD8 APC (BD Biosciences) and found to be 78% CD8+ T cells. Cells were fluorescently labeled with 2.5 µM CFSE tracer dye (Molecular Probes).

To serve as allogeneic antigen presenting cells (APCs), mononuclear cells were first isolated from whole blood from Donor B and then depleted of CD3+ T cells. Blood was diluted with an equal volume of PBS and mononuclear cells were isolated after gradient centrifugation over Ficoll. Cells were stained with CD3 FITC (BD Biosciences), washed, and then incubated with anti-FITC microbeads (Miltenyi Biotec). CD3 FITC positive cells were then depleted on the AutoMACS cell separator (Miltenyi Biotec). Cells were then irradiated 2500 rads in a cesium irradiator.

Cells were co-cultured in a 96-well flat-bottom plate with 150,000 CD8+ T cells and 150,000 APCs for 5 days with antibodies at 10 µg/ml. Culture media was RPMI 1640+10% fetal bovine serum+20 µM HEPES, and 1:100 dilutions of the following supplements from Gibco: Gluta-MAX, sodium pyruvate, penicillin/streptomycin, and non-essential amino acids.

On day 5, cells were harvested, washed and stained with CD8-biotin followed by streptavidin-PerCp (BD Biosciences). Samples were run on a Beckman Dickinson FACSCalibur and data was analyzed using Tree Star, Inc. FlowJo software.

An approximately 45% enhancement in proliferation of CD8 T cells responding to cells from an MHC-mismatched donor was observed in the presence of the anti-PD-L1.

EXAMPLE 7

Effects of PD-L1 Blockade on LCMV In Vivo Model

T cells under conditions of chronic stimulation have been shown to upregulate and sustain expression of the inhibitory receptor PD-1. Ligation of PD-1 by either of its two ligands PD-L1 and PD-L2 contributes to the refractory state of the chronically activated T cell, attenuating its response to its cognate antigen. In mice persistently-infected with lymphocytic choriomeningitis virus (LCMV), blockade of PD-1 or its ligand PD-L1 is sufficient to revitalize chronically refractory T cells, enhancing the magnitude and functional quality of the anti-viral T cell response. Similarly, humans chronically infected with HIV or HCV exhibit T cells refractory to simulation whose activity can be enhanced in vitro by blockade of PD-1 or PD-L1. Therefore, activity of PD-L1 blockade in the LCMV model suggests therapeutic potential for enhancing anti-viral and anti-tumor immunity.

Figure 6:
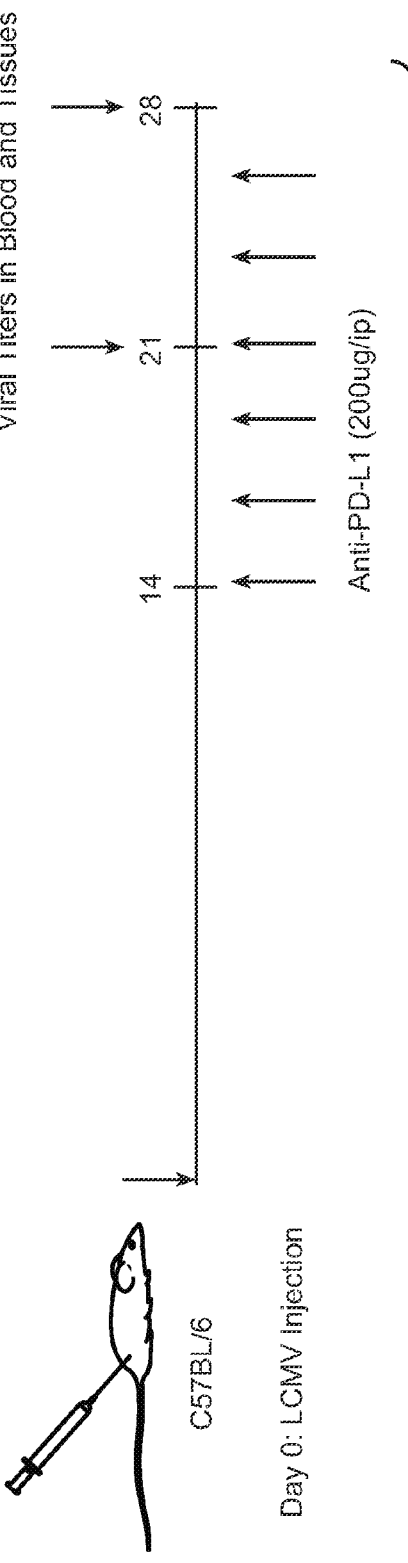
FIG. 6 is a schematic of the experimental design of the treatment of chronic LCMV with chimeric form of anti-PD-L1 Ab YW243.55S70. Arrows designate the timing of the 6 doses of anti-PD-L1 begun 14 days post infection with $2 \times 10^6$ pfu Clone 13 LCMV.

For the LCMV in vivo experiments in the mouse, we have reformatted the humanized anti-PD-L1 antibody (YW243.55S70), by cloning the phage-derived heavy and light chain variable region sequences upstream of mouse IgG2a heavy chain and mouse kappa light chain constant domains. To prevent antibody-mediated cytotoxicity of PD-L1 expressing cells, by inhibiting Fcγ receptor binding, positions 265 (aspartic acid) and 297 (asparagine) were changed to alanine (DANA). Shields, R L et al *J. Biol Chem* 2001 276 (9): 6591-6604. To test the ability of the anti-PD-L1 antibody to enhance anti-viral immunity in a chronic infection, mice were infected at Day 0 with $2 \times 10^6$ plaque forming units (pfu) of Clone 13 LCMV or the Armstrong strain of LCMV as a reference control. The schematic of the experimental design appears in FIG. 6. Infection with Clone 13 results in a chronic infection, characterized by T cells that expand but are unable to effectively clear the virus, while Armstrong LCMV is cleared within 8-10 days of infection. On day 14, mice began treatment with either anti-PD-L1 or control mIgG delivered at 10 mg/kg doses 3×/week. At Days 21 and 28, analysis of CD8 T cell function and viral titers in blood and tissues were performed.

Figure 7A:
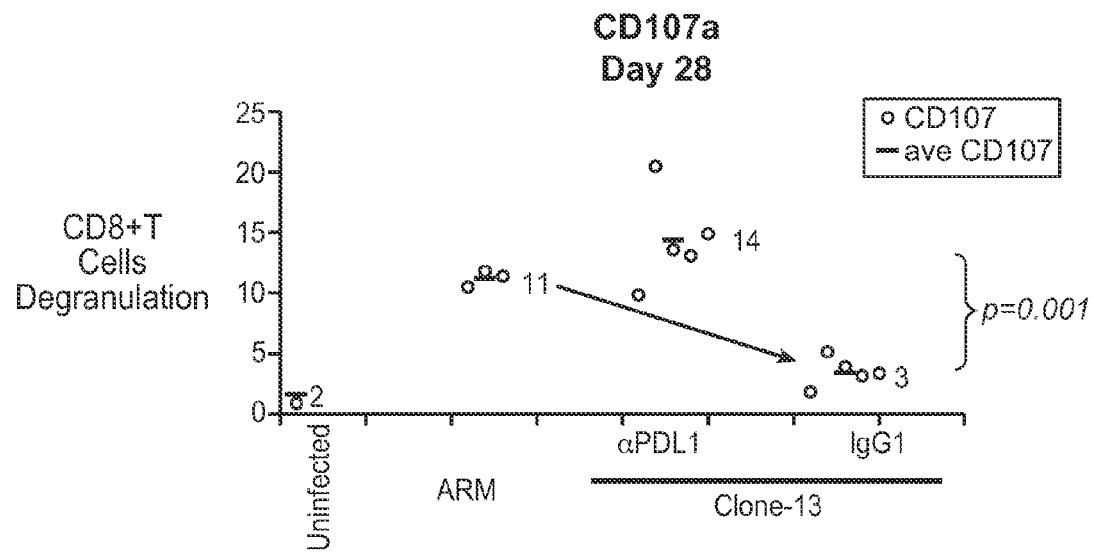
FIGS. 7A and 7B are graphs showing in enhanced CD8 effector function in cells ex vivo following in vivo treatment of chronic LCMV infection by anti-PD-L1 Ab, YW243.55.S70. Blockade of PD-L1 by YW243.55.S70 increased degranulation of $CD8^+$ T cells (as measured by increase in surface CD107A) (FIG. 7A) and increased the % IFN-gamma producing cells in response to LCMV peptide gp33 (FIG. 7B). The frequency of gp33-specific cells is revealed by staining with H2-Db gp33 pentamers.
Figure 7B:
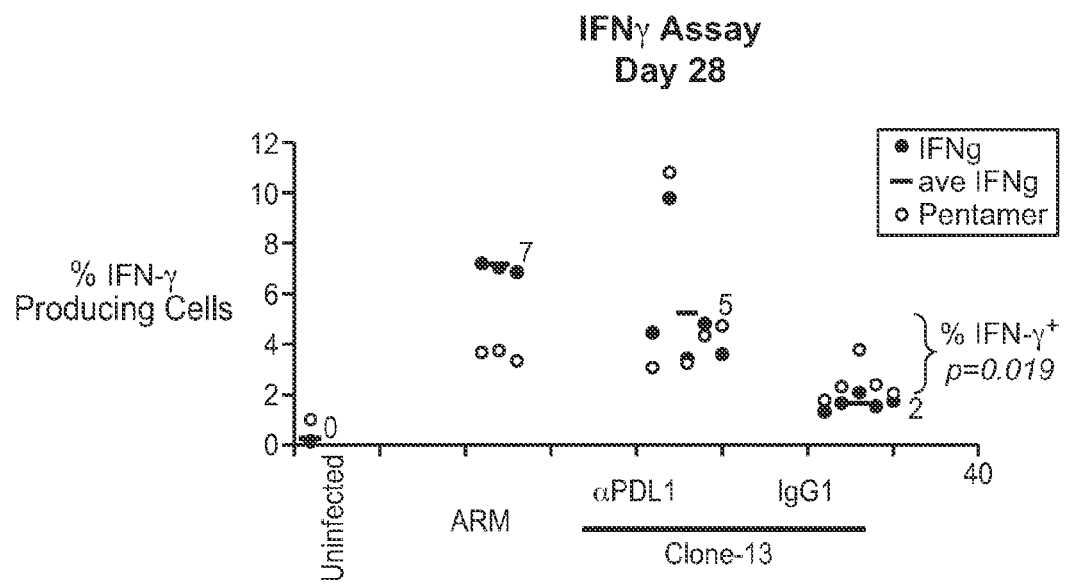

Consistent with published data of Barber et. al, *Nature* 439:682-7 (2006), this example shows the ability of the anti-PD-L1 Ab to enhance the cytotoxic lymphocyte response to LCMV following a 2 week treatment regimen in a chronic LCMV infection. FIG. 7A shows the % of CD8 T cells that express CD107a on their cell surface in response to gp33 LCMV-specific peptide. Plasma membrane expression of CD107a, normally expressed intracellularly, accompanies the degranulation process and therefore serves as a surrogate marker for degranulation. Relative to the response of cells from the acute Armstrong LCMV infection, cells from animals infected with the chronic strain, clone 13, are impaired in degraulation (control Ig group), while PD-L1 blockade was able to restore CD8+ degraulation to levels comparable to those observed in the Armstrong infection. Similarly, 7B demonstrates the increased % of IFN-γ-producing CD8 T cells in response to LCMV gp33 in the anti-PD-L1-treated group relative to control Ig.

Figure 8:
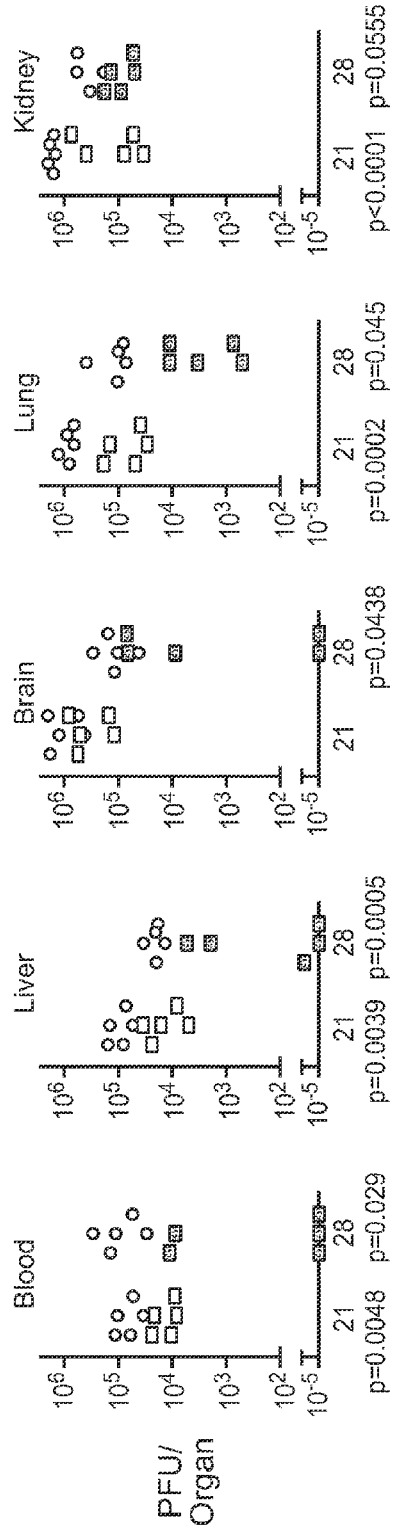
FIGS. 8A and 8B show the reduction in blood and tissue LCMV titers in chronic LCMV infection following in vivo treatment with anti-PD-L1 antibody.
Figure 8:
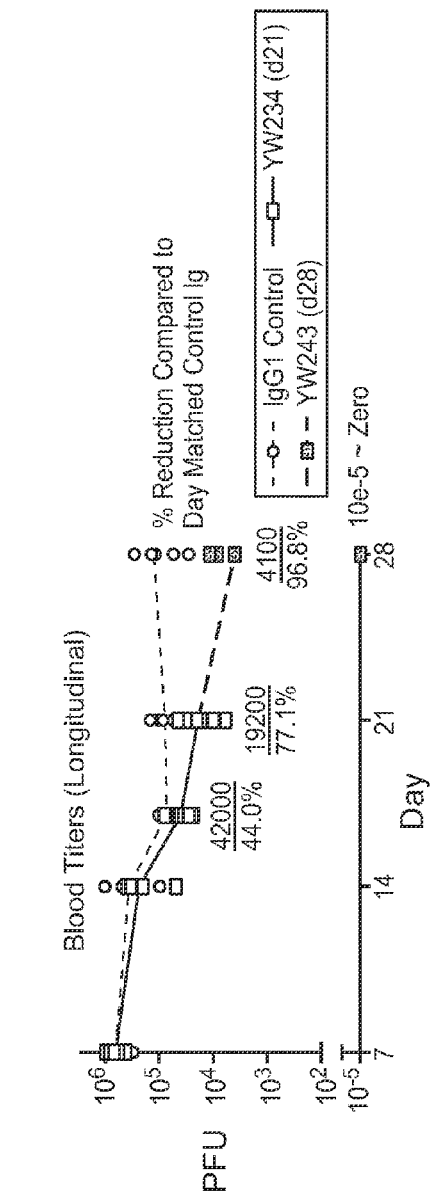

Next, the impact of the anti-PD-L1 Ab on reducing or eradicating LCMV virus in blood and tissues was tested. In FIG. 8A, the graphs show log virus titers in the indicated tissue of control Ig and PD-L1 treated animals at day 21 and 28 after infection with Clone 13 LCMV. Antibody treatment was initiated at Day 14 post-infection. Blockade of PD-L1 resulted in highly significant reduction in viral titers in blood, liver, brain, lung, and kidney. Impressively, in 3 of 5 mice, α-PD-L1 Ab reduced blood LCMV titers to levels below detection ($<1 \times 10^{-5}$). In a subsequent experiment of comparable design, virus eradication in blood and liver was observed in 5/5 mice treated for 2 weeks with anti-PD-L1 at doses of either 10 mg/kg or 2 mg/kg 3×/week (data not shown). The lower graph shows the kinetics of reduction of viral titers in the blood and demonstrates an average reduction of 96.8% in the anti-PD-L1 treated group at Day 28 relative to control. These data support the importance of the PD-1/PD-L1 pathway in inhibiting T cell responses in chronic infections and are consistent with effects of in vitro PD-L1 blockade on T cells obtained from humans with chronic infections such as Hepatitis C and HIV.

Materials and Methods

Determining % IFN-Gamma Production by CD8 T Cells in Response to LCMV gp33 Peptide Spleens were isolated from infected mice and a single cell suspension was generated by crushing the organs in complete media: IMDM (Invitrogen Inc., Carlsbad, Calif.) containing 10% heat inactivated fetal bovine serum, 2 mM L-glutamine, 100 U/ml Penicillin/Streptomycin and 10 mM 2-mercaptoethanol. The red blood cells were lysed using ACK lysis buffer (0.15 M $NH_4Cl$, mM $KHCO_3$, 0.1 mM EDTA). To measure antigen specific CD8 T cell responses, the splenocytes were washed in complete media and restimulated in vitro for 4 hours with the LCMV peptide GP33 (KAVYNFATC, Prolmmune Inc., Bradenton, Fla.). $1 \times 10^6$ splenocytes were cultured in 96 well flat bottom plates with 100 ng/ml of GP33 peptide in the presence of 100 units/ml of human interleukin-2 (Sigma-Aldrich, St. Louis, Mo.) 1 µl/ml of brefeldin A and 1 µl/ml (1:1000 dilution) of monensin (BD pharmingen) and anti-CD107a FITC (clone ID4B, BD Biosciences, San Jose, Calif.). After incubation, cells were washed once in PBS containing 2% fetal bovine serum and cell surface markers were stained using fluorochrome conjugated antibodies: anti-CD8 APC (clone 53.67, BD Biosciences, San Jose, Calif.) anti-CD4 PerCp-Cy5.5 (clone RM4-5, BD Biosciences, San Jose, Calif.) and anti-PD-1 PE (clone J43, BD Biosciences, San Jose, Calif.). Staining for intracellular IFN-γ was done using the Cytofix Cytoperm Plus kit (BD Biosciences, San Jose, Calif.) according to the manufacturer's instructions using anti-IFN-γ PE-Cy7 (clone XMG1.2, eBioscience Inc. San Diego, Calif.). To detect the number of GP33 specific CD8 T cells, fresh splenocytes were stained with GP33 pentamers (H2-Db linked to APC, ProImmune Inc., Bradenton, Fla.) according to the manufacturer's instructions. Data was collected using a BD FACSAria (BD Biosciences, San Jose, Calif.) and analyzed with FlowJo Software (Tree Star Inc. Ashland Oreg.).

Determination of LCMV Viral Titers

MC57 fibrosarcoma cells are infected with 10-fold serial dilutions of LCMV-containing blood or tissue homogenate in complete IMDM. The reaction is then incubated for 2-6 hours in at 37° C. in a tissue culture incubator, then overlayed with DMEM containing 1% methylcellulose. This is followed by incubation for 3-5 days, then the methylcellulose layer is removed by aspiration. The cells are fixed with PBS/4% paraformaldehyde, then permeabilized with 0.5% Triton-x for 20 minutes, washed in PBS, then blocked in 10% FCS for 1 hour with mild rocking. Staining for LCMV is done with VL4 antibody (1 hour), washed 2×, then developed with anti-rat HRP (1:400) in blocking buffer. This followed by washing 3×, then adding o-phenylenediamine substrate (SIGMA P8806-50TAB 3 mg/tablet) to wells to develop.

EXAMPLE 8

PD-L1 Blockade in Cancer

It is now apparent that many tumors exploit expression of PD-1 ligands as a means to attenuate anti-tumor T cells responses. Several human cancers have been characterized to express elevated levels of PD-L1 on both tumors and tumor-infiltrating leukocytes and this elevated PD-L1 expression is often associated with a worse prognosis. Mouse tumor models demonstrate similar increases in PD-L1 expression within tumors and demonstrate a role for the PD-1/PD-L1 pathway in inhibiting tumor immunity.

Figure 9A:
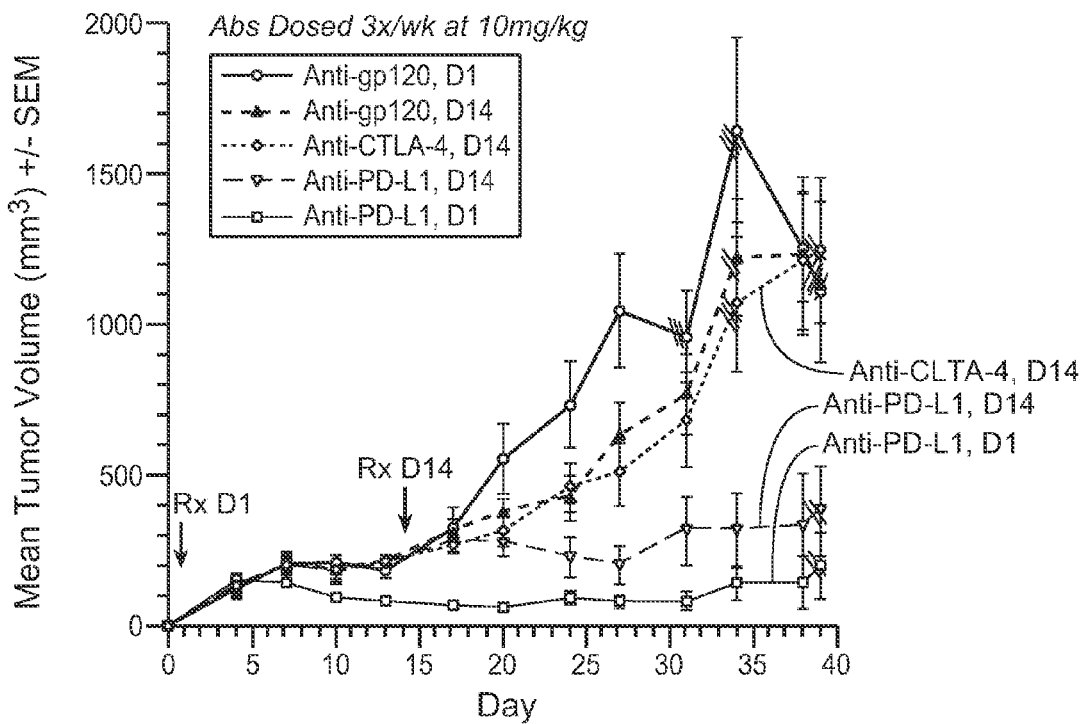
FIG. 9A shows a significant reduction in MC38Ova colon carcinoma tumor growth as a result of application of anti-PD-L1 antibody following therapeutic treatment of established tumors (treatment begun at Day 14, when tumor is 250 mm³).
Figure 9B:
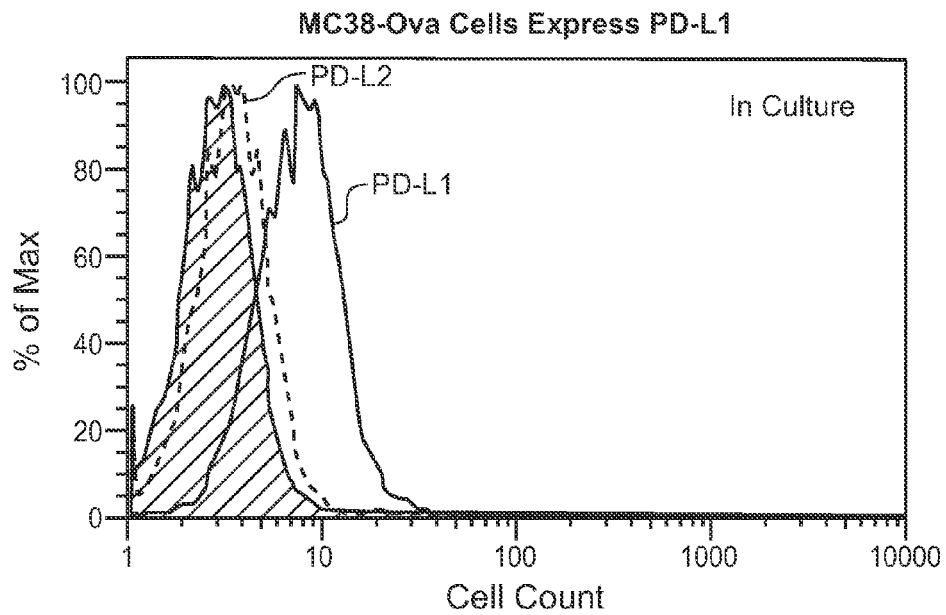
FIG. 9B is a histogram showing surface levels of PD-L1 expression on MC38.Ova cells in tissue culture as measured by flow cytometry. PD-L2 is not expressed by MC38.Ova cells.
Figure 10:
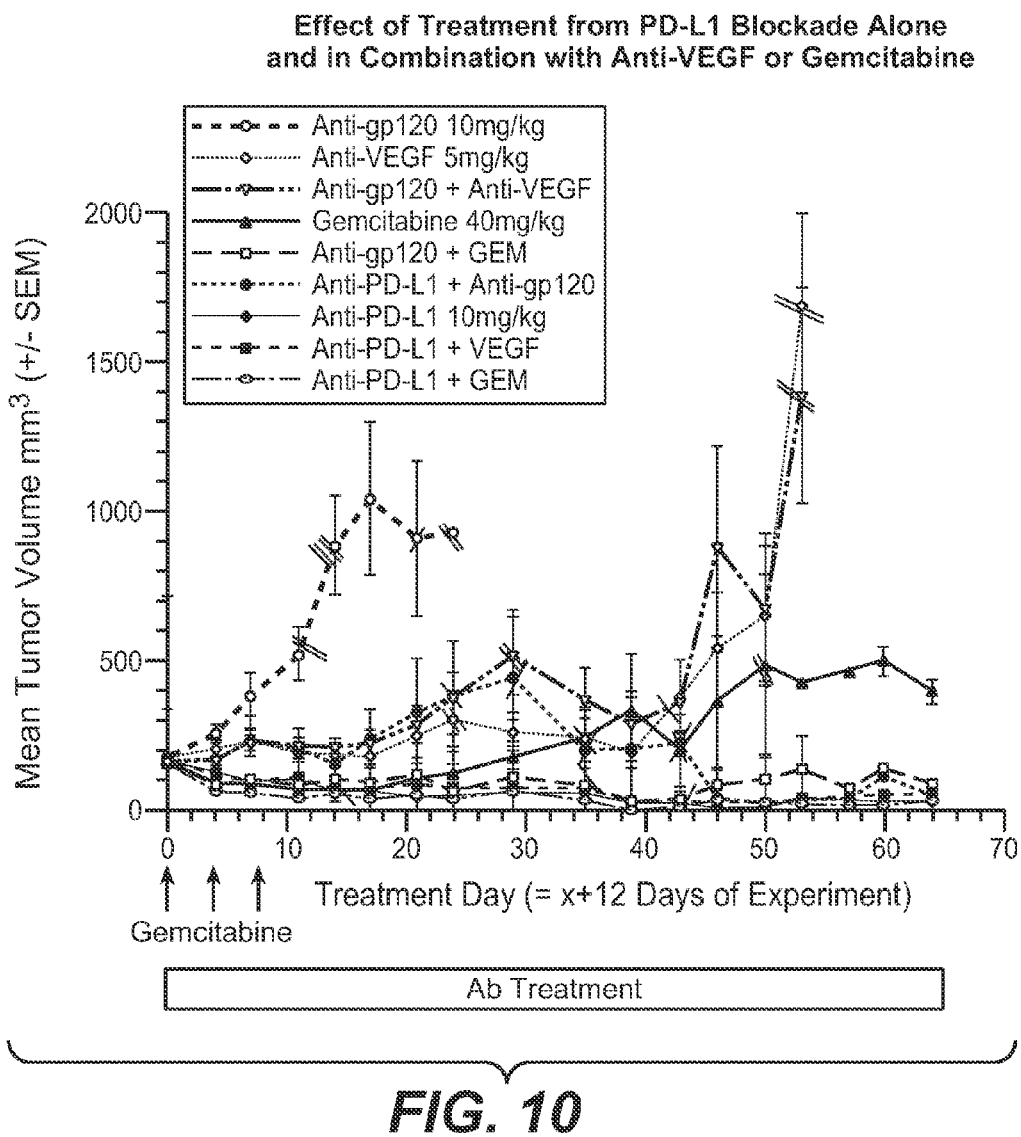
FIG. 10 is a graph showing the effect of PD-L1 blockade treatment alone and in combination with either anti-VEGF or Gemcitabine on the growth of MC38.Ova tumors in C57BL/6 mice.

Here we present an experiment demonstrating the impact of blocking PD-L1 on orthotopic tumor growth of MC38.Ova murine colorectal carcinoma cells in syngeneic C57B6 mice (FIG. 9A). These cells express ovalbumin via retroviral transduction and express PD-L1, but not PD-L2 on their cell surface as assessed by Flow Cytometry (histogram—FIG. 10A). Mice were inoculated subcutaneously with 0.5 million MC38.Ova cells on Day 0. On Day 1 or on Day 14 mice (when tumors had reached an average size of 250 mm$^3$) 10 mice/group were treated with 10 mg/kg anti-PD-L1 (YW243.55S70-mouse IgG2a-DANA), control Ig, or blocking anti-CTLA4 Ab, (UC10-4F10-11) 3×/week for the duration of the study. Blockade of PD-L1 either early or in late intervention is highly effective as a single agent therapy at preventing tumor growth. In contrast, blockade of CTLA4, another inhibitory molecule expressed on T cells showed no evidence of inhibiting tumor growth. These results demonstrate the unique role of the PD-1/PD-L1 axis over CTLA4/B7 in suppression of the anti-tumor immune response and support the potential for the treatment of human cancers with antibodies that block the PD-L1 interaction with PD-1 and B7.1.

MC38.Ova syngeneic tumor model: methods. On Day 0, 70 animals were inoculated subcutaneously with 0.5 million MC38.Ova cell in 100 microliters of HBSS+matrigel. Beginning on D1, 20 mice were recruited into one of 2 treatment groups (see below: group 1 or group 2). The remaining 40 mice were allowed to grow tumors until Day 14. Of these 40, 30 mice with similar-sized tumors were recruited into one of 3 treatment groups (Groups 3-5). The tumors were measured and the mice weighed 2×/week. Mice not recruited into below treatment groups, due to dissimilar tumor volume were euthanized:

Group 1: anti-gp120 antibody, 10 mg/kg IP, 100 μL, D1, 3×/week
Group 2: anti-PD-L1 antibody, 10 mg/kg IP, 100 μL, D1, 3×/week
Group 3: anti-gp120 antibody, 10 mg/kg IP, 100 μL, D14, 3×/week
Group 4: anti-PD-L1 antibody, 10 mg/kg IP, 100 μL, D14, 3×/week
Group 5: anti-CTLA-4 antibody, 10 mg/kg IP, 100 μL, D14, 3×/week
***Groups 1 and 2 began dosing on D1; Groups 3, 4, and 5 on D14.

EXAMPLE 9

Combinations of anti-PD-L1 with other agents to provide for anti-tumor effect or Immune-Enhancing Therapy—MC38.Ova model On Day 0, 150 animals are inoculated subcutaneously with 0.5 million MC38.Ova cell in 100 microliters of HBSS+matrigel. Mice are allowed to grow tumors. Mice are weighed and measured 2×/week until Day 11 (when the tumor volume is between 100-200 mm$^3$). On Day 11, following tumor measurement, mice are recruited into 1 of the 12 treatment groups below. Mice not recruited into below treatment groups, due to dissimilar tumor volume are euthanized. Gemcitabine (Group 4) treatment starts on day 12, while treatment for the remaining antibody groups starts on day 14. All volumes are 100 μl in inert vehicle, with additional details as reported below:

Group 1: anti-gp120 antibody, 10 mg/kg IP, 100 μL, 3×/week×5, n=10
Group 2: anti-PD-L1 antibody, 10 mg/kg IP, 100 μL, 3×/week×5, n=10
Group 3: anti-VEGF antibody, 5 mg/kg IP, 100 μL, 2×/week×5, n=10
Group 4: Gemcitabine, 40 mg/kg W, 100 μl, Day 12, 16, 20, n=10
Group 5: anti-PD-L1 antibody+anti-gp120 antibody, n=10
Group 6: anti-PD-L1 antibody+anti-VEGF antibody, n=10
Group 7: anti-PD-L1 antibody+Gemcitabine, n=10
Group 8: anti-gp120 antibody+Gemcitabine, n=10
Group 9: anti-gp120 antibody+anti-VEGF, n=10
Day 12: Mice from group 1 are bled (100 microliters) retro-orbitally under anaesthesia for CBC analysis.
Day 14 and Day 22: Mice from group 4 are bled (100 microliters) retro-orbitally under anaesthesia for CBC analysis.
Day 19: All mice, except group 4, are bled (100 microliters) retro-orbitally under anaesthesia for CBC analysis.
Day 26: All mice, except group 4, are bled (100 microliters) retro-orbitally under anaesthesia for PK analysis.

Tumors are measured and mice weighed 2x/week. Animals exhibiting weight loss of >15% will be weighed daily and euthanized if they lose >20% body weight. Mice will be euthanized when tumor volumes exceed 3,000 mm³, or after 3 months if tumors do not form.

This study shows (FIG. 10) that PD-L1 blockade was more effective than α-VEGF and an inductive regimen of gemcitabine alone.

EXAMPLE 10

Expression of Anti-PD-L1 Antibody in Mammalian Cells

This example illustrates preparation of potentially glycosylated forms of anti-PD-L1 antibody by recombinant expression in mammalian cells.

The vector, pRK5 (see EP 307,247, published Mar. 15, 1989), is employed as the expression vector. Optionally, DNA encoding the light and/or heavy chain of the antibody is ligated into pRK5 with selected restriction enzymes to allow insertion such DNA using ligation methods such as described in Sambrook et al., supra.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg if DNA encoding the pRK5-antibody is mixed with about 1 µg DNA encoding the VA RNA gene [Thimmappaya et al., Cell, 31:543 (1982)] and dissolved in 500 µL of 1 mM Tris-HCl, 0.1 mM EDTA, 0.227 M $CaCl_2$. To this mixture is added, dropwise, 500 µL of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the antibody. The cultures containing transfected cells may undergo further incubation (in serum free medium) and the medium is tested in selected bioassays.

In an alternative technique, the antibody may be introduced into 293 cells transiently using the dextran sulfate method described by Somparyrac et al., Proc. Natl. Acad. Sci., 12:7575 (1981). 293 cells are grown to maximal density in a spinner flask and 700 µg DNA encoding the pRK5-antibody is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing the expressed antibody can then be concentrated and purified by any selected method, such as dialysis and/or column chromatography.

In another embodiment, the antibody can be expressed in CHO cells. The DNA encoding the antibody ligated into pRK5 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the antibody, the culture medium may be replaced with serum free medium. Preferably, the cultures are incubated for about 6 days, and then the conditioned medium is harvested. The medium containing the expressed antibody can then be concentrated and purified by any selected method.

Epitope-tagged variants of the antibody may also be expressed in host CHO cells. The DNA encoding the antibody ligated into pRK5 may be subcloned out of the pRK5 vector. The subclone insert can undergo PCR to fuse in frame with a selected epitope tag such as a poly-his tag into a Baculovirus expression vector. The poly-his tagged DNA encoding the antibody insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged antibody can then be concentrated and purified by any selected method, such as by $Ni^{2+}$-chelate affinity chromatography.

The antibody may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number and pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated at 4° C., in 20 mM Hepes, pH 7.4, buffer containing 0.3 M NaCl and 5 mM imidazole at a flow rate of 4-5 ml/min. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

EXAMPLE 11

Expression of Anti-PD-L1 Antibody in E. coli

This example illustrates preparation of an unglycosylated form of anti-PD-L1 antibody by recombinant expression in E. coli.

The DNA sequence encoding the anti-PD-L1 antibody is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the NPOR coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized antibody can then be purified using a metal chelating column under conditions that allow tight binding of the antibody.

Anti-PD-L1 antibody may also be expressed in E. coli in a poly-His tagged form, using the following procedure. The DNA encoding antibody is initially amplified using selected PCR primers. The primers contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min The supernatant is diluted with 3-5 volumes of metal chelate column buffer (6 M guanidine, 20 mM Tris, pH 7.4) and filtered through 0.22 micron filters to clarify. Depending on the condition, the clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein were pooled and stored at 4° C. Protein concentration is estimated by its absorbance at 280 nm using the calculated extinction coefficient based on its amino acid sequence.

The proteins are refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded anti-PD-L1 antibodies are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

What is claimed is:

1. An isolated heavy chain variable region polypeptide that specifically binds to PD-L1 comprising an HVR-H1, HVR-H2 and HVR-H3 sequence, wherein:

(a)
```
                                            (SEQ ID NO: 1)
the HVR-H1 sequence is GFTFSX₁SWIH;
```

(b)
```
                                            (SEQ ID NO: 2)
the HVR-H2 sequence is AWIX₂PYGGSX₃YYADSVKG;
```

(c)
```
                                            (SEQ ID NO: 3)
the HVR-H3 sequence is RHWPGGFDY;
``` further wherein: $X_1$ is D or G; $X_2$ is S or L; $X_3$ is T or S.

2. The polypeptide of claim 1 wherein $X_1$ is D; $X_2$ is S and $X_3$ is T.

3. The polypeptide of claim 1 further comprising variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4).

4. The polypeptide of claim 3 wherein the framework sequences are human.

5. The polypeptide of claim 4 wherein the framework sequences are VH subgroup III consensus framework.

6. The polypeptide of claim 5 wherein one or more of the framework sequences is the following:

```
                                            (SEQ ID NO: 4)
HC-FR1 is EVQLVESGGGLVQPGGSLRLSCAAS (SEQ ID NO: 5)
HC-FR2 is WVRQAPGKGLEWV (SEQ ID NO: 6)
HC-FR3 is RETISADTSKNTAYLQMNSLRAEDTAVYYCAR (SEQ ID NO: 7)
HC-FR4 is WGQGTLVTVSA.
```

7. The isolated heavy chain polypeptide of claim 1 in combination with a variable region light chain comprising an HVR-L1, HVR-L2 and HVR-L3, wherein:

(a)
```
                                           (SEQ ID NOs: 8)
the HVR-L1 sequence is RASQX₄X₅X₆TX₇X₈A;
```

(b)
```
                                           (SEQ ID NOs: 9)
the HVR-L2 sequence is SASX₉LX₁₀S,;
and
```

(c)
```
                                          (SEQ ID NOs: 10)
the HVR-L3 sequence is QQX₁₁X₁₂X₁₃X₁₄PX₁₅T;
``` further wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

8. The polypeptide of claim 7 wherein $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A.

9. The polypeptide of claim 7 further comprising variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4).

10. The polypeptide of claim 9 wherein the framework sequences are, human.

11. The polypeptide of claim 10 wherein the framework sequences are VL kappa I consensus framework.

12. The polypeptide of claim 11 wherein one or more of the framework sequences is the following:

```
                                          (SEQ ID NO: 11)
LC-FR1 is DIQMTQSPSSLSASVGDRVTITC;

(SEQ ID NO: 12)
LC-FR2 is WYQQKPGKAPKLLIY;

(SEQ ID NO: 13)
LC-FR3 is GVPSRFSGSGSGTDFTLTISSLQPEDFATYYC;

(SEQ ID NO: 14)
LC-FR4 is FGQGTKVEIKR.
```

13. An isolated anti-PD-L1 antibody or antigen binding fragment thereof, wherein the antibody or antibody fragment comprises a heavy chain and a light chain variable region sequence, wherein:

(a) the heavy chain comprises an HVR-H1, HVR-H2 and HVR-H3, wherein further:

(i)
```
                                            (SEQ ID NO: 1)
the HVR-H1 sequence is GFTFSX₁SWIH;
```

(ii)
```
                                            (SEQ ID NO: 2)
the HVR-H2 sequence is AWIX₂PYGGSX₃YYADSVKG;
```

(iii)
```
                                            (SEQ ID NO: 3)
the HVR-H3 sequence is RHWPGGFDY,;
and
```

(b) the light chain comprises an HVR-L1, HVR-L2 and HVR-L3, wherein further:

(iv)
```
                                           (SEQ ID NOs: 8)
the HVR-L1 sequence is RASQX₄X₅X₆TX₇X₈A;
```

(v)
```
                                           (SEQ ID NOs: 9)
the HVR-L2 sequence is SASX₉LX₁₀S;
```

(vi)
```
                                          (SEQ ID NOs: 10)
the HVR-L3 sequence is QQX₁₁X₁₂X₁₃X₁₄PX₁₅T;
``` wherein: $X_1$ is D or G; $X_2$ is S or L; $X_3$ is T or S; $X_4$ may be D or V; $X_5$ may be V or I; $X_6$ may be S or N; $X_7$ may be A or F; $X_8$ may be V or L; $X_9$ may be F or T; $X_{10}$ may be Y or A; $X_{11}$ may be Y, G, F, or S; $X_{12}$ may be L, Y, F or W; $X_{13}$ may be Y, N, A, T, G, F or I; $X_{14}$ may be H, V, P, T or I; $X_{15}$ may be A, W, R, P or T.

14. The antibody or antibody fragment of claim 13 wherein $X_1$ is D; $X_2$ is S and $X_3$ is T.

15. The antibody or antibody fragment of claim 13, wherein $X_4$=D, $X_5$=V, $X_6$=S, $X_7$=A and $X_8$=V, $X_9$=F, and $X_{10}$=Y, $X_{11}$=Y, $X_{12}$=L, $X_{13}$=Y, $X_{14}$=H and $X_{15}$=A.

16. The antibody or antibody fragment of claim 13, wherein $X_1$=D, $X_2$=S and $X_3$=T, $X_4$=D, $X_5$=V, $X_6$=S, $X_7$=A and $X_8$=V, $X_9$=F, and $X_{10}$=Y, $X_{11}$=Y, $X_{12}$=L, $X_{13}$=Y, $X_{14}$=H and $X_{15}$=A.

17. The antibody or antibody fragment of claim 14 further wherein the antibody or antibody fragment comprises:
variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4).

18. The antibody or antibody fragment of claim 17 wherein the framework sequences are human.

19. The antibody or antibody fragment of claim 18 wherein the variable region heavy chain framework sequences are VH subgroup III consensus framework.

20. The antibody or antibody fragment of claim 19 wherein one or more of the framework sequences is the following:

```
                                         (SEQ ID NO: 4)
HC-FR1 is EVQLVESGGGLVQPGGSLRLSCAAS;

(SEQ ID NO: 5)
HC-FR2 is WVRQAPGKGLEWV;

(SEQ ID NO: 6)
HC-FR3 is RFTISADTSKNTAYLQMNSLRAEDTAVYYCAR;

(SEQ ID NO: 7)
HC-FR4 is WGQGTLVTVSA.
```

21. The antibody or antibody fragment of claim 15 further wherein the antibody comprises:
variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4).

22. The antibody or antibody fragment of claim 21 wherein the variable region light chain framework sequences are VL kappa I consensus framework.

23. The antibody or antibody fragment of claim 22 wherein one or more of the framework sequences is the following:

```
                                        (SEQ ID NO: 11)
LC-FR1 is DIQMTQSPSSLSASVGDRVTITC;

(SEQ ID NO: 12)
LC-FR2 is WYQQKPGKAPKLLIY;

(SEQ ID NO: 13)
LC-FR3 is GVPSRFSGSGSGTDFTLTISSLQPEDFATYYC;
and (SEQ ID NO: 14)
LC-FR4 is FGQGTKVEIKR.
```

24. The antibody of or antibody fragment of claim 16 wherein the antibody or antibody fragment comprises:
(a) variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4), and
(b) variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4);
wherein the variable heavy chain framework sequences are the following:

```
                                         (SEQ ID NO: 4)
(i) HC-FR1 is EVQLVESGGGLVQPGGSLRLSCAAS;

(SEQ ID NO: 5)
(ii) HC-FR2 is WVRQAPGKGLEWV;

(SEQ ID NO: 6)
(iii) HC-FR3 is RFTISADTSKNTAYLQMNSLRAEDTAVYYCAR;

(SEQ ID NO: 7)
(iv) HC-FR4 is WGQGTLVTVSA;
and
``` further wherein the variable light chain framework sequences are the following:

```
                                        (SEQ ID NO: 11)
(i) LC-FR1 is DIQMTQSPSSLSASVGDRVTITC;

(SEQ ID NO: 12)
(ii) LC-FR2 is WYQQKPGKAPKLLIY;

(SEQ ID NO: 13)
(iii) LC-FR3 is GVPSRFSGSGSGTDFTLTISSLQPEDFATYYC;

(SEQ ID NO: 14)
(iv) LC-FR4 is FGQGTKVEIKR.
```

25. The antibody or antibody fragment of claim 24 further comprising a human constant region.

26. The antibody or antibody fragment of claim 25, wherein the constant region is selected from the group consisting of IgG1, IgG2, IgG3 and IgG4.

27. The antibody of antibody fragment of claim 26 wherein the constant region is IgG1.

28. The antibody or antibody fragment of claim 24, further comprising murine constant region.

29. The antibody or antibody fragment of claim 28 wherein the constant region is selected from the group consisting of IgG1, IgG2A, IgG2B and IgG3.

30. The antibody or antibody fragment of claim 29, wherein the constant region is IgG2A.

31. The antibody or antibody fragment of claim 26 having reduced or minimal effector function.

32. The antibody or antibody fragment of claim 31, wherein the minimal effector function results from an effector-less Fc mutation.

33. The antibody or antibody fragment of claim 32, wherein the effector-less Fc mutation is N297A.

34. The antibody or antibody fragment of claim 32, wherein the effector-less Fc mutation is D265A/N297A.

35. The antibody or antibody fragment of claim 31, wherein the minimal effector function results from aglycosylation.

36. An isolated anti-PD-L1 antibody or antigen binding fragment thereof, wherein the antibody or antibody fragment comprises a heavy chain and light chain variable region sequence, wherein:
(a) the heavy chain comprises the sequence: EVQLVESGGGLVQPGGSLRLS CAASGFTFSD-SWIHWVRQAPGKGLEWVAW- ISPYGGSTYYADSVKGRFTI SADTSKNTAYLQMNSLRAEDTAVYYCARRHWPGGFDYWGQGTLVTVS A (SEQ ID NO:20), and (b) the light chain comprises the sequence: DIQMTQSPSSLSASVGDRVTITC RASQDVSTAVAWYQQKPGKAPKWYSASFLYSGVPSRFSGSGSGTDFTL TISSLQPEDFATYYCQQYLYH PATFGQGTKVEIKR (SEQ ID NO:21).

37. The antibody or antibody fragment of claim 29 having reduced or minimal effector function.

38. The antibody or antibody fragment of claim 37, wherein the minimal effector function results from an effector-less Fc mutation.

39. The antibody or antibody fragment of claim 38, wherein the effector-less Fc mutation is N297A.

40. The antibody or antibody fragment of claim 38, wherein the effector-less Fc mutation is D265A/N297A.

41. The antibody or antibody fragment of claim 37, wherein the minimal effector function results from aglycosylation.

42. The antibody or antibody fragment of claim 36 further comprising a human constant region.

43. The antibody or antibody fragment of claim 42, wherein the constant region is selected from the group consisting of IgG1, IgG2, IgG3 and IgG4.

44. The antibody or antibody fragment of claim 43, wherein the constant region is IgG1.

45. The antibody or antibody fragment of claim 44 having reduced or minimal effector function.

46. The antibody or antibody fragment of claim 45, wherein the minimal effector function results from an effector-less Fc mutation.

47. The antibody or antibody fragment of claim 46, wherein the effector-less Fc mutation is N297A.

48. The antibody or antibody fragment of claim 46, wherein the effector-less Fc mutation is D265A/N297A.

49. The antibody or antibody fragment of claim 45, wherein the minimal effector function results from aglycosylation.

50. A composition comprising the anti-PD-L1 antibody or antigen binding fragment of any of claim 13-35, 36 or 21-49 and at least one pharmaceutically-acceptable carrier.

51. An article of manufacture comprising the composition of claim 50 and at least one chemotherapeutic agent.

52. The article of manufacture according to claim 51, wherein the chemotherapeutic agent is gemcitabine.

53. An article of manufacture comprising the composition of claim 50, and at least one B7-family costimulatory molecule.

54. An article of manufacture comprising the composition of claim 50 and at least one antibiotic.

55. The article of manufacture according to claim 54, wherein the antibiotic is an anti-viral agent.

56. The article of manufacture according to claim 55, wherein anti-viral agent is a reverse transcriptase inhibitor.

57. The article of manufacture according to claim 56, wherein the reverse transcriptase inhibitor is a polymerase inhibitor.

58. The article of manufacture according to claim 55, wherein the anti-viral agent is a protease inhibitor.

59. An article of manufacture comprising the composition of claim 50 and at least one vaccine.

60. An article of manufacture comprising the composition of claim 50.

61. The article of manufacture of claim 51, wherein the chemotherapeutic agent is an anti-VEGF antibody.

* * * * *

UNITED STATES PATENT AND TRADEMARK OFFICE

(12)  CERTIFICATE EXTENDING PATENT TERM
UNDER 35 U.S.C. § 156

(68) PATENT NO.       : 8,217,149

(45) ISSUED           : July 10, 2012

(75) INVENTOR         : Irving et al.

(73) PATENT OWNER     : Genentech, Inc.

(95) PRODUCT          : TECENTRIQ® (atezolizumab)

This is to certify that an application under 35 U.S.C. § 156 has been filed in the United States Patent and Trademark Office, requesting extension of the term of U.S. Patent No. 8,217,149 based upon the regulatory review of the product TECENTRIQ® (atezolizumab) by the Food and Drug Administration. According to United States Patent and Trademark Office records, the original expiration date of the patent as of the date of issuance of this certificate is December 8, 2029. Because it appears that the requirements of the law have been met, this certificate extends the term of the patent for the period of

(94)                    161 days subject to the payment of maintenance fees as provided by law, with all rights pertaining thereto as provided by 35 U.S.C. § 156.

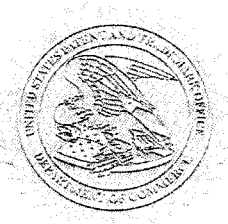

I have caused the seal of the United States Patent and Trademark Office to be affixed this 19th day of August 2020.

Andrei Iancu
Under Secretary of Commerce for Intellectual Property and
  Director of the United States Patent and Trademark Office

SEQUENCE LISTING

```
<160> NUMBER OF SEQ ID NOS: 40

<210> SEQ ID NO 1
<211> LENGTH: 10
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 6
<223> OTHER INFORMATION: residue is D or G

<400> SEQUENCE: 1

Gly Phe Thr Phe Ser Xaa Ser Trp Ile His
 1               5                  10

<210> SEQ ID NO 2
<211> LENGTH: 18
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 4
<223> OTHER INFORMATION: residue is S or L
<220> FEATURE:
<221> NAME/KEY: variant
<222> LOCATION: 10
<223> OTHER INFORMATION: residue is T or S

<400> SEQUENCE: 2

Ala Trp Ile Xaa Pro Tyr Gly Gly Ser Xaa Tyr Tyr Ala Asp Ser
 1               5                  10                  15

Val Lys Gly

<210> SEQ ID NO 3
<211> LENGTH: 9
<212> TYPE: PRT
<213> ORGANISM: Artificial sequence
<220> FEATURE:
<223> OTHER INFORMATION: sequence is synthesized

<400> SEQUENCE: 3

Arg His Trp Pro Gly Gly Phe Asp Tyr
 1               5

<210> SEQ ID NO 4
<211> LENGTH: 25
<212> TYPE: PRT
```

-continued

<213> ORGANISM: Artificial sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
 1               5                  10                  15

Gly Ser Leu Arg Leu Ser Cys Ala Ala Ser
             20                  25

<210> SEQ ID NO 5
<211> LENGTH: 13
<212> TYPE: PRT
<213> ORGANISM: Artificial sequence
<220> FEATURE:
<223> OTHER INFORMATION: sequence is synthesized

<400> SEQUENCE: 5

Trp Val Arg Gln Ala Pro Gly Lys Gly Leu Glu Trp Val
 1               5                  10

<210> SEQ ID NO 6
<211> LENGTH: 32
<212> TYPE: PRT
<213> ORGANISM: Artificial sequence
<220> FEATURE:
<223> OTHER INFORMATION: sequence is synthesized

<400> SEQUENCE: 6

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
             20                  25                  30

Ala Arg

<210> SEQ ID NO 7
<211> LENGTH: 11
<212> TYPE: PRT
<213> ORGANISM: Artificial sequence
<220> FEATURE:
<223> OTHER INFORMATION: sequence is synthesized

<400> SEQUENCE: 7

Trp Gly Gln Gly Thr Leu Val Thr Val Ser Ala
 1               5                  10

<210> SEQ ID NO 8
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 5
<223> OTHER INFORMATION: residue is D or V
<220> FEATURE:
<221> NAME/KEY: variant
<222> LOCATION: 6
<223> OTHER INFORMATION: residue is V or I
<220> FEATURE:
<221> NAME/KEY: variant
<222> LOCATION: 7
<223> OTHER INFORMATION: residue is S or N
<220> FEATURE:
<221> NAME/KEY: variant
<222> LOCATION: 9
<223> OTHER INFORMATION: residue is A or F
<220> FEATURE:

```
<221> NAME/KEY: variant
<222> LOCATION: 10
<223> OTHER INFORMATION: residue is V or L

<400> SEQUENCE: 8

Arg Ala Ser Gln Xaa Xaa Xaa Thr Xaa Xaa Ala
 1               5                  10

<210> SEQ ID NO 9
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 4
<223> OTHER INFORMATION: residue is F or T
<220> FEATURE:
<221> NAME/KEY: variant
<222> LOCATION: 6
<223> OTHER INFORMATION: residue is Y or A

<400> SEQUENCE: 9

Ser Ala Ser Xaa Leu Xaa Ser
 1               5

<210> SEQ ID NO 10
<211> LENGTH: 9
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 3
<223> OTHER INFORMATION: residue is Y, G, F or S
<220> FEATURE:
<221> NAME/KEY: variant
<222> LOCATION: 4
<223> OTHER INFORMATION: residue is L, Y, F, or W
<220> FEATURE:
<221> NAME/KEY: variant
<222> LOCATION: 5
<223> OTHER INFORMATION: residue is Y, N, A, T, G, F or I
<220> FEATURE:
<221> NAME/KEY: variant
<222> LOCATION: 6
<223> OTHER INFORMATION: residue is H, V, P, T or I
<220> FEATURE:
<221> NAME/KEY: variant
<222> LOCATION: 8
<223> OTHER INFORMATION: residue is A, W, R, P or T

<400> SEQUENCE: 10

Gln Gln Xaa Xaa Xaa Xaa Pro Xaa Thr
 1               5

<210> SEQ ID NO 11
<211> LENGTH: 23
<212> TYPE: PRT
<213> ORGANISM: Artificial sequence
<220> FEATURE:
<223> OTHER INFORMATION: sequence is synthesized

<400> SEQUENCE: 11

Asp Ile Gln Met Thr Gln Ser Pro Ser Ser Leu Ser Ala Ser Val
 1               5                  10                  15

Gly Asp Arg Val Thr Ile Thr Cys
                20
```

```
<210> SEQ ID NO 12
<211> LENGTH: 15
<212> TYPE: PRT
<213> ORGANISM: Artificial sequence
<220> FEATURE:
<223> OTHER INFORMATION: sequence is synthesized

<400> SEQUENCE: 12

Trp Tyr Gln Gln Lys Pro Gly Lys Ala Pro Lys Leu Leu Ile Tyr
 1               5                  10                  15

<210> SEQ ID NO 13
<211> LENGTH: 32
<212> TYPE: PRT
<213> ORGANISM: Artificial sequence
<220> FEATURE:
<223> OTHER INFORMATION: sequence is synthesized

<400> SEQUENCE: 13

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 14
<211> LENGTH: 11
<212> TYPE: PRT
<213> ORGANISM: Artificial sequence
<220> FEATURE:
<223> OTHER INFORMATION: sequence is synthesized

<400> SEQUENCE: 14

Phe Gly Gln Gly Thr Lys Val Glu Ile Lys Arg
 1               5                  10

<210> SEQ ID NO 15
<211> LENGTH: 10
<212> TYPE: PRT
<213> ORGANISM: Artificial sequence
<220> FEATURE:
<223> OTHER INFORMATION: sequence is synthesized

<400> SEQUENCE: 15

Gly Phe Thr Phe Ser Asp Ser Trp Ile His
 1               5                  10

<210> SEQ ID NO 16
<211> LENGTH: 18
<212> TYPE: PRT
<213> ORGANISM: Artificial sequence
<220> FEATURE:
<223> OTHER INFORMATION: sequence is synthesized

<400> SEQUENCE: 16

Ala Trp Ile Ser Pro Tyr Gly Gly Ser Thr Tyr Tyr Ala Asp Ser
 1               5                  10                  15

Val Lys Gly

<210> SEQ ID NO 17
<211> LENGTH: 11
<212> TYPE: PRT
<213> ORGANISM: Artificial sequence
<220> FEATURE:
<223> OTHER INFORMATION: sequence is synthesized

<400> SEQUENCE: 17
```

Arg Ala Ser Gln Asp Val Ser Thr Ala Val Ala
1               5                   10

<210> SEQ ID NO 18
<211> LENGTH: 7
<212> TYPE: PRT
<213> ORGANISM: Artificial sequence
<220> FEATURE:
<223> OTHER INFORMATION: sequence is synthesized

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial sequence
<220> FEATURE:
<223> OTHER INFORMATION: sequence is synthesized

<400> SEQUENCE: 19

Gln Gln Tyr Leu Tyr His Pro Ala Thr
1               5

<210> SEQ ID NO 20
<211> LENGTH: 118
<212> TYPE: PRT
<213> ORGANISM: Artificial sequence
<220> FEATURE:
<223> OTHER INFORMATION: sequence is synthesized

<400> SEQUENCE: 20

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Asp Ser Trp Ile His Trp Val Arg Gln Ala Pro Gly Lys Gly Leu
                35                  40                  45

Glu Trp Val Ala Trp Ile Ser Pro Tyr Gly Gly Ser Thr Tyr Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Arg His Trp Pro Gly Gly Phe
                95                  100                 105

Asp Tyr Trp Gly Gln Gly Thr Leu Val Thr Val Ser Ala
                110                 115

<210> SEQ ID NO 21
<211> LENGTH: 108
<212> TYPE: PRT
<213> ORGANISM: Artificial sequence
<220> FEATURE:
<223> OTHER INFORMATION: sequence is synthesized

<400> SEQUENCE: 21

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
                20                  25                  30

```
Thr Ala Val Ala Trp Tyr Gln Gln Lys Pro Gly Lys Ala Pro Lys
                 35                  40                  45

Leu Leu Ile Tyr Ser Ala Ser Phe Leu Tyr Ser Gly Val Pro Ser
             50                  55                  60

Arg Phe Ser Gly Ser Gly Ser Gly Thr Asp Phe Thr Leu Thr Ile
         65                  70                  75

Ser Ser Leu Gln Pro Glu Asp Phe Ala Thr Tyr Tyr Cys Gln Gln
             80                  85                  90

Tyr Leu Tyr His Pro Ala Thr Phe Gly Gln Gly Thr Lys Val Glu
             95                 100                 105

Ile Lys Arg

<210> SEQ ID NO 22
<211> LENGTH: 113
<212> TYPE: PRT
<213> ORGANISM: Homo sapiens

<400> SEQUENCE: 22

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
             20                  25                  30

Ser Tyr Ala Met Ser Trp Val Arg Gln Ala Pro Gly Lys Gly Leu
             35                  40                  45

Glu Trp Val Ser Val Ile Ser Gly Asp Gly Gly Ser Thr Tyr Tyr
             50                  55                  60

Ala Asp Ser Val Lys Gly Arg Phe Thr Ile Ser Arg Asp Asn Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Gly Phe Asp Tyr Trp Gly Gln
             95                 100                 105

Gly Thr Leu Val Thr Val Ser Ala
            110

<210> SEQ ID NO 23
<211> LENGTH: 118
<212> TYPE: PRT
<213> ORGANISM: Artificial sequence
<220> FEATURE:
<223> OTHER INFORMATION: sequence is synthesized

<400> SEQUENCE: 23

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
             20                  25                  30

Asp Ser Trp Ile His Trp Val Arg Gln Ala Pro Gly Lys Gly Leu
             35                  40                  45

Glu Trp Val Ala Trp Ile Ser Pro Tyr Gly Gly Ser Thr Tyr Tyr
             50                  55                  60

Ala Asp Ser Val Lys Gly Arg Phe Thr Ile Ser Ala Asp Thr Ser
             65                  70                  75

Lys Asn Thr Ala Tyr Leu Gln Met Asn Ser Leu Arg Ala Glu Asp
             80                  85                  90

Thr Ala Val Tyr Tyr Cys Ala Arg Arg His Trp Pro Gly Gly Phe
             95                 100                 105
```

```
Asp Tyr Trp Gly Gln Gly Thr Leu Val Thr Val Ser Ala
            110                 115

<210> SEQ ID NO 24
<211> LENGTH: 118
<212> TYPE: PRT
<213> ORGANISM: Artificial sequence
<220> FEATURE:
<223> OTHER INFORMATION: sequence is synthesized

<400> SEQUENCE: 24

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Gly Ser Trp Ile His Trp Val Arg Gln Ala Pro Gly Lys Gly Leu
             35                  40                  45

Glu Trp Val Ala Trp Ile Leu Pro Tyr Gly Gly Ser Ser Tyr Tyr
         50                  55                  60

Ala Asp Ser Val Lys Gly Arg Phe Thr Ile Ser Ala Asp Thr Ser
     65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Arg His Trp Pro Gly Gly Phe
             95                 100                 105

Asp Tyr Trp Gly Gln Gly Thr Leu Val Thr Val Ser Ala
            110                 115

<210> SEQ ID NO 25
<211> LENGTH: 108
<212> TYPE: PRT
<213> ORGANISM: Homo sapiens

<400> SEQUENCE: 25

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                 20                  25                  30

Asn Tyr Leu Ala Trp Tyr Gln Gln Lys Pro Gly Lys Ala Pro Lys
             35                  40                  45

Leu Leu Ile Tyr Ala Ala Ser Ser Leu Glu Ser Gly Val Pro Ser
         50                  55                  60

Arg Phe Ser Gly Ser Gly Ser Gly Thr Asp Phe Thr Leu Thr Ile
     65                  70                  75

Ser Ser Leu Gln Pro Glu Asp Phe Ala Thr Tyr Tyr Cys Gln Gln
                 80                  85                  90

Tyr Asn Ser Leu Pro Trp Thr Phe Gly Gln Gly Thr Lys Val Glu
             95                 100                 105

Ile Lys Arg

<210> SEQ ID NO 26
<211> LENGTH: 108
<212> TYPE: PRT
<213> ORGANISM: Artificial sequence
<220> FEATURE:
<223> OTHER INFORMATION: sequence is synthesized

<400> SEQUENCE: 26

Asp Ile Gln Met Thr Gln Ser Pro Ser Ser Leu Ser Ala Ser Val
  1               5                  10                  15
```

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Asn Val Pro Trp Thr Phe Gly Gln Gly Thr Lys Val Glu
            95                 100                 105

Ile Lys Arg

<210> SEQ ID NO 27
<211> LENGTH: 108
<212> TYPE: PRT
<213> ORGANISM: Artificial sequence
<220> FEATURE:
<223> OTHER INFORMATION: sequence is synthesized

<400> SEQUENCE: 27

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Ala Pro Pro Trp Thr Phe Gly Gln Gly Thr Lys Val Glu
            95                 100                 105

Ile Lys Arg

<210> SEQ ID NO 28
<211> LENGTH: 108
<212> TYPE: PRT
<213> ORGANISM: Artificial sequence
<220> FEATURE:
<223> OTHER INFORMATION: sequence is synthesized

<400> SEQUENCE: 28

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln 80                  85                  90
Tyr Tyr Thr Val Pro Trp Thr Phe Gly Gln Gly Thr Lys Val Glu
                   95                 100                 105

Ile Lys Arg

<210> SEQ ID NO 29
<211> LENGTH: 108
<212> TYPE: PRT
<213> ORGANISM: Artificial sequence
<220> FEATURE:
<223> OTHER INFORMATION: sequence is synthesized

<400> SEQUENCE: 29

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Val Ile Asn
                20                  25                  30

Thr Phe Leu Ala Trp Tyr Gln Gln Lys Pro Gly Lys Ala Pro Lys
                35                  40                  45

Leu Leu Ile Tyr Ser Ala Ser Thr Leu Ala Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Tyr Thr Val Pro Arg Thr Phe Gly Gln Gly Thr Lys Val Glu
                   95                 100                 105

Ile Lys Arg

<210> SEQ ID NO 30
<211> LENGTH: 108
<212> TYPE: PRT
<213> ORGANISM: Artificial sequence
<220> FEATURE:
<223> OTHER INFORMATION: sequence is synthesized

<400> SEQUENCE: 30

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Gly Tyr Gly Val Pro Arg Thr Phe Gly Gln Gly Thr Lys Val Glu
                   95                 100                 105

Ile Lys Arg

<210> SEQ ID NO 31
<211> LENGTH: 108
<212> TYPE: PRT
<213> ORGANISM: Artificial sequence
<220> FEATURE:
<223> OTHER INFORMATION: sequence is synthesized

<400> SEQUENCE: 31

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Leu Phe Thr Pro Pro Thr Phe Gly Gln Gly Thr Lys Val Glu
        95                  100                 105

Ile Lys Arg

<210> SEQ ID NO 32
<211> LENGTH: 108
<212> TYPE: PRT
<213> ORGANISM: Artificial sequence
<220> FEATURE:
<223> OTHER INFORMATION: sequence is synthesized

<400> SEQUENCE: 32

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Phe Ile Thr Pro Thr Thr Phe Gly Gln Gly Thr Lys Val Glu
        95                  100                 105

Ile Lys Arg

<210> SEQ ID NO 33
<211> LENGTH: 108
<212> TYPE: PRT
<213> ORGANISM: Artificial sequence
<220> FEATURE:
<223> OTHER INFORMATION: sequence is synthesized

<400> SEQUENCE: 33

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
            80                  85                  90

Tyr Tyr Tyr Thr Pro Pro Thr Phe Gly Gln Gly Thr Lys Val Glu
            95                  100                 105

Ile Lys Arg

<210> SEQ ID NO 34
<211> LENGTH: 108
<212> TYPE: PRT
<213> ORGANISM: Artificial sequence
<220> FEATURE:
<223> OTHER INFORMATION: sequence is synthesized

<400> SEQUENCE: 34

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
            80                  85                  90

Phe Phe Tyr Thr Pro Pro Thr Phe Gly Gln Gly Thr Lys Val Glu
            95                  100                 105

Ile Lys Arg

<210> SEQ ID NO 35
<211> LENGTH: 108
<212> TYPE: PRT
<213> ORGANISM: Artificial sequence
<220> FEATURE:
<223> OTHER INFORMATION: sequence is synthesized

<400> SEQUENCE: 35

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
            80                  85                  90

Ser Leu Phe Thr Pro Pro Thr Phe Gly Gln Gly Thr Lys Val Glu
            95                  100                 105

Ile Lys Arg

<210> SEQ ID NO 36

```
<211> LENGTH: 108
<212> TYPE: PRT
<213> ORGANISM: Artificial sequence
<220> FEATURE:
<223> OTHER INFORMATION: sequence is synthesized

<400> SEQUENCE: 36

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Leu Tyr Thr Pro Pro Thr Phe Gly Gln Gly Thr Lys Val Glu
            95                 100                 105

Ile Lys Arg

<210> SEQ ID NO 37
<211> LENGTH: 108
<212> TYPE: PRT
<213> ORGANISM: Artificial sequence
<220> FEATURE:
<223> OTHER INFORMATION: sequence is synthesized

<400> SEQUENCE: 37

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Trp Tyr His Pro Pro Thr Phe Gly Gln Gly Thr Lys Val Glu
            95                 100                 105

Ile Lys Arg

<210> SEQ ID NO 38
<211> LENGTH: 108
<212> TYPE: PRT
<213> ORGANISM: Artificial sequence
<220> FEATURE:
<223> OTHER INFORMATION: sequence is synthesized

<400> SEQUENCE: 38

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30
```

```
Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Phe Tyr Ile Pro Pro Thr Phe Gly Gln Gly Thr Lys Val Glu
            95                 100                 105

Ile Lys Arg

<210> SEQ ID NO 39
<211> LENGTH: 108
<212> TYPE: PRT
<213> ORGANISM: Artificial sequence
<220> FEATURE:
<223> OTHER INFORMATION: sequence is synthesized

<400> SEQUENCE: 39

Asp Ile Gln Met Thr Gln Ser Pro Ser Ser Leu Ser Ala Ser Val
1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Trp Tyr Thr Pro Thr Thr Phe Gly Gln Gly Thr Lys Val Glu
            95                 100                 105

Ile Lys Arg

<210> SEQ ID NO 40
<211> LENGTH: 108
<212> TYPE: PRT
<213> ORGANISM: Artificial sequence
<220> FEATURE:
<223> OTHER INFORMATION: sequence is synthesized

<400> SEQUENCE: 40

Asp Ile Gln Met Thr Gln Ser Pro Ser Ser Leu Ser Ala Ser Val
1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90
```

```
Ser Tyr Phe Ile Pro Pro Thr Phe Gly Gln Gly Thr Lys Val Glu
            95              100                 105
Ile Lys Arg
```